United States Patent
Dar et al.

(10) Patent No.: US 12,201,448 B2
(45) Date of Patent: Jan. 21, 2025

(54) HEADSET FOR NEUROSTIMULATION AND SENSING OF BODY PARAMETERS

(71) Applicant: NEUROLIEF LTD., Yokneam Illit (IL)

(72) Inventors: Amit Dar, Kfar Hess (IL); Jonathan Bar-Or, Pardes Hana Karkur (IL); Amir Cohen, Ra'anana (IL); Ron Belson, Tel Aviv (IL)

(73) Assignee: NEUROLIEF LTD., Yokneam Illit (IL)

( * ) Notice: Subject to any disclaimer, the term of this patent is extended or adjusted under 35 U.S.C. 154(b) by 1070 days.

(21) Appl. No.: 15/510,067

(22) PCT Filed: Sep. 16, 2015

(86) PCT No.: PCT/IB2015/057130
§ 371 (c)(1),
(2) Date: Mar. 9, 2017

(87) PCT Pub. No.: WO2016/042499
PCT Pub. Date: Mar. 24, 2016

(65) Prior Publication Data
US 2017/0296121 A1    Oct. 19, 2017

Related U.S. Application Data

(60) Provisional application No. 62/051,643, filed on Sep. 17, 2014.

(51) Int. Cl.
*A61B 5/00* (2006.01)
*A61B 5/291* (2021.01)
(Continued)

(52) U.S. Cl.
CPC ............ *A61B 5/6803* (2013.01); *A61B 5/291* (2021.01); *A61N 1/0456* (2013.01);
(Continued)

(58) Field of Classification Search
CPC ... A61B 5/6803; A61B 5/0478; A61B 5/0492; A61B 5/0531; A61B 5/0535;
(Continued)

(56) References Cited

U.S. PATENT DOCUMENTS 3,735,753 A * 5/1973 Pisarski ............... A61B 5/0478
600/383
6,077,237 A * 6/2000 Campbell ............... G06F 3/011
607/139

(Continued)

FOREIGN PATENT DOCUMENTS

WO    2007138598 A2    12/2012
WO    2014141213 A2    9/2014

OTHER PUBLICATIONS

International Search Report for PCT/IB2015/057130 mailed Dec. 22, 2015.
Written Opinion for PCT/IB2015/057130 mailed Dec. 22, 2015.

*Primary Examiner* — Eun Hwa Kim
*Assistant Examiner* — Catherine Premraj
(74) *Attorney, Agent, or Firm* — Momentum IP; Marc Van Dyke

(57) ABSTRACT

A headset for use in delivering electrical stimulation to the skin surface of the head or in sensing one or more parameters of the head of a user.

19 Claims, 23 Drawing Sheets

(51) Int. Cl.
*A61N 1/04* (2006.01)
*A61B 5/0531* (2021.01)
*A61B 5/296* (2021.01)

(52) U.S. Cl.
CPC .......... *A61N 1/0484* (2013.01); *A61B 5/0531* (2013.01); *A61B 5/296* (2021.01); *A61B 2562/0215* (2017.08); *A61B 2562/0217* (2017.08)

(58) Field of Classification Search
CPC .... A61B 2562/0215; A61B 2562/0217; A61B 5/291; A61B 5/296; A61N 1/0456; A61N 1/00484; A61N 1/0484
See application file for complete search history.

(56) References Cited

U.S. PATENT DOCUMENTS

| | | | |
|---|---|---|---|
| 2004/0073129 A1 | 4/2004 | Caldwell et al. | |
| 2006/0167524 A1* | 7/2006 | Kimura | A61N 1/0456 607/45 |
| 2008/0221472 A1* | 9/2008 | Lee | A61B 5/369 600/544 |
| 2011/0319975 A1 | 12/2011 | Ho et al. | |
| 2013/0104288 A1* | 5/2013 | Schlottau | A61B 5/6814 2/209.13 |
| 2013/0274583 A1* | 10/2013 | Heck | A61B 5/0488 600/383 |
| 2013/0282095 A1* | 10/2013 | Mignolet | A61N 1/0456 607/139 |
| 2013/0296967 A1 | 11/2013 | Skaribas et al. | |
| 2013/0310676 A1* | 11/2013 | Jung | A61B 5/291 600/383 |
| 2014/0081369 A1* | 3/2014 | Sosa | A61N 1/0484 607/139 |
| 2014/0276183 A1* | 9/2014 | Badower | A61B 5/0476 600/544 |
| 2014/0330142 A1* | 11/2014 | Banet | A61B 5/0205 600/484 |
| 2016/0022211 A1* | 1/2016 | Gillette | A61B 5/6803 600/383 |

* cited by examiner

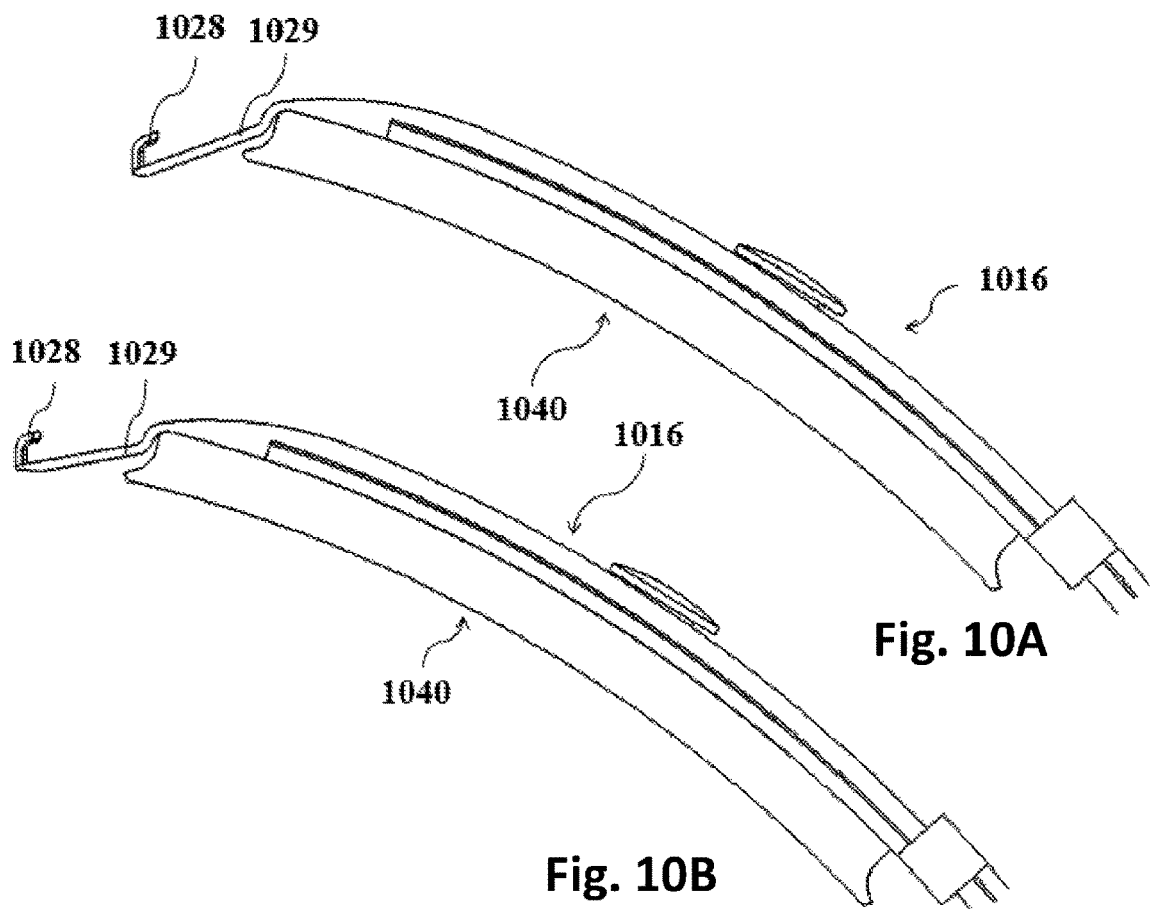
Fig. 10A
Fig. 10B
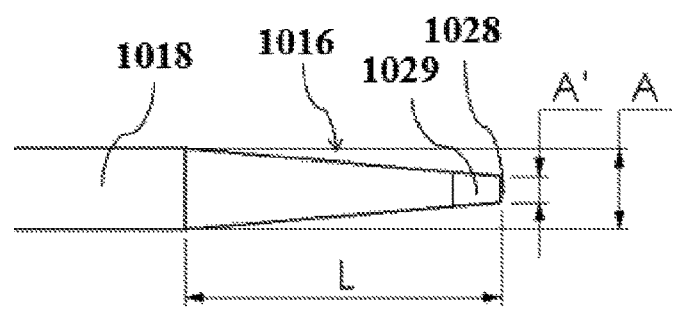
Fig. 10C
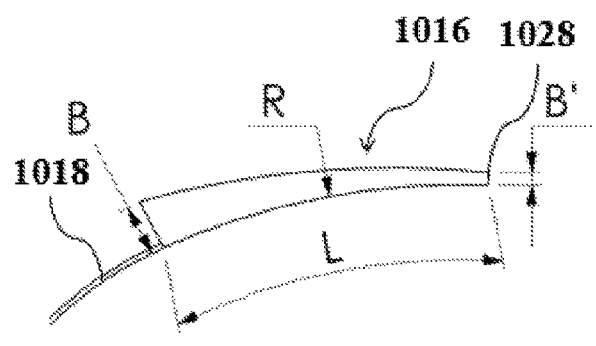
Fig. 10D

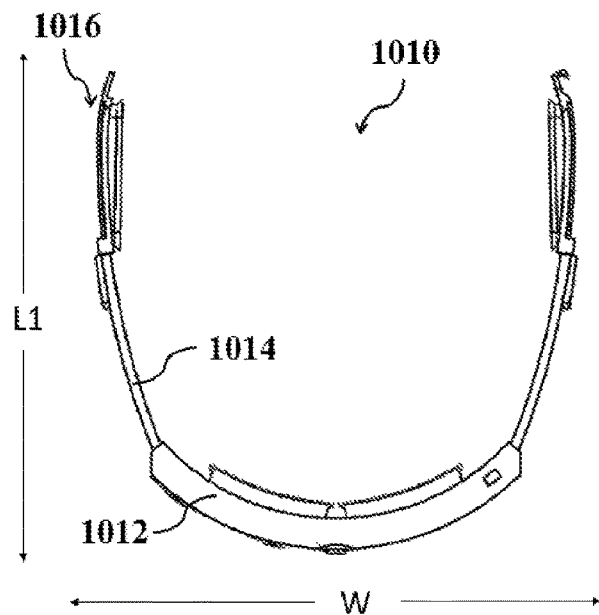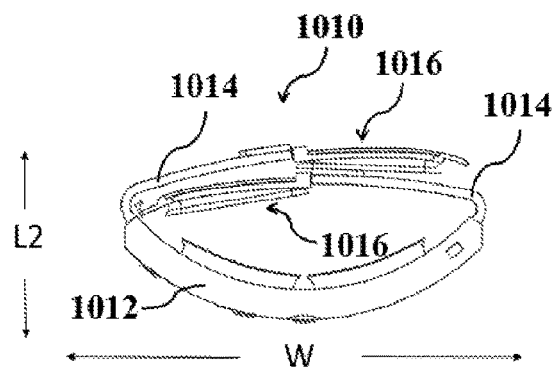
Fig. 11A  Fig. 11B
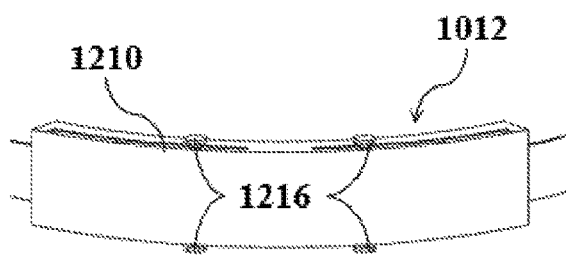
Fig. 12A
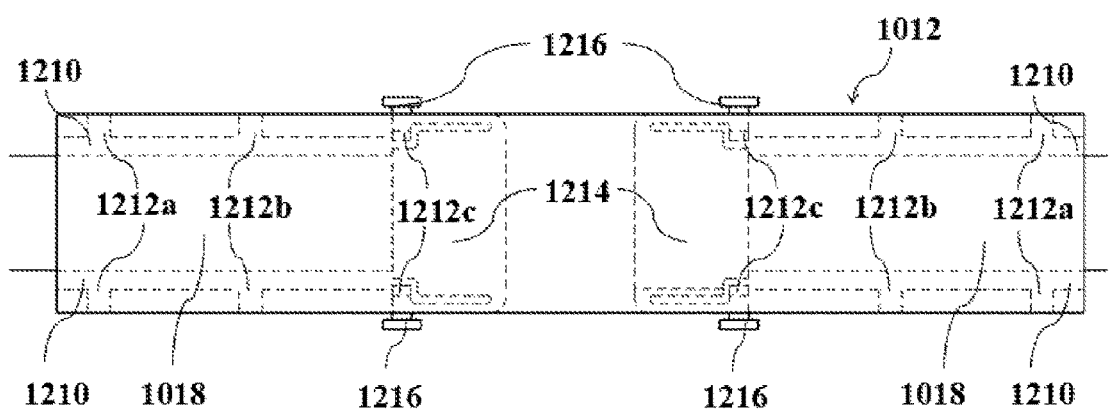
Fig. 12B

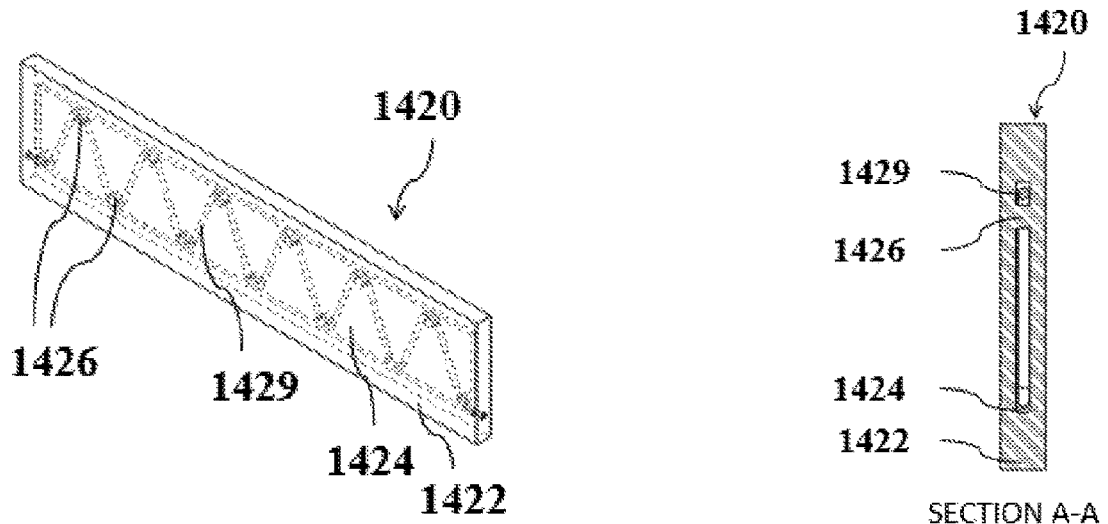
Fig. 22A
Fig. 22D
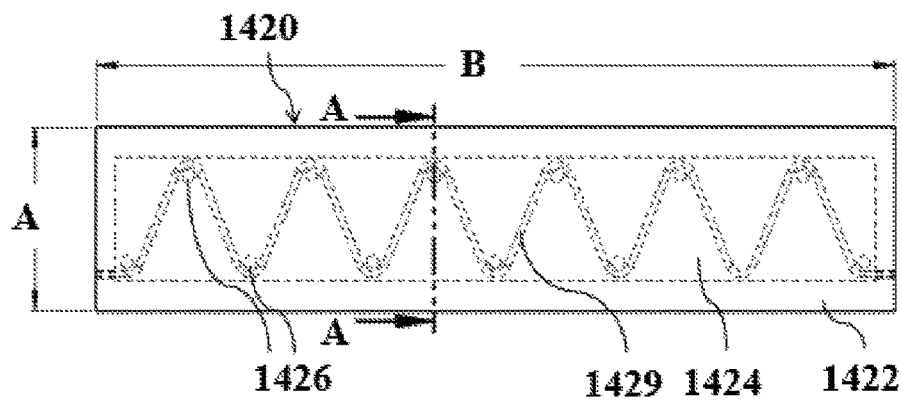
Fig. 22B
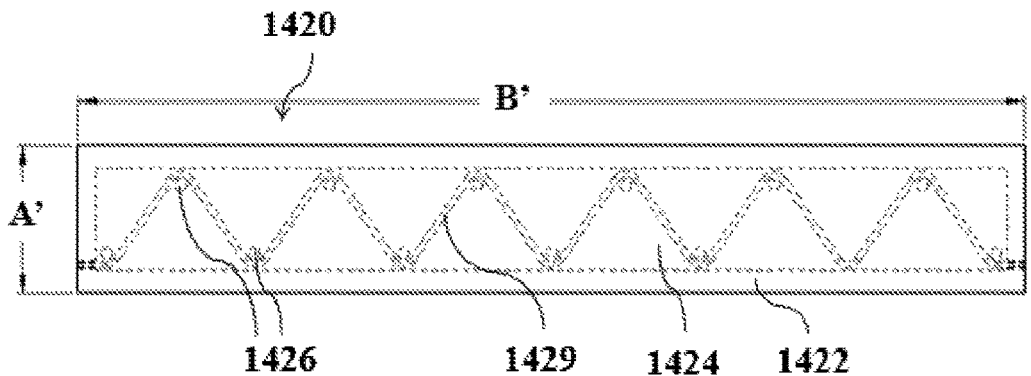
Fig. 22C

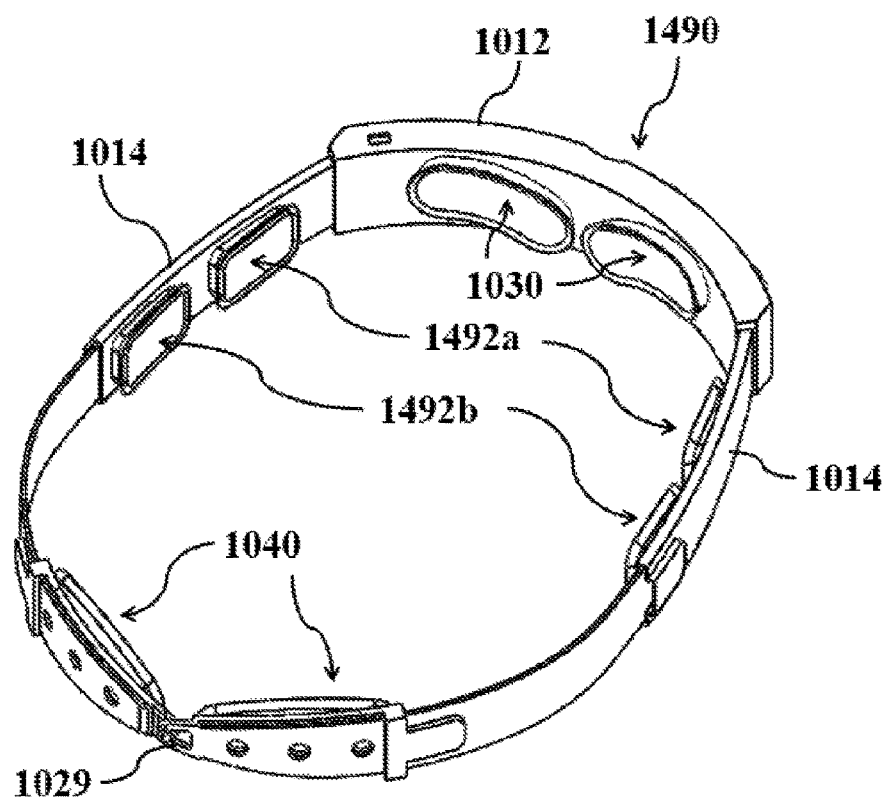
Fig. 29
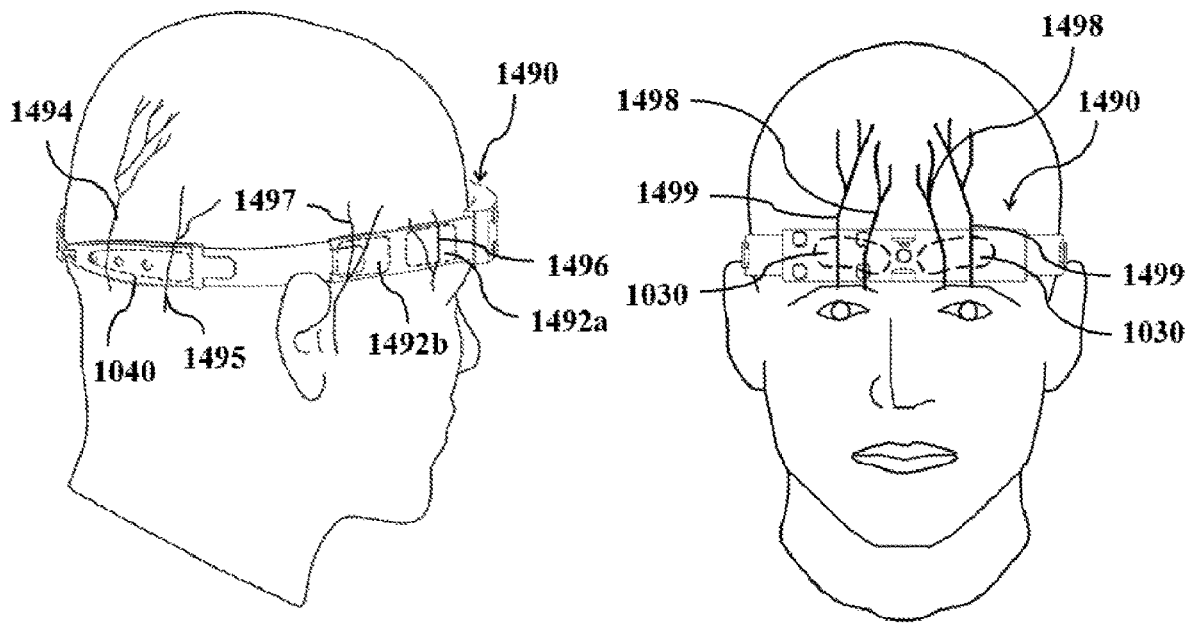
Fig. 30A  Fig. 30B

HEADSET FOR NEUROSTIMULATION AND SENSING OF BODY PARAMETERS

RELATED APPLICATION

The present application is a national phase filing of PCT Patent Application No. PCT/IB2015/057130 filed Sep. 16, 2015 and entitled HEADSET FOR NEUROSTIMULATION AND SENSING OF BODY PARAMETERS, which gains priority from U.S. Provisional Patent Application No. 62/051,643 filed Sep. 18, 2014 and entitled HEADSET FOR NEUROSTIMULATION AND SENSING. OF BODY PARAMETERS, both of which are incorporated herein by reference as if fully set forth herein.

FIELD OF THE INVENTION

The present invention relates to apparatus and methods for applying electrical stimulation to the head region, to headsets having electrodes for treatment of medical conditions using non-invasive electrical stimulation, to headsets adapted to assess medical conditions, and to electrode arrangements for use with such headsets.

BACKGROUND OF THE INVENTION

The present invention relates to apparatus and methods for applying electrical stimulation to the head region. The disclosed apparatus may be used for stimulation of peripheral and cranial nerves, for transcranial stimulation of brain regions, and for sensing various body parameters.

Peripheral and cranial nerves in the head region may be stimulated to treat various conditions such as chronic pain, migraine, tension headaches, cluster headaches, fibromyalgia, depression, post-traumatic stress syndrome, anxiety, stress, bipolar disorder, schizophrenia, obsessive compulsive disorder (OCD), insomnia, epilepsy, attention deficit disorder (ADD), attention deficit hyperactivity disorder (ADHD), Parkinson's disease, Alzheimer's disease, multiple sclerosis, and brain injuries such as stroke and traumatic brain injury (TBI). The anatomy of peripheral and cranial nerves in the head region, such as that of the occipital and trigeminal nerves, and their projections to brainstem regions such as the locus coeruleus and nucleus raphe magnus as well as to higher brain regions such as the thalamus and the cortex, may be advantageous when stimulating these nerves for treatment of such conditions.

Neurostimulation of superficial peripheral and cranial nerves in the head region, such as the occipital and trigeminal nerves, can be applied either invasively or non-invasively. Invasive procedures of peripheral nerve stimulation include occipital nerve stimulation, which has shown to provide relief for chronic migraine in numerous clinical trials. Another more recent procedure for treatment of migraine combines stimulation of both occipital nerve branches (greater and lesser) and trigeminal nerve branches (mostly supraorbital and supratrochlear and occasionally also/or zygomaticotemporal and auriculotemporal). Recent clinical results support the expectation that applying peripheral nerve stimulation to a combination of the occipital and trigeminal nerve branches may result in a better outcome compared to stimulation of the occipital nerve or the trigeminal nerve alone. Indeed, the response rate for patients with head-wide pain who were treated with implanted peripheral nerve stimulation to the occipital and trigeminal nerves is reported to be better than 80%. This is an improvement from using stimulation to the occipital or trigeminal nerves only which is reported to bring about just a 40% response rate. However, implanted peripheral nerve stimulation remains an invasive and costly procedure with a high rate of complications including infection, bleeding or fluid collection under the skin, as well as hardware-related malfunctions such as migration and breakage of the implanted leads and pulse generator failure.

Non-invasive stimulation of trigeminal nerve branches, such as the supraorbital and supratrochlear, was found to be safe as a preventive therapy for migraine and as treatment for other conditions such as seizures and depression. Due to the challenge of transferring current through the hair, stimulation of the occipital nerve (greater, lesser and third occipital branches) is mostly performed with implanted nerve stimulators. In spite of that, the occipital nerve branches may also be stimulated transcutaneously. When passing at approximately the anatomical height of the superior nuchal line of the occipital bone, the occipital nerve lies superficially under the skin and if electrodes are placed under the hair and close enough to the scalp, effective nerve excitation can be reached, achieving similar clinical benefits to those of implanted stimulation, without the risks associated with an invasive procedure.

Transcranial direct current stimulation (tDCS) is another modality that has been studied for treatment of various medical and/or physiological conditions such as chronic pain, migraine, depression, post-traumatic stress disorder, bipolar disorder, schizophrenia, epilepsy, attention deficit disorder (ADD), attention deficit hyperactivity disorder (ADHD), Parkinson's disease, and Alzheimer's disease, as well as for assistance in recovery from stroke and traumatic brain injury and in cognitive learning. tDCS typically refers to the application of constant, low current stimulation in the range of 1-2 mA, delivered directly to an area of the brain, thereby to modulate the activity of targeted neurons. Typically, the electrode associated with the positive pole, or anode, causes an increase in activity of the target nerve, while the electrode associated with the negative pole, or cathode, causes a decrease in nerve activity.

SUMMARY OF THE INVENTION

According to some teachings of the present invention there is provided a headset comprising an elongate body member sufficiently long to encircle the head of a user, the elongate body member having a closed state and a rest or relaxed state, a closure mechanism associated with ends of the body member, the closure mechanism having an open state and a closed state, wherein the body member is in the rest state when the closure mechanism is in the open state and the body member is in the closed state and forms a circumferential headset when the closure mechanism is in the closed state, and at least one electrode or at least one sensor, mounted on the body member, configured, when the headset is donned on the user's head, to be positioned against the skin of the head of the user, and electrically communicating with a processing unit.

In some embodiments, in the closed state the headset has a first length, and in the rest state the headset has a second length, the second length being shorter than the first length. In some embodiments, the first length is not greater than 65 cm, not greater than 63 cm, or not greater than 61 cm. In some embodiments, the first length is not less than 30 cm, not less than 35 cm, or not less than 40 cm.

In some embodiments, the second length is not more than 95%, not more than 93%, or not more than 91% of the first length. In some embodiments, the second length is not less than 8%, not less than 10%, or not less than 12% of the first length.

In some embodiments, the body member comprises at least one posterior member, the at least one posterior member being at least semi-rigid and configured, during donning of the headset, to plow between hair to access the scalp of the user, such that when the headset is donned the at least one electrode or the at least one sensor is in at least one of direct physical contact and direct electrical contact with the scalp of the user.

In some embodiments, the at least one posterior member comprises an at least partially tapered member, tapering from a first portion having a first width to a second portion having a second width, smaller than the first width.

In some embodiments, at least one of the at least one electrode comprises a posterior electrode at least partially mounted on the posterior member. In some embodiments, the posterior electrode is configured, when the headset is donned, to be disposed above at least one occipital nerve branch of the user. In some embodiments, the posterior electrode comprises a bifurcated posterior electrode being configured, when the headset is donned, to be disposed above two vertically aligned points on at least one occipital nerve branch of the user.

In some embodiments, during the plowing, the closure mechanism is in a plowing position, substantially aligned with a plane of the posterior member adapted to be adjacent to the head of the user, and in a rest state of the headset the closure mechanism is in a second position, pointing downward relative to the plane of the posterior member.

In some embodiments, the posterior member also comprises at least one electrically insulating grip portion adapted for engaging fingers of the user.

In some embodiments, the body member also comprises an at least semi-rigid anterior member and an interim member disposed between the anterior member and the at least one posterior member, wherein at least in the rest state of the headset, the anterior member and the at least one posterior member form a monolithic and/or integral unit.

In some embodiments, in the closed state of the headset, the anterior member and the at least one posterior member are vertically movable relative to one another.

In some embodiments, the interim member comprises a semi-rigid portion and a stretchable portion, wherein in the rest state the semi-rigid portion defines the structure of the interim member, such that the interim member contributes to the monolithic and/or integral unit.

In some embodiments, in the closed state of the body member the stretchable portion is stretched to extend beyond the length of the semi-rigid portion thereby defining a flexible portion at which the anterior member and the at least one posterior member are vertically movable relative to one another.

In some embodiments, the stretchable portion comprises a single stretchable element. In some embodiments, the stretchable portion comprises a plurality of stretchable elements. In some embodiments, the stretchable portion comprises a spring, such as a stainless steel spring or a constant force spring.

In some embodiments, the semi-rigid portion comprises a semi-rigid sleeve attached to the anterior member, and the stretchable portion comprises a stretchable band extending through the semi-rigid sleeve, in the rest state, the semi-rigid portion engages the posterior member thereby to form the monolithic and/or integral unit of the anterior member, the interim member, and the posterior member, and in the closed state, the stretchable band is stretched to a length greater than a length of the semi-rigid sleeve, thereby distancing the posterior member from the anterior member, disengaging the semi-rigid portion from the posterior member, and defining a flexible segment of the interim member at which the posterior member can be moved vertically relative to the anterior member and to the semi-rigid sleeve.

In some embodiments, the semi-rigid portion comprises a semi-rigid core attached to the anterior member, and the stretchable portion comprises a stretchable sleeve, the semi-rigid core being threaded through the stretchable sleeve, in the rest state, the stretchable sleeve is substantially the same length as the semi-rigid core, and semi-rigid core engages a slot in the posterior member thereby to form the monolithic and/or integral unit of the anterior member, the interim member, and the posterior member, and in the closed state, the stretchable sleeve is stretched to a length greater than a length of the semi-rigid core, thereby distancing the posterior member from the anterior member, releasing the core from the slot in the posterior member, and defining a flexible segment of the interim member at which the posterior member can be moved vertically relative to the anterior member and to the semi-rigid sleeve.

In some embodiments, at least one of the at leak one electrode comprises an anterior electrode mounted on an inner surface of the anterior member. In some embodiments, the anterior electrode is configured, when the headset is donned, to be disposed above at least one of the supratrochlear nerves and the supraorbital nerves of the user.

In some embodiments, the anterior member comprises at least one positioning indicator enabling the user, during donning of the headset, to center the anterior member on the head of the user such that the at least one electrode or the at least one sensor is accurately positioned when the headset is donned.

In some embodiments, the processing unit is disposed within the anterior member.

In some embodiments, the processing unit comprises a control element, functionally associated with the at least one electrode or with the at least one sensor, and configured to control operation of the at least one electrode or of the at least one sensor.

In some embodiments, the processing unit comprises a receiver, functionally associated with the at least one electrode or with the at least one sensor, and configured to receive input from the at least one electrode or from the at least one sensor. In some embodiments the receiver may be any kind of wired or wireless receiver.

In some embodiments, the processing unit comprises a transceiver, functionally associated with the at least one electrode or with the at least one sensor, and configured to control operation of and to receive input from the at least one electrode or the at least one sensor. In some embodiments the receiver may be any kind of wired or wireless transceiver.

In some embodiments, the processing unit is mounted on the body member and communicates with the at least one electrode or at least one sensor via at least one electrical conductor. In some embodiments, at least part of the at least one electrical conductor passes through a stretchable portion of the body member.

In some embodiments, the at least one stretchable portion comprises a stretchable resilient element comprising a plurality of geometrical shapes having a hollow center and connected to one another by bridging portions, the electrical conductor being threaded through the geometrical shapes of the stretchable element and being maintained in a fixed position therein relative to the geometrical shapes, wherein stretching of the stretchable element results in deformation of the geometrical shapes and in deformation of a threading shape of the electrical conductor, without damaging the electrical conductor.

In some embodiments, the at least one stretchable portion comprises a stretchable resilient band having a channel formed therein such that in each segment of the stretchable resilient band a length of the channel is greater than a length of the segment, the electrical conductor being threaded through the channel and being at least partially fixed within the channel relative to the band, wherein stretching of the stretchable band results in a change in the shape of the channel and of the electrical conductor threaded therethrough, without damaging the electrical conductor.

In some embodiments, the at least one stretchable portion comprises a stretchable resilient band having a hollow channel formed therein and a plurality of pins formed within the hollow channel, the electrical conductor being threaded through the channel around the pins and being movable within the channel relative to the pins, wherein stretching of the stretchable band results in an extension of distances between the pins and in a corresponding change in an arrangement of the electrical conductor around the pins, without damaging the electrical conductor.

In some embodiments, the headset also comprises a power supply, functionally associated with the at least one electrode or with the at least one sensor, providing electrical current to the at least one electrode or to the at least one sensor for operation thereof.

In some embodiments, the at least one electrode comprising a stimulating electrode configured to deliver electrical stimulation to a skin surface of the head of the user. In some embodiments, the stimulating electrode is disposed, when the headset is donned, above a nerve or nerve junction and being configured to deliver the electrical stimulation to the nerve or nerve junction. In some embodiments, the stimulating electrode is configured to deliver the electrical stimulation to at least one brain region of the user.

In some embodiments, the at least one electrode comprises a sensing electrode configured to sense at least one electrical parameter of a body portion of the user.

In some embodiments, at least part of the body member is flexible. In some embodiments, at least part of the body member is stretchable.

In some embodiments, at least one of the at least one electrode comprises a side electrode mounted on an inner surface of the body member. In some embodiments, the side electrode is configured to be disposed, when the headset is donned, above at least one of the zygomaticotemporal nerve and the auriculotemporal nerve of the user. In some embodiments, the side electrode is configured to be disposed, when the headset is donned, above the temple of the user and anterior to the ear of the user.

In some embodiments, the headset also comprises at least one size adjustment mechanism, enabling adjustment of the circumference of the body member to comfortably fit circumferentially about the head of the user.

In some embodiments, the at least one size adjustment mechanism is configured to change the physical length of the body member. In some embodiments, the at least one size adjustment mechanism is configured to change an elastic length of an elastic portion of the body member, without changing the physical length of the body member.

In some embodiments, the headset also comprises a nose bridge portion, attached to the body member at a center thereof, and positionable on a nose bridge of the user during donning the headset. In some embodiments, the nose bridge portion is removably and replaceably attached to the body member.

In some embodiments, the headset also comprises an eyeglasses portion, attached to the body member at a center thereof, and positionable over eyes of the user during donning of the headset. In some embodiments, the eyeglasses portion is removably and replaceably attached to the body member.

In some embodiments, the closure mechanism comprises, at each of the ends, a magnet, at least a portion of which defines a spherical surface, the magnet disposed in a magnet housing, wherein the spherical surfaces of the magnets are adapted to engage one another at a single point, thereby to close the headset. In some such embodiments, the magnets are adapted to attract one another so as to close the headset when the magnets are at a distance not greater than 10 mm, not greater than 20 mm, or not greater than 30 mm. In some embodiments, the magnets are rotatably disposed in the magnet housing and are adapted to automatically orient in an optimally polar orientation given a specific alignment of the ends of the headset.

According to some teachings of the present invention there is also provided a method of donning a headset on the head of a user, the method comprising providing a headset according to the teachings herein, the headset being in the rest state, positioning the headset adjacent the head of the user, such that at least one portion of the headset is positioned against the skin of the head of the user, while the body member is in the rest state, and using the closure mechanism, closing the body member into the closed state, thereby encircling the head of the user and securing the headset on the head of the user.

In some embodiments, the method also comprises, prior to the closing, pushing the headset rearward, thereby plowing through the hair and clearing an area of the scalp of the user for physical contact of the at least one electrode or the at least one sensor therewith.

In some embodiments, the method also comprises during the pushing, holding the body member at electrically insulating grips forming part of the body member.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like functionalities, but not necessarily identical elements.

In the drawings:

FIGS. 10A and 10B are side views of a posterior member, including a tapered end and a closure mechanism, of the inventive headset of FIGS. 1A and 1B, in a rest state and in a hair plowing state, respectively;

FIGS. 10C and 10D are schematic top and side plan views of a posterior member of an inventive headset suitable for plowing through the hair according to the teachings herein;

FIGS. 11A and 11B provide top plan views of the inventive headset of FIGS. 1A and 1B in a rest state, in an open and a folded position, respectively;

FIGS. 12A and 12B are a perspective view and a front plan view of an anterior member of the inventive headset of FIGS. 1A and 1B, including an embodiment of a size adjustment mechanism according to the teachings herein;

FIGS. 22A, 22B, 22C, and 22D provide views of yet another embodiment of a stretchable member having conductive wiring extending therethrough, which stretchable member is suitable for use in inventive headsets according to the teachings herein, FIG. 22A providing a perspective view, FIGS. 22B and 22C providing side plan views in a rest state and in a stretched state, respectively, and FIG. 22D providing a sectional view taken along section lines A-A in FIG. 22B;

FIG. 29 is a perspective view of an embodiment of the inventive headset of FIGS. 1A and 1B, including side electrodes;

FIGS. 30A and 30B provide schematic illustrations of the headset of FIG. 29 positioned on the head of a user, such that electrodes included therein stimulate specific nerve junctions in the head of the user;

DETAILED DESCRIPTION

Device and methods are described herein that include a headset with one or more integrated electrodes for applying electrical stimulation to peripheral nerves, cranial nerves and brain regions. The inventive headset is a head mounted construction that can be served as a platform for applying electrical stimulation to treat various conditions such as migraine and tension headaches, fibromyalgia, depression, post-traumatic stress syndrome, anxiety, obsessive compulsive disorder (OCD), insomnia, epilepsy, attention deficit hyperactivity disorder (ADHD), Parkinson's disease, Alzheimer's disease, multiple sclerosis, and stroke. The inventive headset may facilitate motor and cognitive learning and may induce relaxation. The inventive headset may also serve as a platform for various sensors, in order to detect and/or assess various conditions.

The stimulation electrodes and the quality of its contact with the scalp are a fundamental aspect in the functionality of the invented apparatus. Ensuring optimal conductivity between the electrodes and the scalp is essential for proper transfer of the electrical current to the target tissues, which is the basis for an effective treatment. Improper conductivity may result in failure of the therapy, unpleasant sensation and even skin irritation due to "hot spots" of high current density. The inventors have also found that non-invasive application of electrical current to the head region, no matter which indication it is applied for, may pose numerous challenges including stimulation in the presence of hair, high level of sensory sensitivity of the scalp and forehead, the criticality of robust contact and electrical conductivity between the electrodes and the scalp, despite variations in head size and contours, and accurate placement of the stimulating electrodes above the target nerve and brain regions.

Several aspects of the present invention relate to features that are aimed at ensuring that the electrical current is properly delivered from the electrode to the target tissues and for treating and assessing the head region in an effective and comfortable manner.

Figure 1A:
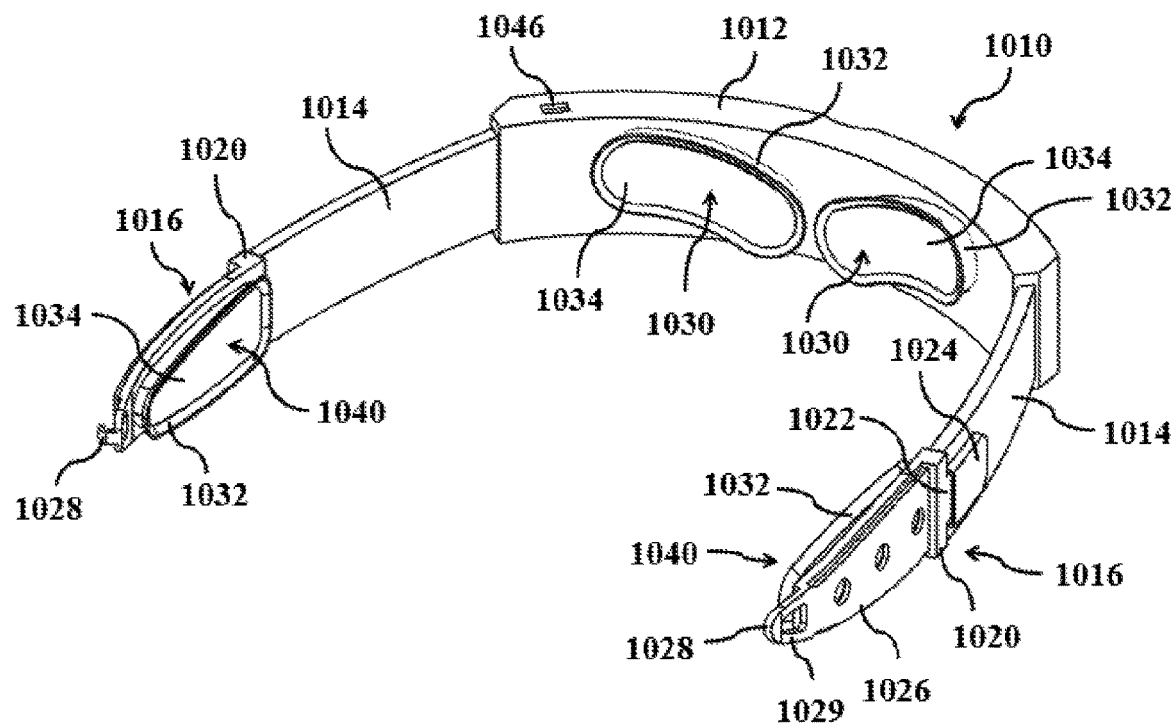
FIGS. 1A and 1B are perspective views of an embodiment of an inventive headset according to the teachings herein.
Figure 1B:
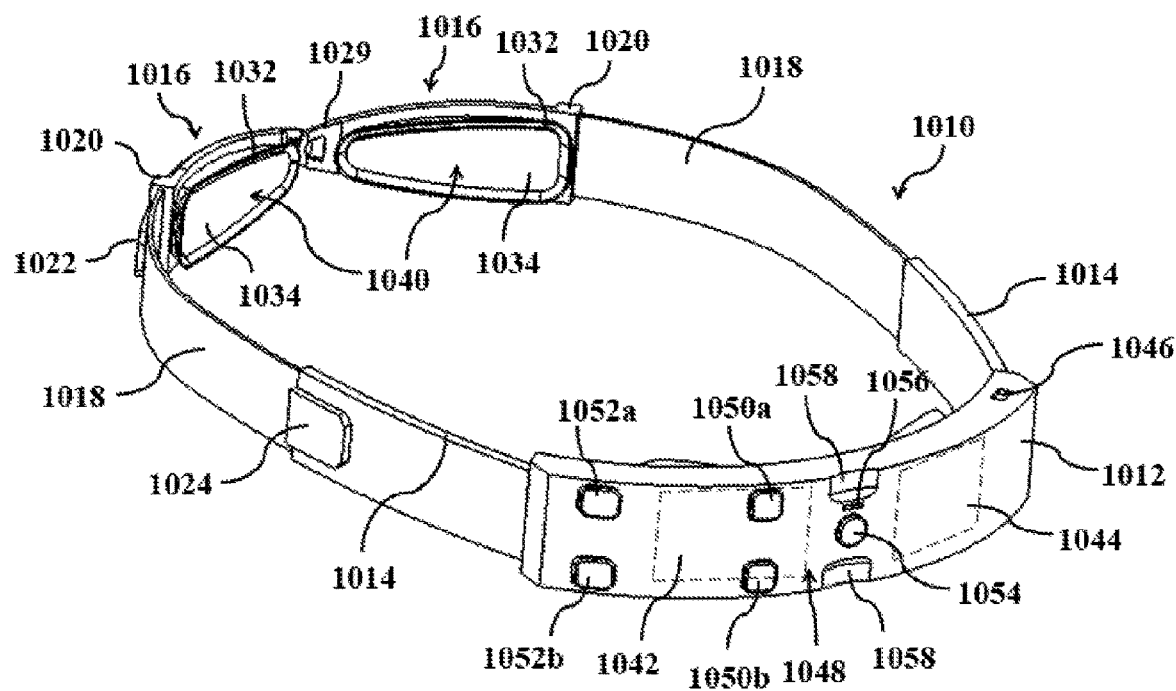

With reference now to the drawings:

FIGS. 1A and 1B are perspective views of an embodiment of an inventive headset according to the teachings herein.

As seen, an inventive headset 1010 according to an embodiment of the teachings herein may be configured to include an anterior member 1012 connected to a pair of flexible arm members 1014, which may also be called interim members, each terminating in a posterior member 1016. Anterior member 1012, flexible arm members 1014, and posterior members 1016 together form the headset body.

In some embodiments, anterior member 1012 is typically at least partially flexible, or at least semi-rigid, and may be formed of plastic or of any other suitable material. The anterior member 1012 is suited to encompass the forehead region of a person, and thus has a curvature generally suited to the shape of a human head.

As described in further detail hereinbelow with reference to FIG. 4, each of arm members 1014 comprises a flexible material, such as polypropylene, polyurethane, or polyethylene. In some embodiments, each arm member 1014 comprises, or has threaded therein a stretchable member 1018, such as an elastic band member, the stretchable member 1018 terminating at the posterior member 1016. The stretchable member 1018 may be formed of any suitable material, including silicone, polyurethane-polyurea copolymer (Lycra®), elastane, neoprene, woven elastic polyester, braided elastic nylon, braided elastic polyester, polyisoprene (synthetic rubber), a stainless-steel spring, and a constant force spring. In some embodiments, stretchable member 1018 comprises a single material and/or a single structure. In some embodiments, stretchable member 1018 comprises multiple materials or structures, as described hereinbelow with reference to FIGS. 24, 25A, and 25B.

In some embodiments, the arm members 1014 comprise semi-rigid portions, so as to properly support the stretchable member 1018 and to allow, in a rest state of headset 1010, anterior member 1012 and posterior members 1016 to form a monolithic and/or integral structure, as described hereinbelow with reference to FIGS. 3A and 3B. Additionally, arm members 1014 are semi-rigid, and not fully rigid, so as to allow the arm members 1014 to conform to the user's head shape and/or to absorb pressure applied to different locations on the arm members without resulting in movement of treating portions of the device, described hereinbelow, from their correct positions. For example, when the user lies down and the side of the user's head is supported, or engages a surface on which the user is lying down, pressure is applied to arm members 1014, and the partial flexibility of the arm members absorbs this pressure and ensures that the treating and/or sensing components of headset 1010 remain properly positioned.

In some embodiments, each posterior member 1016 comprises a semi-rigid member 1020, in some embodiments formed of plastic, and includes a rigid tongue protrusion 1022 which, in a rest state of headset 1010, is housed in a socket 1024 forming part of arm member 1014. In some embodiments, posterior members 1016 further include a size adjustment mechanism 1026, described in further detail hereinbelow with reference to FIGS. 15 and 16. The posterior members 1016 also include a closure mechanism 1028, connected to a tapered end 1029 and described in further detail hereinbelow with reference to FIGS. 17A to 17E.

Anterior member 1012 may be configured to contain, on an interior surface thereof, a pair of anterior electrode systems 1030, and each of posterior members 1016 may be configured to contain, on an interior surface thereof, one or more posterior electrode systems 1040. Each of electrode systems 1030 and 1040 comprises an electrode base 1032 and an electrode pad 1034, structured and functional as described hereinabove with reference to FIGS. 8A, 8B, and 8C. In some embodiments, one or more of electrode systems 1030 and 1040 may comprise trigeminal electrodes, structured and functional as described hereinabove with reference to FIG. 9. In some embodiments, one or more of electrode systems 1030 and 1040 may comprise sensing electrodes, configured to sense at least one electrical parameter of a body portion of said user, such as, for example, electroencephalogram (EEG), skin conductance response (SCR), impedance plethysmograph (IPG), electromyograph (EMG), and the like.

It will be appreciated that headset 1010 may include additional electrodes, as shown in FIGS. 29 to 30B, the additional electrodes having similar structure and/or functionality to those of electrodes 1030 and 1040. It is further appreciated that electrode systems 1030 and/or 1040 may be obviated, or moved to other locations on headset 1010, as suitable for stimulating specific nerves or nerve sets, specific brain regions, or for sensing specific parameters. For example, electrode systems 1040 may be moved to be along the flexible arm members 1014. As another example, the headset 1010 may include only a single pair of electrode systems located on arm members 1014, which electrodes may be configured to be positioned, when the headset is donned, under the hair, while electrode systems 1030 and 1040 may be obviated.

Anterior member 1012 may be configured to contain an electronic circuit 1042, which may be configured to be electrically coupled by conductive wires (not shown) to a power source, such as a battery 1044 and to electrodes systems 1030 and 1040. As described hereinbelow with reference to FIGS. 20A to 22D, in some embodiments, at least a portion of the conductive wires extends to posterior electrode systems 1040 via stretchable member 1018. In some embodiments, the conductive wires may be independently stretchable, without following the structure of the stretchable member 1018 or being embedded therein.

In some embodiments, electronic circuit 1042 and/or battery 1044 may be external to headset 1010, and/or may communicate remotely with headset 1010.

Electronic circuit 1042 may be configured to include a stimulation circuit, a microprocessor, a charging circuit and a user interface as described hereinbelow with reference to FIG. 31.

The stimulation circuit may be configured to produce biphasic, charged balanced electrical pulses, mono-phasic electrical pulses, and/or direct current stimulation.

According to still further features of the described preferred embodiments, the stimulation circuit may be configured to produce electrical stimulation within an intensity range of 0-60 mA, 0-40 mA, 0-20 m, or 0-15 mA.

According to still further features of the described preferred embodiments, the stimulation circuit may be configured to produce stimulation pulses with a duration of 10-600 μsec, 50-500 μsec, 100-500 μsec, 100-450 μsec, 150-400 μsec or 150-450 μsec.

According to still further features of the described preferred embodiments, the stimulation circuit may be configured to produce stimulation pulses at a frequency of 1-500 Hz, 10-300 Hz, 10-250 Hz, 20-180 Hz or 30-180 Hz.

According to still further features of the teachings herein, headset 1010, and specifically electronic circuit 1042, may be suited for applying transcranial electrical stimulation using suitable methods such as Transcranial Direct Current Stimulation (tDCS), Transcranial Alternating Current Stimulation (tACS), and Transcranial Random Noise Stimulation (tRNS), as described hereinabove in the Background section.

Specifically, use of a headset for transcranial electrical stimulation requires a higher depth of penetration of the stimulation current through tissues of the head in order to directly affect brain regions. In order to achieve such deeper current penetration, combinations of electrodes located distantly to one another may be activated simultaneously. For example, an anterior electrode may be activated simultaneously with a posterior electrode. Additionally, the locations of the electrodes may be modified so as to increase the distance between adjacent electrodes, thereby to provide deeper penetration of current.

According to still further features of embodiments of the teachings herein, headset 1010 may be configured to connect to an external electronic circuit and/or stimulation circuit, and thereby to transfer electrical current from an external stimulator to the electrode systems 1030 and/or 1040. In some embodiments, headset 1010 may be configured to connect to at least one external electrode that may be located at various areas of the body. In some embodiments, headset 1010 may be configured to connect to an external electronic circuit and processor in order to transfer signals from sensors disposed on the headset 1010 to the external processor.

In some embodiments, battery 1044 may be disposed within anterior member 1012, and may be recharged by plugging a charger into charging port 1046 located, according to certain embodiments, on anterior member 1012.

Anterior member 1012 may also be configured to include, on an external surface thereof, user controls and interface 1048. That said, in some embodiments, other portions of the inventive headset 1010, such as posterior members 1016 or arms 1014, may be configured to include user interface 1048. In some embodiments, user interface 1048, or an additional user interface (not shown) may be external to headset 1010 and may communicate with headset 1010 remotely, using wired or wireless communication, as explained hereinbelow with reference to FIG. 31.

As explained hereinabove, electronic circuit 1042 and user interface 1048 are configured to control and/or activate electrodes included in headset 1010. In some embodiments, user interface 1048 is configured to control and/or activate at least two, and in some embodiments more than two, pairs of electrodes. As such, in some embodiments, the stimulation circuit and/or user interface 1048 are configured to enable activation of a specific electrode or of a specific pair, or channel, of electrodes, as well as adjustment of the intensity of current supplied by the activated electrodes or of other stimulation parameters of the activated electrodes. In some embodiments, any subset of the electrodes may be activated simultaneously, and in some embodiments specific subsets are predefined, for example during manufacture of the electronic circuit 1042. In some such embodiments, user interface 1048 enables control not only of a specific electrode or of a specific channel, but also of activated subsets of the electrodes.

In some embodiments, user controls and interface 1048 includes a pair of anterior intensity buttons 1050a and 1050b for respectively increasing and decreasing the intensity of stimulation provided by anterior electrode systems 1030, and a pair of posterior intensity buttons 1052a and 1052b for respectively increasing and decreasing the intensity of stimulation provided by posterior electrode systems 1040. It is appreciated that user control and interface 1048 may include similar intensity buttons for each electrode included in the headset 1010.

The user controls and interface 1048 may further include a mode changing button 1054 for activating and disabling the electronic circuit 1042, as well as for changing between modes of operation of headset 1010. For example, headset 1010 may have multiple preset modes of operation, such as a sleep mode, a maintenance mode, and a treatment mode, and repeated operation of button 1054 may switch between these modes, in addition to turning the headset on and off.

An operation indicator 1056, such as an LED light, may form part of user controls and interface 1048 and may be disposed on an exterior surface of anterior member 1012. Indicator 1056 may indicate to a user When the headset 1010 is turned on and/or when the electrode systems 1030 and/or 1040 are active, thereby helping the user prevent unwanted contact with the electrodes when these are operative.

In some embodiments, the user controls and interface 1048 further includes an audio element (not shown), such as a speaker or buzzer, for providing to the user an audible indication of use of the headset 1010, such as an indication of activation of the headset, shutting down of the headset, pressing a button on interface 1048, changing the stimulation mode, and the like.

In some embodiments, the user controls and interface 1048 may further include at least one positioning indicator 1058, for example in the form of notches in the center of anterior member 1012. The positioning indicator 1058 assists the user in donning the headset correctly by providing verification for headset placement, for example by helping the user confirm that the positioning indicator 1058 is aligned with the user's nose.

As seen from comparison of FIGS. 1A and 1B, headset 1010 is longer in the closed state than it is in the rest state, due to extension of stretchable members 1018 in the closed state as described hereinbelow with reference to FIGS. 2A and 2B.

In some embodiments, the circumference of headset 1010 in the closed state, illustrated in FIG. 1B, is not greater than 65 cm, not greater than 63 cm, or not greater than 61 cm. In some embodiments, the circumference of headset 1010 in the closed state, illustrated in FIG. 1B, is not less than 30 cm, not less than 35 cm, or not less than 40 cm. In some embodiments, the length of headset 1010 at rest state, is not more than 95%, not more than 93%, or not more than 91% of the length of the headset at closed state. In some embodiments, the length of headset 1010 at rest state, is not less than 8%, not less than 10%, or not less than 12% of the length of the headset at closed state.

Figure 1C:
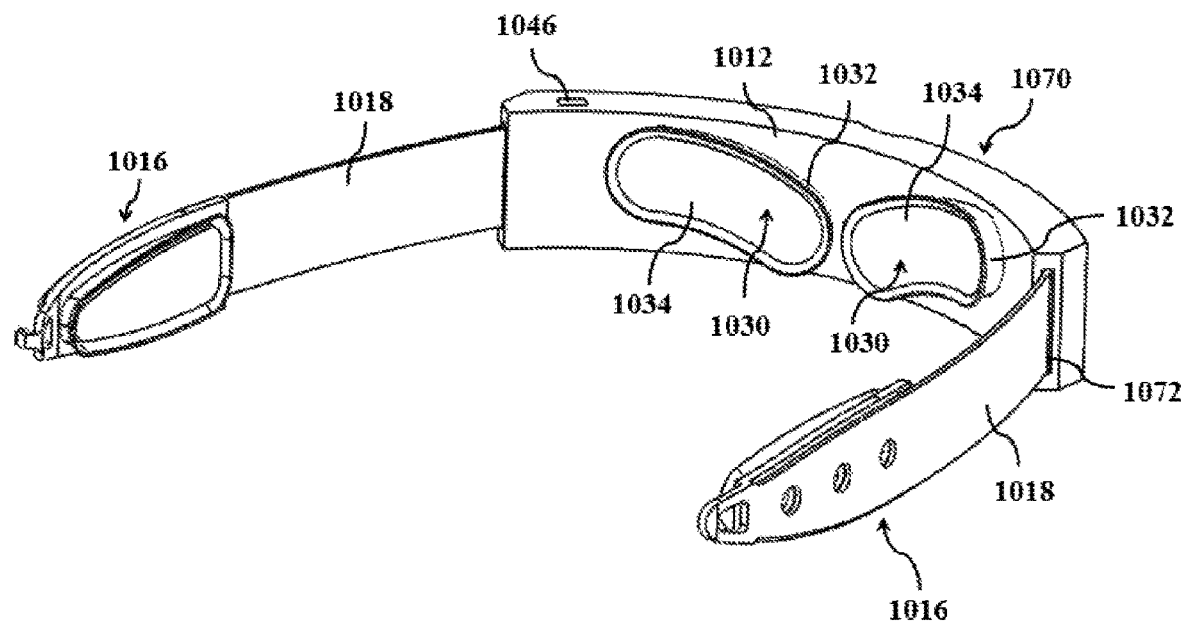
FIGS. 1C and 1D are perspective views of another embodiment of an inventive headset according to the teachings herein.
Figure 1D:
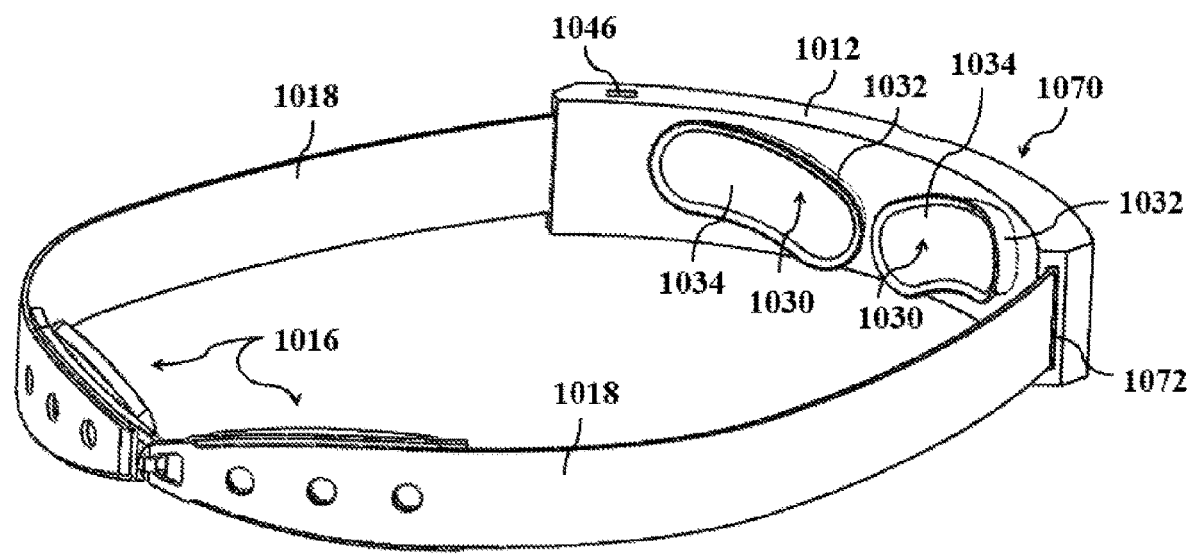

Reference is now made to FIGS. 1C and 1D, which are perspective views of another embodiment of an inventive headset 1070 according to the teachings herein. The headset 1070 of FIGS. 1C and 1D is substantially the same as the headset 1010 of FIGS. 1A and 1B, where like numbers represent like elements.

As seen in FIGS. 1C and 1D, headset 1070 does not include flexible arm members, such as arm members 1014 of FIGS. 1A and 1B, or sockets such as sockets 1024 of FIGS. 1A and 1B. Consequently, stretchable members 1018 of FIGS. 1C and 1D do not include a rigid tongue protrusion such as protrusion 1022 of FIGS. 1A and 1B.

In headset 1070, each stretchable member 1018 extends directly out of slots 1072 in anterior member 1012, and terminates in a posterior member 1016.

Due to the omission of flexible arm members 1014, tongue protrusion 1022 and socket 1024, the stretchable members 1018 are not supported during donning of the headset 1070 as described hereinbelow with reference to FIGS. 3A to 3E. Thus, in order to ensure proper placement of anterior member 1012 during donning headset 1070, the user may find it more convenient to don the headset while anterior member 1012 is supported by other means. For example, the user may lay down on his back in a supine position or extend his head backward, such that the anterior member 1012 is supported by the user's forehead, or may lay down facing forward with his forehead directed towards the ground or another surface, such that the anterior member 1012 is supported against the forehead by the surface on which the user is lying down.

Figures 2A, 2B:
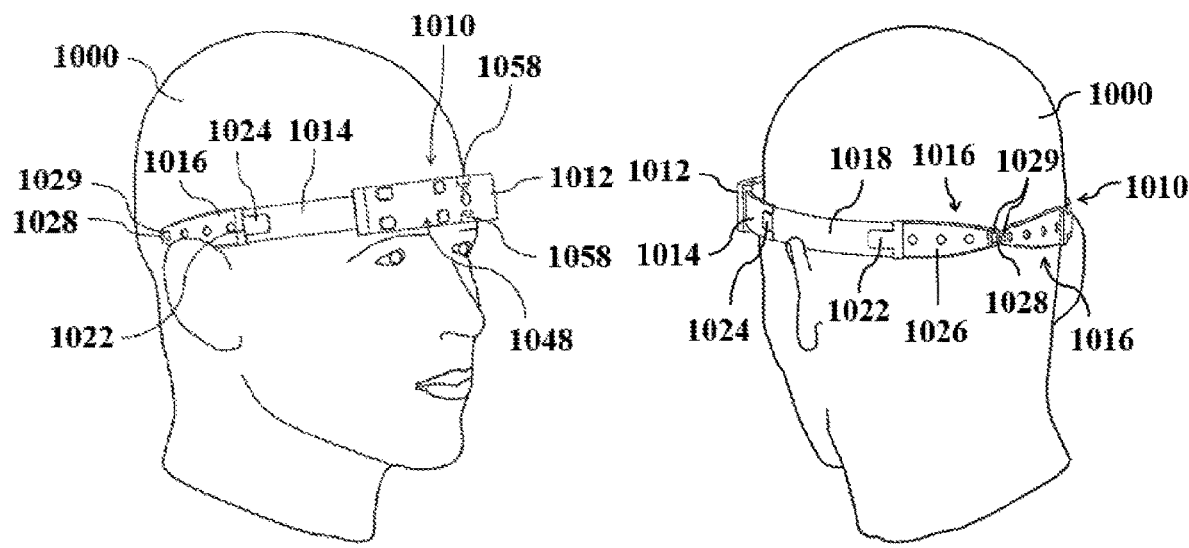
FIGS. 2A and 2B are perspective views of the inventive headset of FIGS. 1A and 1B, positioned on a head of a user.

Reference is now made to FIGS. 2A and 2B, which are perspective views of the inventive headset of FIGS. 1A and 1B, positioned on a head of a user. Reference is also made to FIGS. 3A, 3B, 3C, 3D, and 3E which provide perspective views of steps of a method of donning the inventive headset of FIGS. 1A and 1B on a head of a user.

Figure 3A:
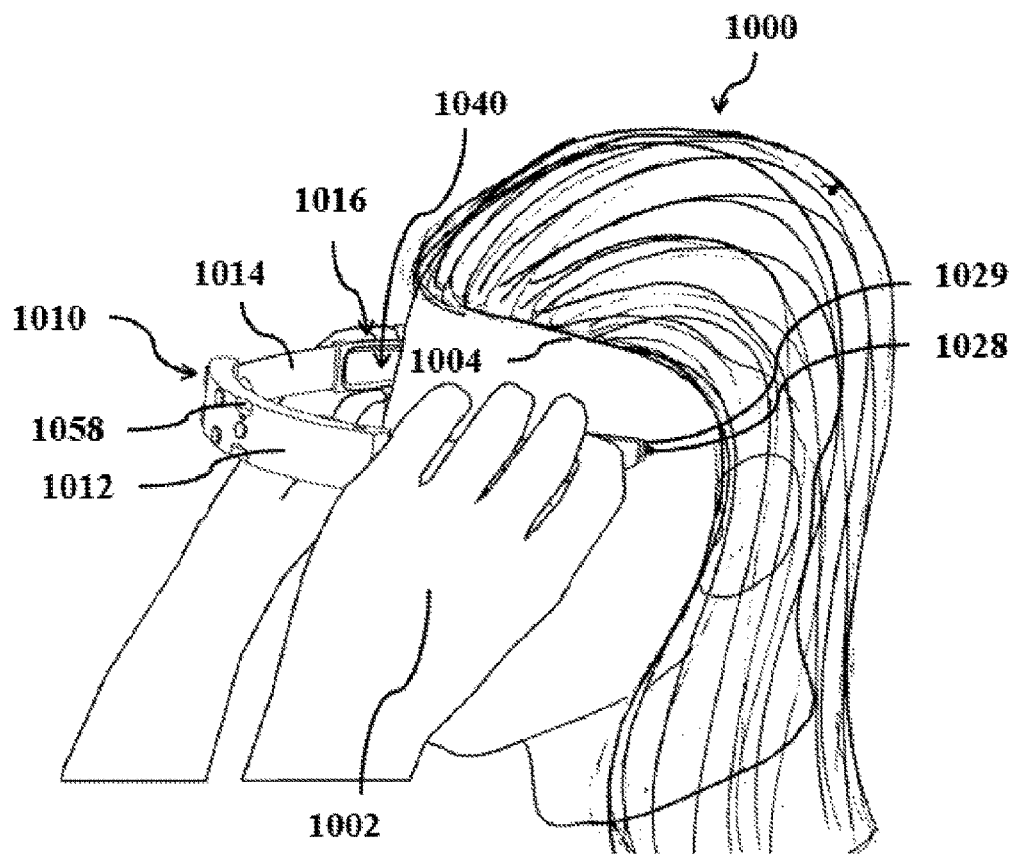
FIGS. 3A, 3B, 3C, 3D, and 3E provide perspective views of steps of a method of donning the inventive headset of FIGS. 1A and 1B on a head of a user.

As seen in FIG. 3A, in an initial step of donning headset 1010, the user holds the headset with fingers 1002, such that anterior member 1012 is in close proximity to a forehead of a head 1000 of the user. As seen, fingers 1002 hold the headset 1010 at posterior members 1016, typically holding a plastic portion of the posterior members so as to ensure the safety of the user. For example, the user may hold posterior members 1016 at dedicated, electrically insulating, grips such as those described in further detail hereinbelow with reference to FIGS. 18A and 18B.

As seen with particular clarity in FIG. 2A, it is a particular feature of the teachings herein that during this initial donning step of the headset 1010, rigid tongue 1022 of posterior member 1016 is disposed within tongue socket 1024 of the corresponding arm member 1014, thereby ensuring that posterior members 1016 remain aligned with arm members 1014 and with anterior member 1012, forming a single monolithic and/or integral unit, and that the anterior member 1012 does not "droop" relative to the arm members 1014. Such construction allows the user to ensure proper positioning of anterior member 1012 of the headset 1010 on head 1000 even without holding onto the anterior member. Additionally, the user holds headset 1010 at posterior members 1016, which are at the end of stretchable members 1018, so as to more readily enable rearward pulling of the stretchable members 1018 while closing the headset as described hereinbelow.

It is another particular feature of the teachings herein that the posterior member 1016 terminates in tapered end 1029, to which is connected to closure mechanism 1028. As such, when the user holds posterior members 1016 adjacent to the temples, closure mechanism 1028 lies adjacent to the hairline 1004, and tapered end 1029 can, during donning of the headset 1010, plow through and/or under the hair to ensure that posterior electrodes 1040, and in some embodiments any other electrodes located along arm members 1014 and/or along stretchable members 1018, lie against the scalp of the user, with no hair interference.

Figure 3B:
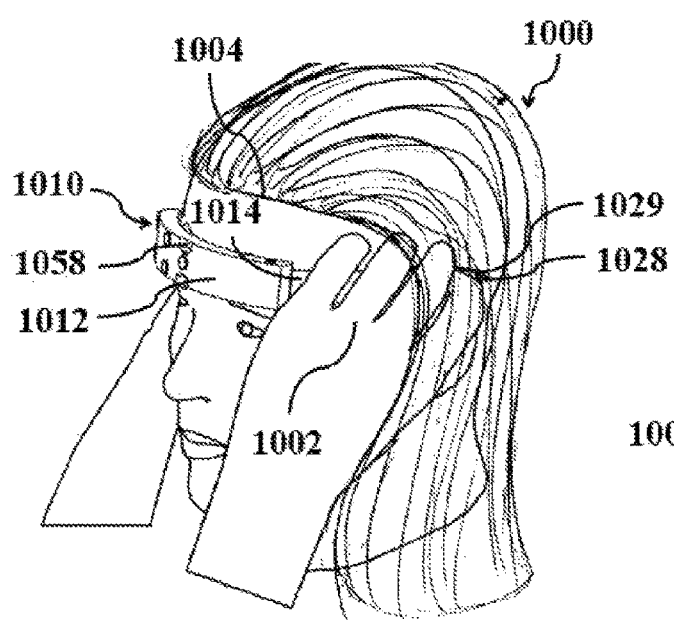

Turning additionally to FIG. 3B, it is seen that the user places the headset 1010 with the anterior member 1012 touching the forehead of the user, such that closure mechanism 1028 and tapered end 1029 plow through the hair and the posterior members 1016 are disposed above the user's ears. Symmetrical placement of both posterior members 1016 above the ears ensures centered placement of anterior member 1012 on or adjacent to the user's forehead and correct circumferential and longitudinal placement of electrodes located on headset 1010, when the headset is fully donned. The rigid tongue 1022 is still disposed in socket 1024 so that the anterior member 1012, arm members 1014, and posterior members 1016 form a monolithic and/or integral unit, and are aligned and do not droop one relative to the other. The user may make sure that headset 1010 is properly positioned on his head by ensuring that the positioning indicators 1058 are longitudinally aligned with the nose bridge.

It is a particular feature of the present invention that, in some embodiments, positioning indicators 1058 comprises notches or other tactilely distinguishable features on anterior member 1012, enabling the user to verify the positioning of indicators 1058 by feeling the indicators simultaneously with feeling a centered part of his or her face, such as the nose bridge, without requiring visual assistance of a mirror or another person.

Figure 3C:
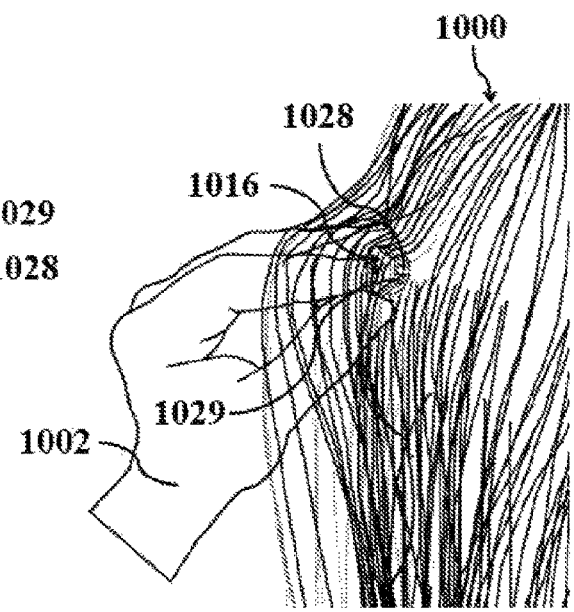

FIG. 3C shows the fingers 1002 holding posterior member 1016 and pulling it rearward, while tapered end 1029 plows through the hair and maintains close proximity to the surface of the scalp so as to enable direct contact between the posterior electrodes and the scalp. As seen, the hair drapes over the posterior member 1016 while tapered end 1029 plows between the roots of the hair on the surface of the scalp.

Figure 3D:
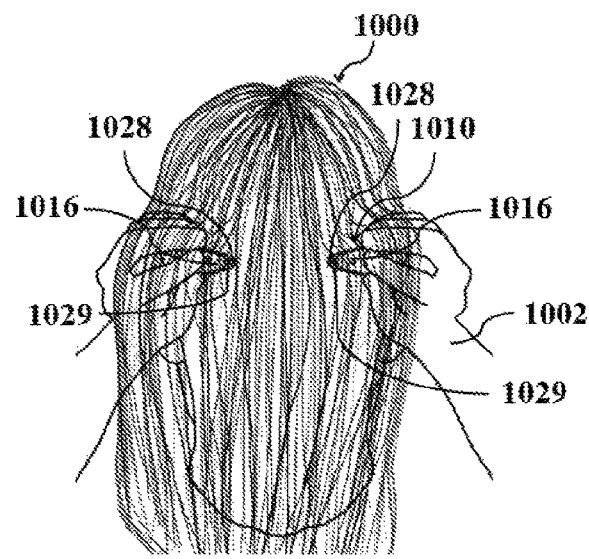

FIG. 3D shows the user's head 1000 from the rear, showing that closure mechanism 1028 and tapered end 1029 continue to plow through the hair. As the user pulls posterior members 1016 towards the back of the head in order to close the closure mechanism 1028, stretchable members 1018 extend out of arm members 1014, in some embodiments under the hair, such that rigid tongue 1022 exits socket 1024, as seen in FIG. 3BB. The stretchable members 1018 apply radial pressure to the head during donning of the headset 1010, thereby ensuring that the anterior member 1012 remains in position, with the anterior electrode systems touching the user's forehead.

Figure 3E:
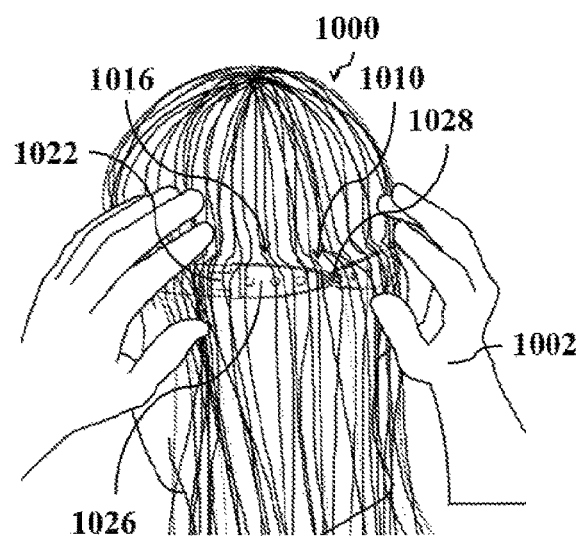

In FIGS. 2B and 3E, headset 1010 is fully donned on the user's head 1000, and closure mechanism 1028 is closed at the rear of the user's head. Anterior member 1012 engages the user's forehead such that the anterior electrode systems engage the user's skin in the area of, and may stimulate, the supraorbital and supratrochlear nerves bilaterally. The posterior electrode systems of posterior members 1016 engage the user's scalp, below the hair, at the rear of the user's head in the area of the occipital nerves, and may stimulate these nerves. Stretchable members 1018 apply radial pressure on anterior member 1012 and on posterior members 1016 pushing them toward the user's head, thereby ensuring that the anterior and posterior electrode systems maintain their suitable positions and remain in close contact with the user's skin. As described hereinabove, in some (non-illustrated) embodiments, additional electrode systems may be used to stimulate other nerves or nerve junctions, such as the zygomaticotemporal nerve and the auriculotemporal nerve, or to transcutaneously stimulate brain regions such as the frontal, occipital, parietal and temporal lobes, or sonic electrodes may comprise sensing electrodes configured to sense electrical parameters of a portion of the user's head. Additionally, due to extension of stretchable member 1018 out of flexible arm members 1014, rigid tongue 1022 is no longer situated within socket 1024.

Figure 4:
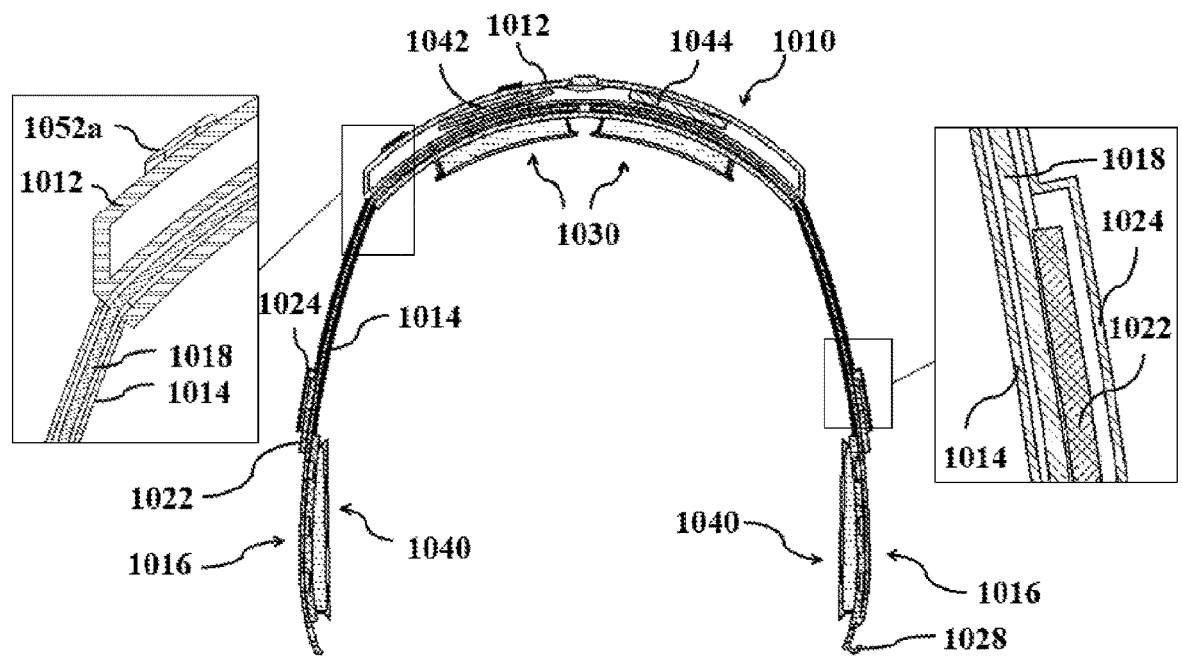
FIG. 4 provides a sectional view of the inventive headset of FIGS. 1A and 1B, in a rest state.
Figure 5:
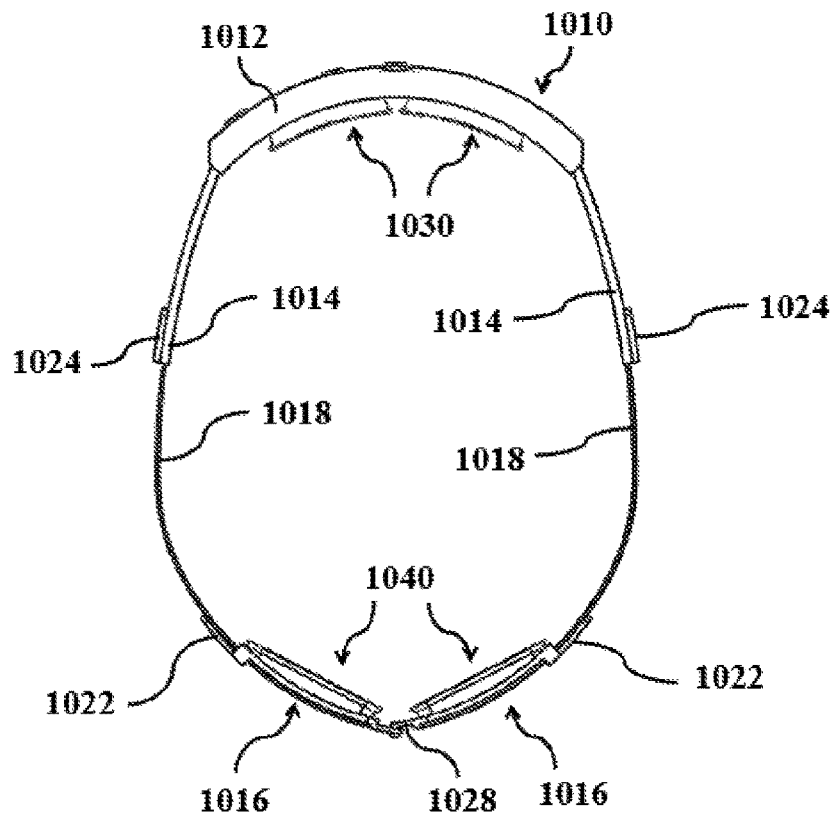
FIG. 5 provides a top plan view of the inventive headset of FIGS. 1A and 1B, in a closed state.

Reference is now made to FIG. 4, which provides a sectional view of the inventive headset of FIGS. 1A and 1B, in a rest state, and to FIG. 5, which provides a top plan view of the inventive headset of FIGS. 1A and 1B, in a closed state.

FIG. 4 shows headset 1010 in the rest position, in which closure mechanism 1028 is open, and stretchable members 1018 are disposed within arm members 1014 and extend through the arm members 1014, as well as along a portion of the anterior member 1012, as described in further detail hereinbelow with reference to FIGS. 23 and 24. As seen, in the rest state of headset 1010, rigid tongue 1022 is disposed within socket 1024, thereby ensuring that posterior members 1016 and arm members 1014 function, while in rest state, as a monolithic and/or integral unit, and generally do not move vertically relative to one another.

As seen in FIG. 5, closure mechanism 1028 is closed, such that the circumference of headset 1010 is sufficient to surround the entirety of the user's head. In the closed state shown in FIG. 4, stretchable member 1018 extends out of arm members 1014, such that rigid tongue 1022 exits socket 1024, and posterior members 1016 are movable vertically relative to anterior member 1012. As described hereinabove, in the closed state of headset 1010 electrodes 1030 and 1040 are positioned such that, when donned, they are appropriately placed to stimulate target nerves and/or brain regions as described hereinabove with reference to FIGS. 2B, 3E, 30A, and 30B.

Figure 6:
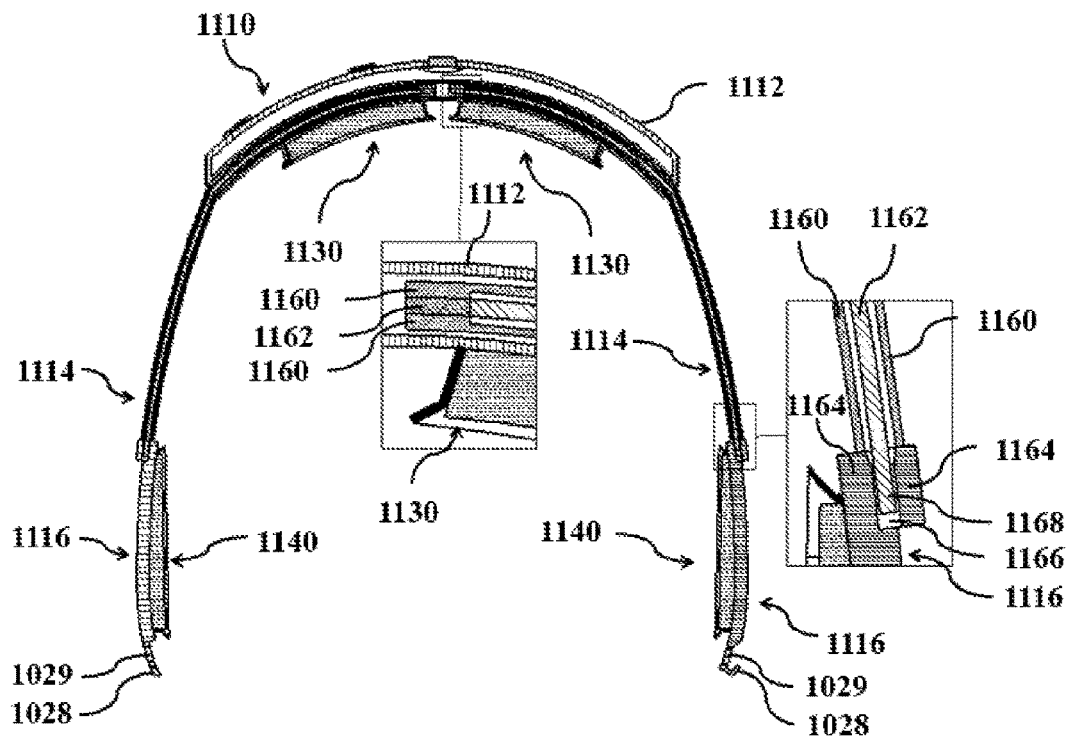
FIGS. 6 and 7 provide sectional views of another embodiment of an inventive headset according to the teachings herein, in a rest state and in a closed state, respectively.
Figure 7:
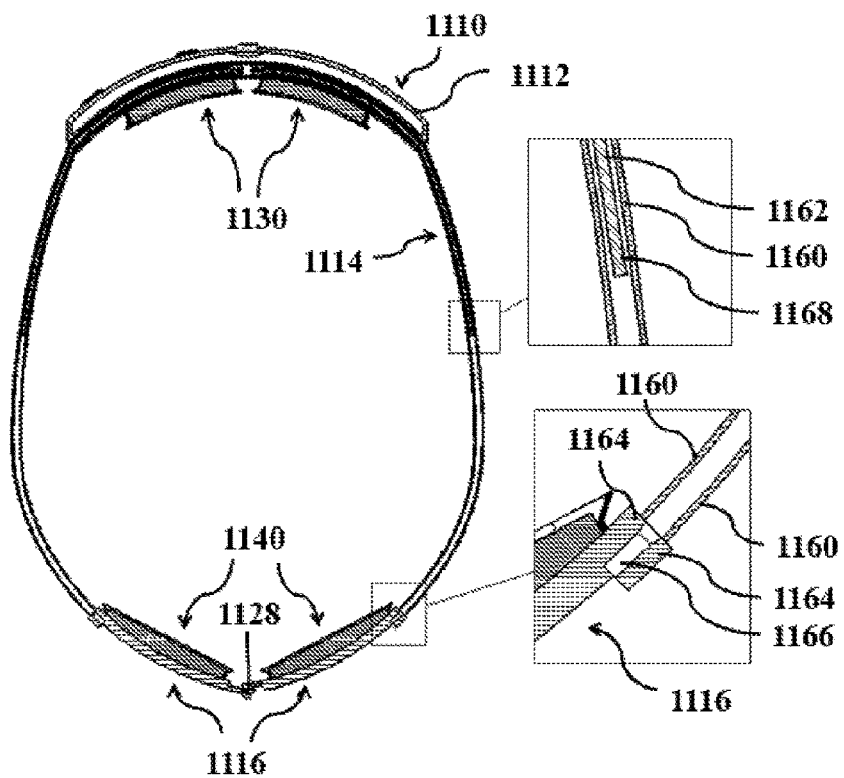

Reference is now made to FIGS. 6 and 7, which provide sectional views of another embodiment of an inventive headset according to the teachings herein, in a rest state and in a closed state, respectively.

As seen in FIG. 6, a headset 1110 is similar to headset 1010 of FIGS. 1A and 1B, where like numbers indicate like portions. Headset 1110 includes an anterior member 1112 having mounted thereon a pair of electrode systems 1130, and posterior members 1116 each having mounted thereon an electrode system 1140 and terminating at a tapered end 1129 having mounted thereon a portion of a closure mechanism 1128 for closing headset 1110 around the user's head.

A pair of flexible arm members 1114, disposed between anterior member 1112 and posterior members 1116, each include a stretchable, or elastic, sleeve portion 1160, for example formed of silicone, polyurethane-polyurea copolymer (Lycra®), elastane, neoprene, woven elastic polyester, braided elastic nylon, braided elastic polyester, and polyisoprene (synthetic rubber). Sleeve portion 1160 has a semi-rigid core 1162 passing therethrough and providing support to the sleeve portion 1160, the core being fabricated from a flexible material such as polypropylene, polyurethane, polyethylene, and stainless steel. Sleeve portion 1160 and core 1162 are attached to one another at one end thereof located within anterior member 1112, and, in some embodiments, are also attached to anterior member 1112, for example to a body portion thereof. At the other end thereof, each sleeve 1160 is connected to a wall portion 1164 of posterior member 1116 surrounding a slot 1166 within the posterior member 1116.

It is a particular feature of the present embodiment of the teachings herein that, as seen clearly in the enlarged portion of FIG. 6, when headset 1110 is in the rest state, an end 1168 of core 1162 is disposed within slot 1166 of posterior member 1116, thereby ensuring that posterior members 1116 and arm members 1114 function, while in rest state, as a monolithic and/or integral unit, and generally do not move vertically relative to one another.

Turning to FIG. 7, it is seen that closure mechanism 1128 is closed, such that the circumference of headset 1110 is sufficient to surround the entirety of the user's head. In the closed state shown in FIG. 7, stretchable sleeve portion 1160 extends further than core 1162, such that end 1168 of core 1162 exits socket 1166 of posterior member 1116, and posterior members 1116 are movable vertically relative to anterior member 1112. As described hereinabove, in the closed state of headset 1110 electrodes 1130 and 1140 are positioned such that, when donned, they are appropriately placed to stimulate target nerves and/or brain regions as described hereinabove with reference to FIGS. 2B, 3E, 30A, and 30B.

Figure 8A:
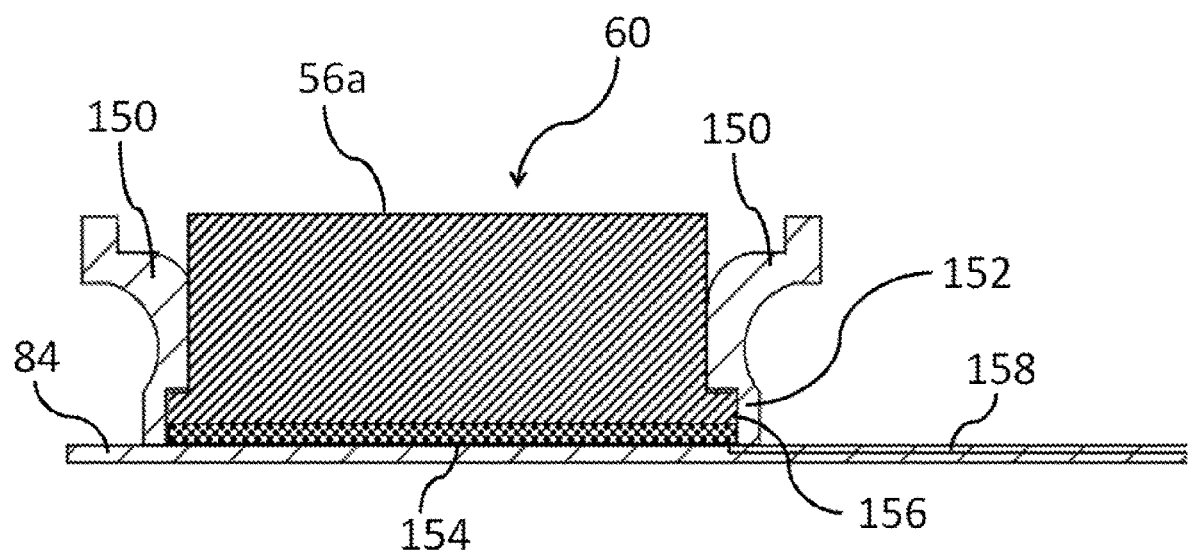
FIG. 8A is a cross-sectional view of an electrode pad disposed an electrode base.

FIG. 8A is a cross section of an electrode pad 56a disposed in an electrode base 60, the combination of electrode pad and electrode base being suitable for use in headsets as described herein, for example as electrodes 1030 and/or 1040. Electrode base 60 may be configured to be physically coupled to a headset, such as headset 1010, by elongated flexible connecting band 84 and may be electrically coupled to the headset electrical circuit, such as circuit 1042 (FIG. 1A), by conductive wire 158. Electrode base 60 may be configured to include at leak one electrode base housing 150 which includes elevated circumferential walls surrounding a "floor", thereby creating a cavity adapted to receive at least one conductive electrode pad 56a. According to certain embodiment, electrode base housing 150 is preferably made of a flexible material such as silicon or thermoplastic polyurethane (TPU).

Electrode base housing 150 may be configured to include an electrically conductive material 154 disposed at least partially above, or within electrode base housing 150 floor. The conductive layer is adapted to be electrically coupled to an electric circuit by electrical conductor 158.

Conductive layer 154 may be configured to include material such as stainless steel, copper, brass, silicone carbon, conductive silver paint print, stainless mesh or other conducting elements. When conductive layer 154 is made of carbon, an additional layer of conductive paint may be printed on its bottom surface. Such a conductive paint layer may improve the homogeneity of current distribution across the surface of conductive layer 154 and thereby improve the homogeneity of current distribution on the surface of electrode pad 56a. Conductive layer 154 may preferably be flexible in order to not compromise the overall flexibility of electrode base 60 and thereby to ensure its alignment with various head contours. In certain embodiments, conductive layer 154 may be limited in its area and may be configured to cover only a portion of the floor surface of electrode base housing 150. In such a case, conductive layer 154 may not be flexible and may be made of various electrically conductive materials known to those of skill in the art. Conductive layer 154 may be configured to be electrically coupled to an electrical conductor (cable or wire) 158 and thereby be electrically connected to the headset electrical circuit.

Electrode pad 56a may be configured to be releasably coupled (physically and electrically) to electrode base housing 150. Electrode pad 56a may include at least a portion of water or other liquid absorbing material such as non-woven fabric, felt or sponge. When coupled to housing 150, electrode pad 56a is configured to be in electrical contact with conductive layer 154. When the headset is donned, pad 56a is urged toward the skin surface and may create electrical contact with the skin surface (skin surface including the scalp) in order to transfer electrical current to the skin surface.

In some embodiments, the electrode pad 56a may be provided to the user dry, and the user may soak electrode pad 56a with water, saline, conductive gel, or other suitable liquid before use. In other embodiments, the electrode pad 56a may be pre-soaked with conductive gel, such that the gel is mostly absorbed in the pad, and the user need not soak the pad at all. The conductive gel may be any commercially available conductive gel suitable for use with electrodes. It is appreciated that use of conductive gel improves conductivity and reduces dehydration of the pad 56a, and that pre-soaked pads 56a may be easier and less messy for the user to handle.

Electrode pad 56a and other electrodes associated with the headset may be configured to receive (sense) electrical current or other bio-signals from the skin surface, such as for example electroencephalogram (EEG) and either transfer it via the headset circuit to an electronic circuit that includes a microprocessor or transmit it wirelessly to a remote unit.

Electrode pad 56a may be disposable and may be conveniently replaced by the user.

Electrode pad 56a may be configured to include a peripheral edge 156 that is thinner than the central area of pad 56a. Peripheral edge 156 can be made by various manufacturing process such as ultrasonic welding, RF welding or heat compression. By inserting the thin edge 156 into a corresponding groove 152 in housing 150, electrode pad 56a can be reversibly physically coupled to housing 150 and electrically coupled to conductive layer 154.

Electrode pad 56a may be configured to have larger area compared to housing 150. It can therefore be squeezed into housing 150 in order to be reversibly (physically an electrically) coupled to housing 150.

Electrode base housing 150 may be configured to include a conducting mechanical snap connector configured to be both physically and electrically reversibly coupled to a corresponding connector attached to electrode pad 56a.

Figure 8B:
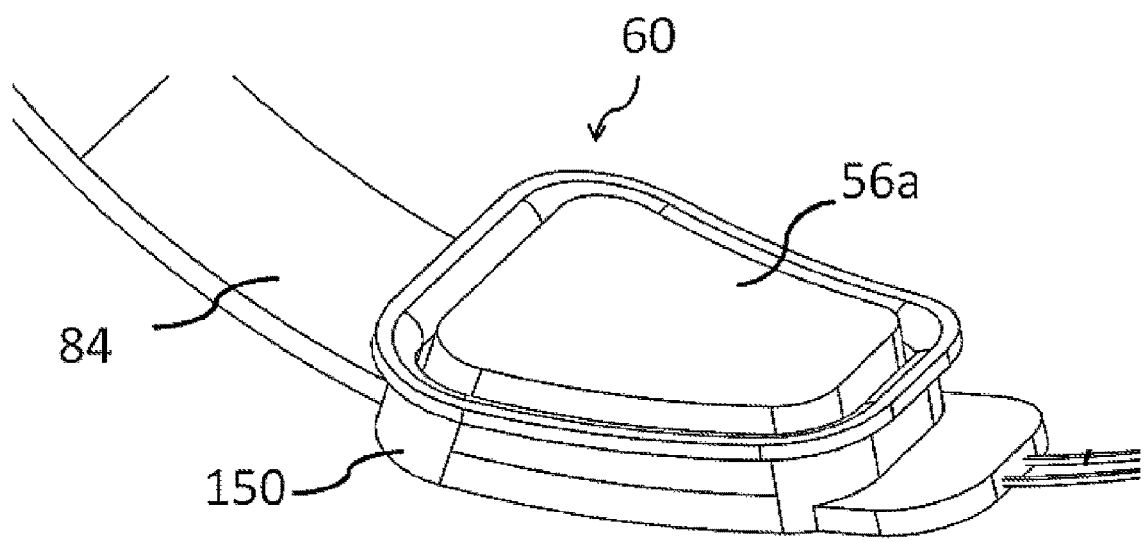
FIGS. 8B and 8C provide perspective views of an electrode base with (FIG. 8B) and without (FIG. 8C) a multi-layered electrode pad, according to the present invention.
Figure 8C:
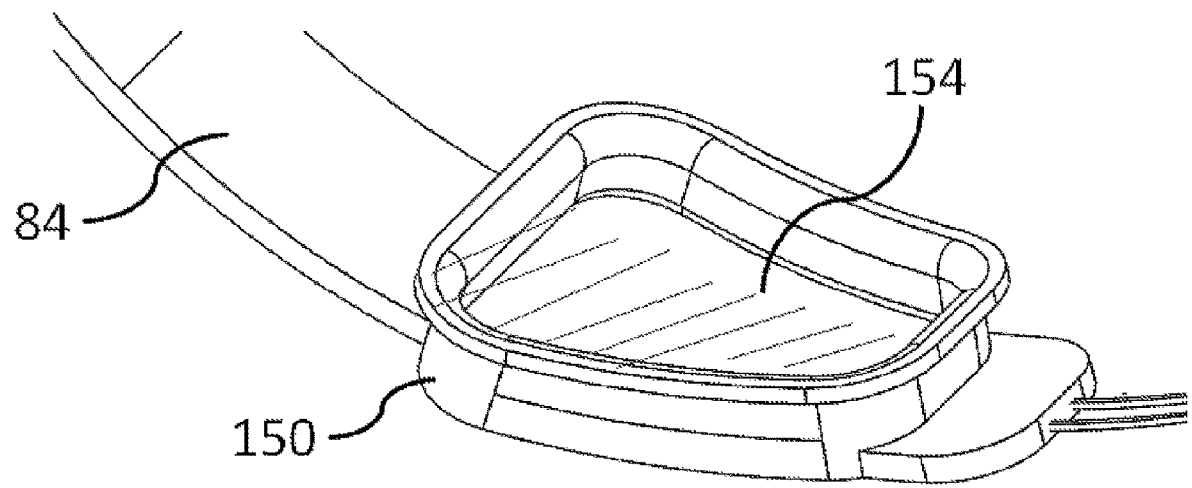

Perspective views of an electrode base 60 with and without an inventive, multi-layered electrode pad 56a are provided in FIG. 8B and FIG. 8C.

Additional Electrode configurations are described in PCT Application Publication Number WO2014/141213, entitled "HEADSET FOR TREATMENT AND ASSESSMENT OF MEDICAL CONDITIONS", which is hereby incorporated by reference as if fully set forth herein.

Figure 9:
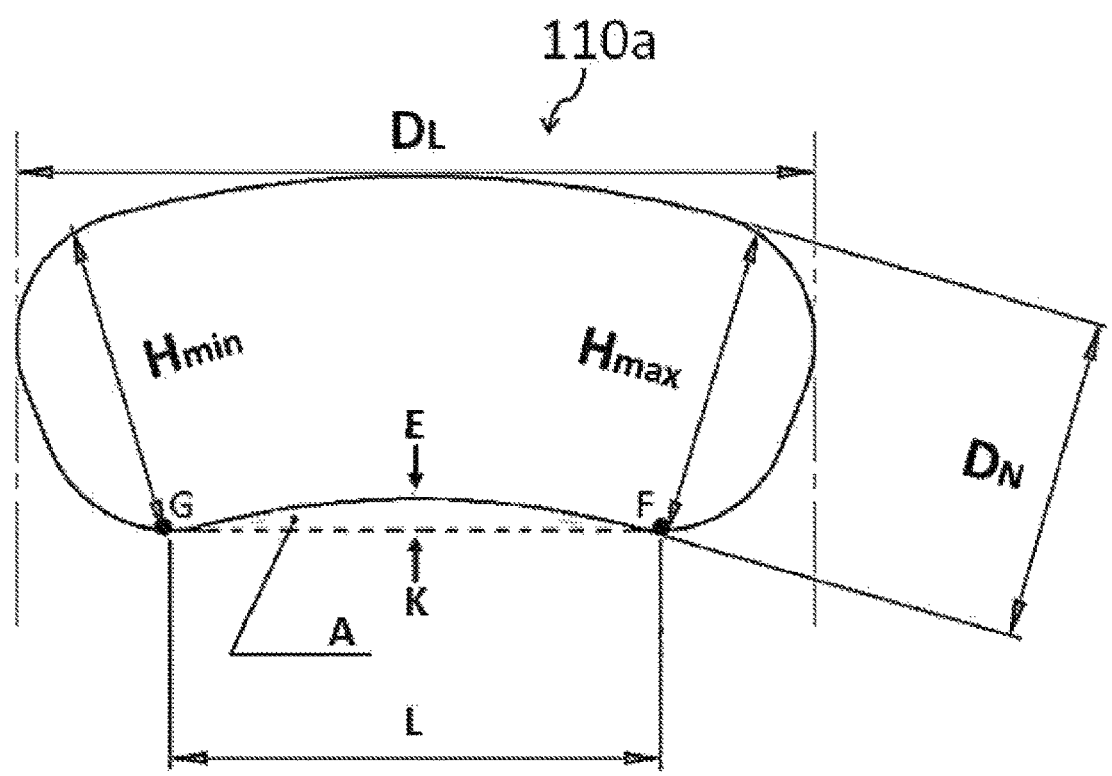
FIG. 9 provides the dimensions of an inventive electrode configured to selectively stimulate nerve branches in the supraorbital region.

FIG. 9 is an illustration of an embodiment of electrode 110a which electrode may be configured for stimulation of the supraorbital region, such as one or more of electrodes 1030 and 1040 of FIGS. 1A and 1B. Electrode 110a may include a biocompatible conducting material configured to face the skin surface, and may be configured to include an electrode backing attached to a conductive contact surface. The backing may contain at least one conductive material or element that may be electrically coupled with the conductive contact surface.

Electrode 110a may be configured to have a conductive contact surface with the following dimensions:
  (i) a long dimension ($D_L$) having a length of 20 mm to 55 mm, 25 to 50 mm, or 30 to 45 mm.
  (ii) a narrow dimension ($D_N$) having a length of 10 mm to 30 mm, 10 to 25, or 12 to 20 mm.

Concave contour E has a concavity defined by boundary points G and F, which points are disposed at opposite ends of the concavity.

Typically, A/L is at least 0.5 mm,
  A being an area bounded by dotted line K and the concavity;
  L being a length of line K (between boundary points G and F), (L) being at least 10 mm,
wherein a line disposed between a first point on the concave contour and a second point on the perimeter of electrode 110a, on a side opposite to concave contour E, and aligned in perpendicular fashion with respect to contour E at the first point, has a length H, and wherein, over an entirety of the concave contour, $$H_{max}/H_{min} \leq 2.5$$

$H_{max}$ being a maximum value of H over this entirety; and
$H_{min}$ being a minimum value of H over this entirety.

The distance between two electrodes configured to stimulate the supraorbital region may be in a range of 5-45 mm, 8-35 mm, or 8-25 mm. Additional electrodes may be located on the headset in order to stimulate other nerves, for example, the zygomaticotemporal nerve or the auriculotemporal nerve. The headset may also include electrodes that are configured to stimulate the occiput region.

Reference is now made to FIGS. 10A and 10B, which are side plan views of posterior member 1016, including tapered end 1029 and closure mechanism 1028, of the inventive headset 1010 of FIGS. 1A and 1B, in a rest state and in a hair plowing state, respectively.

FIG. 10A shows posterior member 1016 as well as closure mechanism 1028 and tapered end 1029 of posterior member 1016. As seen, in some embodiments, during the rest state, the tapered end 1029 and the portion of closure mechanism 1028 connected thereto are pointed downward relative to a horizontal axis of posterior member 1016. Such positioning of tapered end 1029 provides a pre-load position for plowing, which ensures that while plowing under the hair layers tapered end 1029 maintains contact with the scalp, thereby ensuring that posterior member 1016 and the posterior electrode systems 1040 and/or any other electrodes that are to be positioned below the hair of the user will be in physical and/or electrical contact with the skin of the scalp, and will not be obstructed by layers of hair.

Turning to FIG. 10B, during donning of headset 1010 when posterior member 1016 and tapered end 1029 are plowing through the hair of the user, tapered end 1029 and the portion of closure mechanism 1028 connected thereto are substantially aligned with a horizontal axis of posterior member 1016, and are pointed higher than during the rest state, due to a tangential force applied by the user's fingers pushing posterior members 1016 rearward. When headset 1010 is donned on the user's head, a similar force is applied by stretchable members 1018.

Reference is now made to FIGS. 10C and 100, which are schematic top plan and side plan views of a posterior member of an inventive headset suitable for plowing through the hair according to the teachings herein, such as posterior members 1016 of headset 1010. It is appreciated that FIGS. 10C and 10D are described with respect to posterior member 1016 of headset 1010, but are equally applicable to other embodiments described herein and to additional embodiments not explicitly described.

As seen in FIG. 10C, in some embodiments, posterior member 1016 is tapered, such that the width of the posterior member 1016 at the end which is connected to the stretchable member 1018, indicated by A, is greater than the width of the posterior member 1016 at the open end of headset 1010 adjacent closure mechanism 1028, indicated by A', such that A>A'. In other embodiments, not illustrated herein, the width of posterior member 1016 may be fixed throughout the length thereof, such that A=A'. The narrow, and preferably tapered, structure of posterior member 1016 allows the posterior member 1016 to effectively plow under and/or through the hair and between the roots of the hair in order to reach the scalp surface while pushing the hair away from under the posterior member 1016 and electrodes associated therewith and/or disposed at locations where hair is present.

In some embodiments, the width A of posterior member 1016 at its widest point is not greater than 40 mm, not greater than 30 mm, or not greater than 20 mm. In some embodiments, the length of posterior member 1016, indicated by L, is not greater than 100 mm, not greater than 80 mm, not greater than 60 mm, or not greater than 50 mm. In some embodiments, the length of posterior member 1016, indicated by L, is not less than 5 mm, not less than 10 mm, or not less than 20 mm.

It is appreciated that in embodiments in which posterior member 1016 has an electrode system disposed thereon, such as that illustrated in FIGS. 1A and 1B, the dimensions of the posterior member 1016 must be sufficiently large to house the electrode system, and therefore are restricted by the minimal electrode dimensions. In embodiments in which no electrode is disposed on the posterior member 1016, any suitable dimensions may be used, and the dimensions may be determined based on other parameters, such as ease of use when donning the headset, effectiveness of the posterior member in plowing away the hair, and the like.

It is further appreciated that in some embodiments, such as embodiments in which posterior member 1016 includes an electrode system, the tapering of the width of posterior member 1016 need not be linear along the length of the posterior member, and/or the posterior member need not be tapered along the entirety of its length. For example the posterior member may include an electrode portion having a fixed width or tapering very slightly, and may taper at a greater angle in a second portion, distal to the electrode, to reach width A' at the closure mechanism.

Turning to FIG. 10D, it is seen that in some embodiments, the thickness of the posterior member 1016 may be tapered, such that the thickness of the posterior member 1016 at the end which is connected to the stretchable member 1018, indicated by B is greater than the thickness of the posterior member 1016 at the open end of headset 1010 adjacent closure mechanism 1028, indicated by B', such that B>B'. In other embodiments, not illustrated herein, the thickness of posterior member 1016 may be fixed throughout the length thereof, such that B=B'. The low profile, and preferably tapered structure of posterior member 1016 allows the posterior member 1016 to effectively plow under and/or through the hair and between the roots of the hair in order to reach the scalp surface while pushing the hair away from under the posterior member 1016 and electrodes associated therewith and/or disposed at locations where hair is normally present.

In some embodiments, the thickness of posterior member 1016 at its thickest point B is not greater than 25 mm, not greater than 20 mm, or not greater than 15 mm. In some embodiments, the thickness of posterior member 1016 at its thinnest point B' is not greater than 25 mm, not greater than 15 mm, not greater than 10 mm, or not greater than 5 mm.

In some embodiments, the posterior member 1016 is semi-rigid, and has an internal surface which, when the headset 1010 is fully donned, obtains a curvature R corresponding to the curvature of the scalp of the user while stretchable members 1018 apply radial pressure onto posterior member 1016 toward the user's head.

As described hereinabove with reference to FIGS. 3A to 3E, it is a particular feature of the teachings herein that the posterior member 1016, and particularly the tapered end 1029, is designed to plow through the hair of the user during donning of headset 1010, so as to ensure that posterior electrode systems 1040 and/or additional electrode systems directly engage the skin of the scalp, and are not obstructed by layers of hair. As such, posterior member 1016, and specifically tapered end 1029 thereof, are sufficiently rigid so as not to bend or warp due to the force applied by the hair and the scalp during plowing therethrough.

Reference is now made to FIGS. 11A and 11B, which provide top plan views of inventive headset of FIGS. 1A and 1B in a rest state, in an open and a folded position, respectively. FIG. 11A shows headset 1010 in an open position and in rest state, as described hereinabove with reference to FIG. 4. In the rest state, headset 1010 has a width dimension W in the range of 50-180 mm, in the range of 80-160 mm, or in the range of 100-140 mm, and a first length dimension L1 in the range of 70-220 mm, in the range of 100-200 mm, or in the range of 120-180 mm.

FIG. 11B shows headset 1010 in rest state and in a folded position, where arm members 1014 are folded so as to lie generally parallel to anterior member 1012, in a similar manner to that in which eyeglasses fold. Any suitable type of hinge mechanism (not illustrated) may be used for folding arm members 1014, such as a spring hinge, a barrel hinge, an interlocking hinge, and an integrated hinge built into arm members 1014. Further, the hinge mechanism may be formed of any suitable type of material, including plastic and metal such as stainless steel.

It is a particular feature of the teachings herein that in the folded position, headset 1010 has a second length dimension L2 in the range of 20-100 mm, in the range of 30-85 mm, or in the range of 40-70 mm, making the headset easy to transport, for example in a suitable case similar to an eyeglasses case. In some preferred embodiments, the second length dimension L2 is not more than 50% of first length dimension L1, not more than 40% of L1, not more than 30% of L1, and even not more than 20% of L1.

Reference is now made to FIGS. 12A and 12B, which are a perspective view and a front plan view of anterior member 1012 of the inventive headset 1010, including an embodiment of a size adjustment mechanism according to the teachings herein.

As seen in the illustrated embodiment, anterior member 1012 includes a slide and lock size adjustment mechanism, comprising, on each of the top and bottom surfaces of anterior member 1012, a pair of tracks 1210, the tracks including multiple pairs of fixation points 1212. Each pair of fixation points 1212 includes a first fixation point disposed on a top surface of anterior element 1012 and a second fixation point disposed on a bottom surface of anterior element 1012, the first and second fixation points being longitudinally aligned.

A pair of semi rigid band support elements 1214 are disposed within anterior member 1012, and may be generally planar or may be slightly curved to match the curvature of anterior member 1012. The band support elements 1214 are connected to ends of a stretchable element within the anterior member 1012, such as to ends of stretchable members 1018 shown in FIG. 4 or to ends of stretchable sleeve 1160 shown in FIG. 6. Each band support element 1214 is connected to a pair of sliding buttons 1216, movable within tracks 1210 between fixation points 1212.

For size adjustment of the headset, the user presses buttons 1216 and moves them within track 1210, thereby moving band support elements 1214, and changing the length of the stretchable element attached thereto. For example, when the user moves buttons 1216 from fixation points 1212c, located near the center of anterior member 1012, to fixation points 1212b or 1212a, located closer to the ends of anterior member 1012, band support elements 1214 are respectively moved further towards the ends of anterior member 1012. Due to the fact that band support elements 1214 are attached to the stretchable members 1018, movement of band support elements 1214 causes movement of the ends of stretchable members 1018 closer to the ends of anterior member 1012, resulting in a longer portion of the stretchable members located outside of the anterior member 1012 and contributing to the circumference of headset 1010, thus enlarging the circumference of the headset.

Figure 13A:
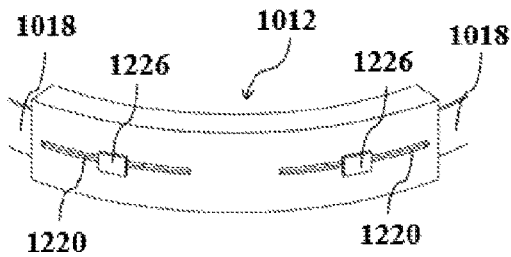
FIGS. 13A and 13B are a perspective view and a front plan view of an anterior member of the inventive headset of FIGS. 1A and 1B, including another embodiment of a size adjustment mechanism according to the teachings herein.
Figure 13B:
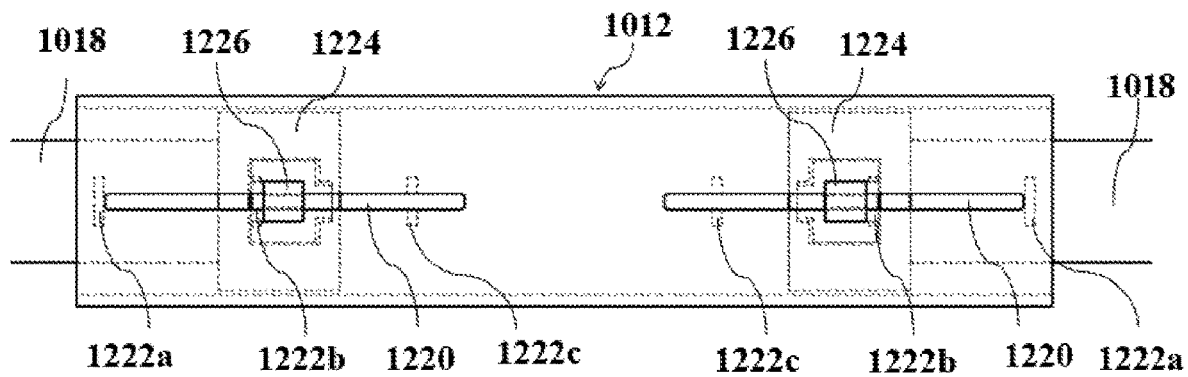

FIGS. 13A and 13B are a perspective view and a front plan view of anterior member 1012 of the inventive headset 1010, including another embodiment of a size adjustment mechanism according to the teachings herein.

As seen in the illustrated embodiment, anterior member 1012 includes a slide and lock size adjustment mechanism, comprising, on a forward facing surface of anterior member 1012, a pair of tracks 1220, each track including multiple fixation points 1222.

A pair of semi rigid band support elements 1224 are disposed within anterior member 1012, and may be generally planar or may be slightly curved to match the curvature of anterior member 1012. The band support elements 1224 are connected to ends of a stretchable element within the anterior member 1012, such as to ends of stretchable members 1018 shown in FIG. 4 or to ends of stretchable sleeve 1160 shown in FIG. 6. Each band support element 1224 is connected to a sliding button 1226, movable within tracks 1220 between fixation points 1222.

For size adjustment of the headset, the user presses buttons 1226 and moves them within tracks 1220, thereby moving band support elements 1224, and changing the length of the elastic element attached thereto. For example, when the user moves buttons 1226 from fixation points 1222c, located near the center of anterior member 1012, to fixation points 1222b or 1222a, located closer to the ends of anterior member 1012, band support elements 1224 are respectively moved further towards the ends of anterior member 1012. Due to the fact that band support elements 1224 are attached to the stretchable members 1018, movement of band support elements 1224 causes movement of the ends of stretchable members 1018 closer to the ends of anterior member 1012, resulting in a longer portion of the stretchable members located outside of the anterior member 1012 and contributing to the circumference of headset 1010, thus enlarging the circumference of the headset.

Figure 14A:
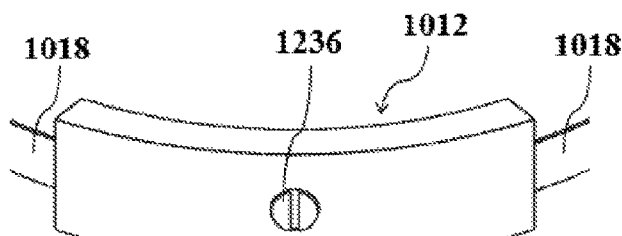
FIGS. 14A and 14B are a perspective view and a front plan view of an anterior member of the inventive headset of FIGS. 1A and 1B, including a further embodiment of a size adjustment mechanism according to the teachings herein.
Figure 14B:
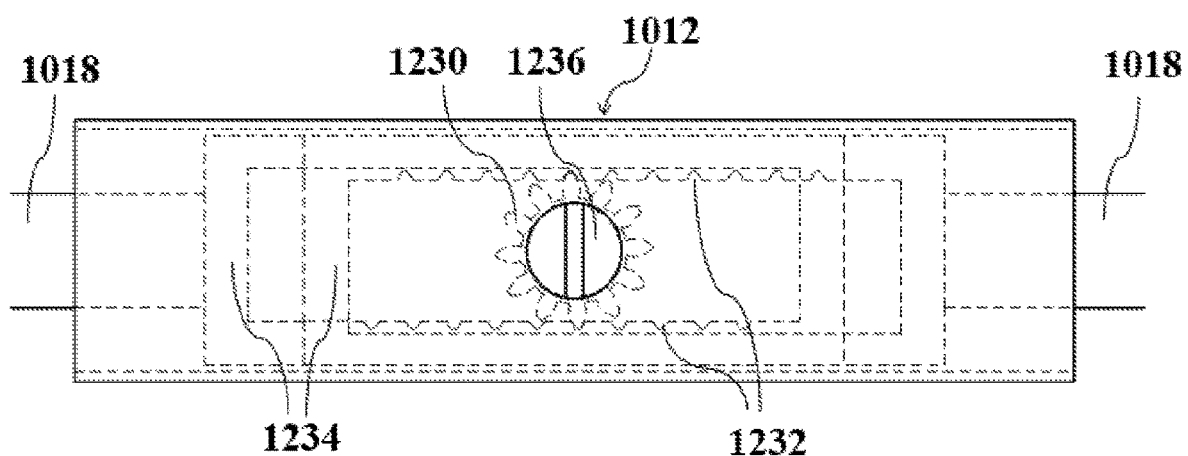

Reference is now made to FIGS. 14A and 14B, which are a perspective view and a front plan view of anterior member 1012 of the inventive headset 1010 including a further embodiment of a size adjustment mechanism according to the teachings herein.

As seen in the illustrated embodiment, anterior member 1012 includes a cogwheel size adjustment mechanism, similar to that of a bicycle helmet. The cogwheel mechanism comprises a cogwheel 1230 disposed within anterior member 1012, and controllable by a screw 1236 disposed in a bore on a forward facing surface of anterior member 1012. Cogwheel 1230 engages serrated surfaces 1232 of a pair of semi rigid band support elements 1234, which are disposed within anterior member 1012 and which may be slightly curved to match the curvature of anterior member 1012. Band support elements 1234 are connected to ends of an elastic element within the anterior member 1012, such as to ends of stretchable members 1018 shown in FIG. 4 or to ends of stretchable sleeve 1160 shown in FIG. 6.

For size adjustment of the headset, the user rotates screw 1236, thereby rotating cogwheel 1230, causing motion of serrated surfaces 1232 and of band support elements 1234, and changing the length of the stretchable member attached thereto. For example, when the user rotates screw 1236 clockwise, resulting rotation of cogwheel 1230 causes band support elements 1234 to be respectively moved further towards the ends of anterior member 1012. Due to the fact that band support elements 1234 are attached to the stretchable members 1018, movement of band support elements 1234 causes movement of the ends of stretchable members 1018 closer to the ends of anterior member 1012, resulting in a longer portion of the stretchable members located outside of the anterior member 1012 and contributing to the circumference of headset 1010, thus enlarging the circumference of the headset.

Figure 15:
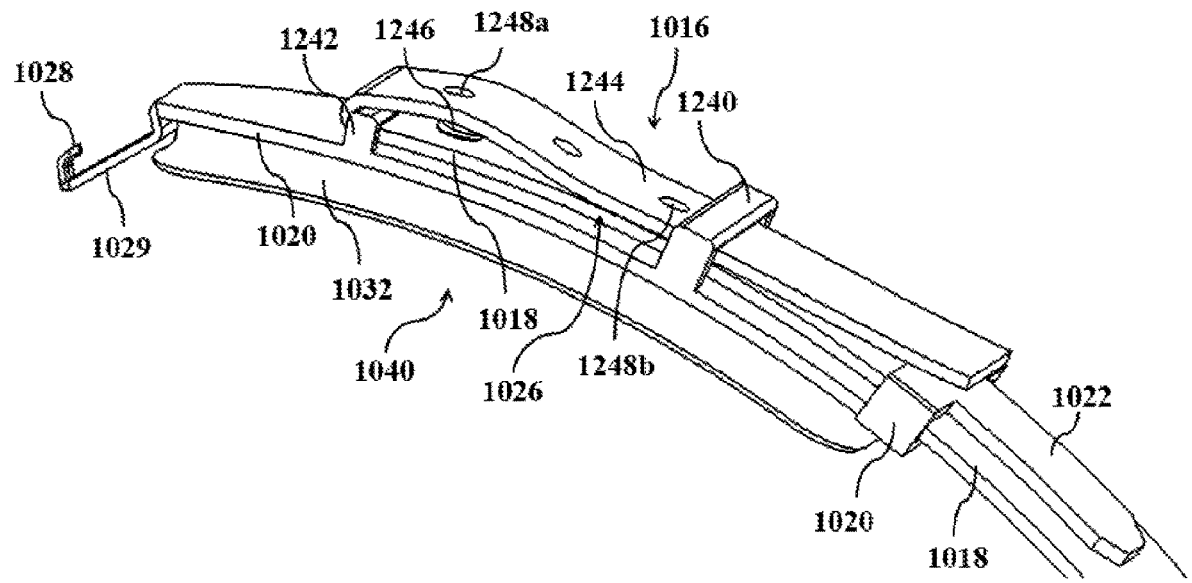
FIG. 15 is a perspective view of a posterior member of the inventive headset of FIGS. 1A and 1B, including an embodiment of a posterior size adjustment mechanism according to the teachings herein.

Reference is now made to FIG. 15, which is a perspective view of posterior member 1016 of the inventive headset 1010, including an embodiment of a posterior size adjustment mechanism 1026 according to the teachings herein.

As seen, posterior member 1016 may include a looping over size adjustment mechanism 1026. In such embodiments, semi-rigid member 1020 of posterior member 1016 extends along the entire length of posterior member 1016 from rigid tongue 1022 to tapered end 1029, typically lying above electrode system 1040. In some embodiments, stretchable member 1018 or a narrower extension thereof extends below rigid tongue 1022 along semi-rigid member 1020, under a first bridge 1240 and under a second bridge 1242 both forming part of semi-rigid member 1020.

One of a plurality of apertures 1248 in stretchable member 1018 or in the extension thereof, engages a pin 1246 forming part of semi-rigid member 1020, thereby securing the stretchable member 1018 to semi-rigid member 1020. The specific aperture 1248 engaging pin 1246 defines the length of stretchable member 1018 available as part of the circumference of headset 1010. The excess 1244 of stretchable member 1018, disposed distally to the aperture 1248 engaging pin 1246 and not included in the circumference of headset 1010, may be looped around second bridge 1242 and secured under first bridge 1240 so as to prevent the excess strap from flapping around, bothering the user, or getting caught on surrounding items.

To adjust the size of headset 1010, the user releases stretchable member 1018 from semi-rigid member 1020 by disengaging the aperture 1248 from pin 1246. The user may then moves stretchable member 1018 so that another aperture 1248 corresponds to pin 1246, and may place that aperture 1248 around pin 1246 securing stretchable member 1018 to semi-rigid member 1020, thereby changing the length of the portion of stretchable member 1018 which is contributing to the circumference of headset 1010. For example, in order to enlarge the circumference of the headset 1010, the user changes the aperture 1248 engaging pin 1246 from a more proximal aperture, such as aperture 1248*a* to a more distal aperture, such as aperture 1248*b*, thereby extending the section of stretchable member 1018 contributing to the circumference of the headset, and shortening the excess portion 1244.

Figure 16:
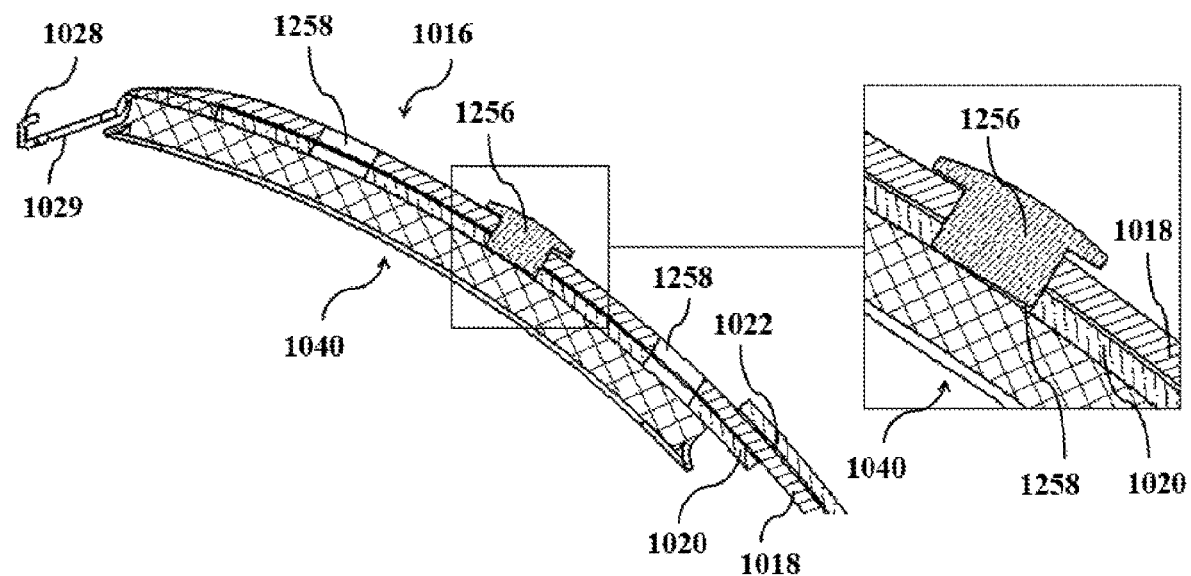
FIG. 16 is a schematic sectional view of a posterior member of the inventive headset of FIGS. 1A and 1B, including another embodiment of a posterior size adjustment mechanism according to the teachings herein.

FIG. 16 is a sectional view of posterior member 1016 of the inventive headset 1010 of FIGS. 1A and 1B, including another embodiment of posterior size adjustment mechanism according to the teachings herein.

As seen, posterior member 1016 may include an elastic size adjustment mechanism, wherein the elastic length of stretchable members 1018 changes, but the physical length of the stretchable member 1018 forming part of the circumference of headset 1010 does not change. In such embodiments, stretchable member 1018 extends along the entirety of semi-rigid member 1020 of posterior member 1016, from rigid tongue 1022 to tapered end 1029, typically lying above semi-rigid member 1020 and electrode system 1040 in a fixed position relative to semi-rigid member 1020.

A pin 1256, disposed in one of a plurality of apertures 1258 in stretchable member 1018 and in corresponding location in semi-rigid member 1020, secures the stretchable member 1018 to semi-rigid member 1020. The specific placement of pin 1256 defines the elastic length of stretchable member 1018, without changing the physical length of stretchable member 1018 available as part of the circumference of headset 1010, and without changing the relative positioning between the stretchable member 1018 and the semi-rigid member 1020.

To adjust the size of headset 1010, the user moves pin 1256 to another aperture 1258, thereby changing the elastic length of stretchable member 1018 that may be stretched while donning headset 1010, without changing the rest-state circumference of the headset. For example, in order to allow a user with a larger head to comfortably don headset 1010 without increasing the radial force applied to the user's head, the user may move pin 1256 to a more distal aperture 1258, thereby enabling a greater portion of stretchable member 1018 to be stretched while donning the headset 1010.

It is appreciated that other mechanism may be used for fixing the elastic length of stretchable member 1018, as well as for fixing stretchable member 1018 to semi-rigid member 1020, all of which mechanisms are considered to be in the scope of the teachings herein.

Reference is now made to FIGS. 17A, 17B, 17C, 17D, and 17E which are perspective views of five embodiments of closure mechanism 1028 of headset 1010 of FIGS. 1A and 1B.

Figure 17A:
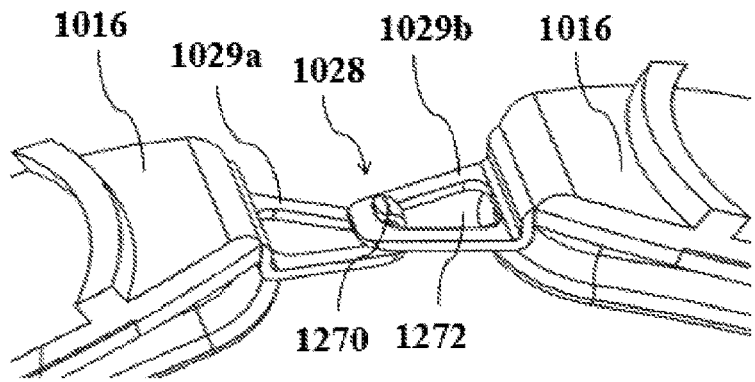
FIGS. 17A, 17B, 17C, 17D, and 17E are perspective views of five embodiments of a closure mechanism for closing the inventive headset of FIGS. 1A and 1B according to the teachings herein.

FIG. 17A shows a hook-and-eye based closure mechanism 1028. As seen, the tapered end 1029*a* of one posterior member 1016 comprises a hook 1270, while the other tapered end 1029*b* is hollowed out and forms a loop, or eye 1272, for the hook to be caught on. When the user dons the headset 1010, the user slides tapered end 1029*b* over tapered end 1029*a*, and then releases. The hook 1270 gets caught in loop 1272, and then headset 1010 is closed and secure around the user's head. The headset 1010 remains secure around the user's head due to the pulling force applied by stretchable members 1018.

Figure 17B:
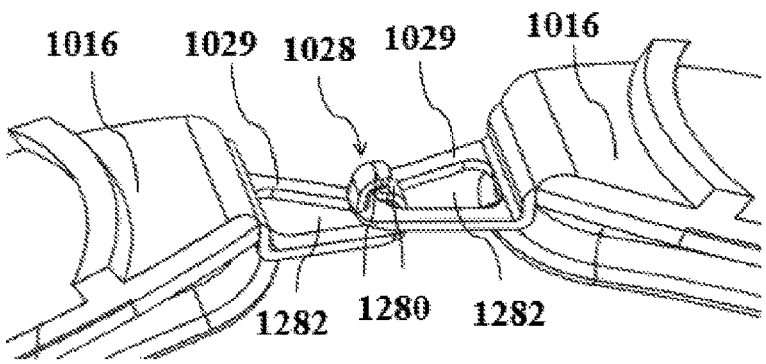

One disadvantage of the embodiment of FIG. 17A is that it is directional, and requires the user to remember which side includes the loop and should be slipped over the side that includes the hook in order to secure the headset 1010. This disadvantage may be overcome by the embodiment illustrated in FIG. 17B, in which the hook-and-eye closure mechanism 1028 is bidirectional. As seen in FIG. 17B, the tapered end 1029 of each of posterior members 1016 includes, at its distal end, a hook 1280, as well as a hollow loop 1282 proximal to the hook 1280. When donning headset 1010, the user need not worry about the direction in which the tapered ends 1029 overlap each other. The user may pull either tapered end 1029 over the other, such that the hook 1280 disposed on the lower tapered end 1029 will get caught in the loop 1282 of the higher tapered end 1029, and the headset 1010 will be secured on the user's head.

Figure 17C:
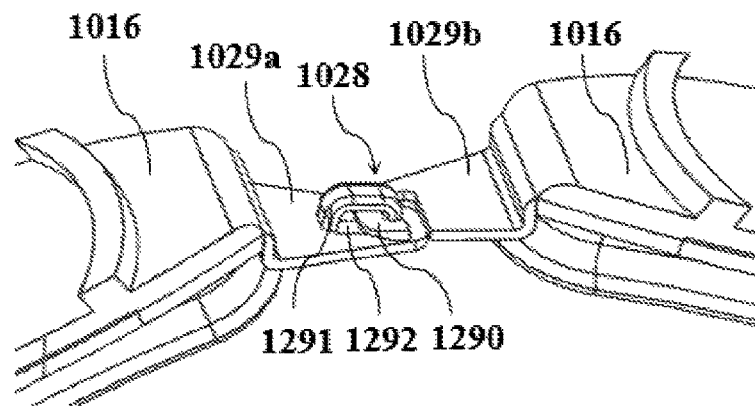

FIG. 17C illustrates another type of hook-and-eye closure mechanism 1028, in which the latching occurs vertically rather than horizontally. As seen, a tapered end 1029*a* of one of posterior members 1016 includes a protruding bridge 1291 forming a hollow loop 1292 thereunder, while the tip of the other tapered end 1029*b* is shaped as a hook 1290. When donning headset 1010, the user may raise tapered end 1029*b* vertically above tapered end 1029*a*, and slide hook 1290 downward into loop 1292.

Figure 17D:
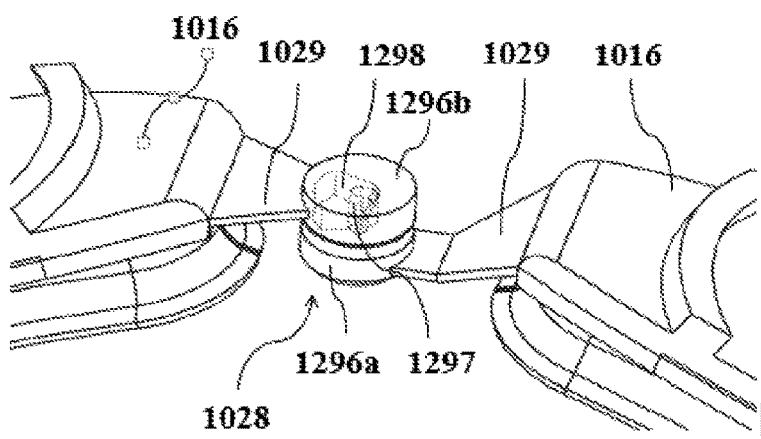

FIG. 17D illustrates a closure mechanism 1028 based on use of a magnet. As seen, each of tapered ends 1029 of posterior members 1016 terminates in a magnet portion 1296. One magnet portion 1296*a* includes a pin 1297, whereas the other magnet portion 1296*b* includes a bore 1298 suitable for housing pin 1297. Magnet portions 1296 are arranged so as to attract one another When disposed adjacent one another, thereby directing pin 1297 to engage bore 1298 and to secure the headset on the user's head. In some embodiments, not shown in FIG. 17D, the magnets 1296 may lie generally perpendicular to tapered ends 1029, such that there is no need to overlap the magnets one over the other in order to secure the pin 1297 in bore 1298. In some embodiments, the magnets comprise Neodymium magnets.

Figure 17E:
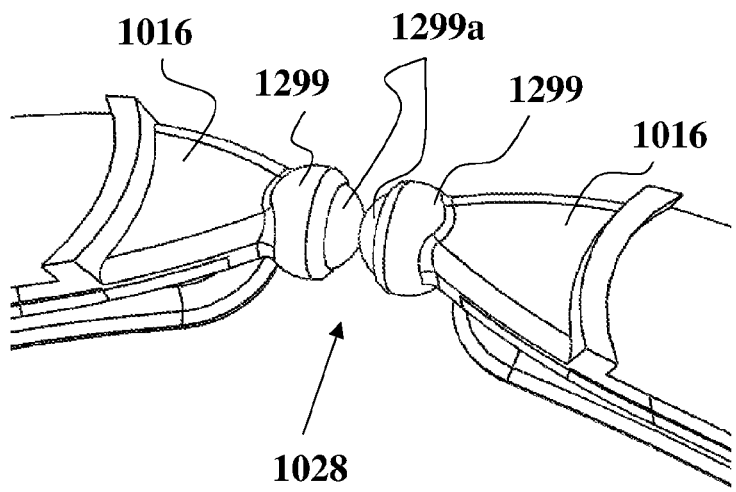

FIG. 17E illustrates another closure mechanism 1028 based on use of a magnet. As seen, each of tapered ends 1029 of posterior members 1016 terminates in a magnet housing 1299, housing a magnet 1299*a* comprising at least a section of a sphere defining at least one spherical surface. In some embodiments, the magnets 1299*a* comprise a section of a sphere, such as a spherical cap or half a sphere. In other embodiments, the magnets 1299*a* comprise a sphere. In some embodiments, the spherical surface of the magnets 1299*a* has a radius in the range of 2 to 20 mm, in the range of 3 to 15 mm, or in the range of 4-10 mm. In some embodiments the holding force of magnets 1299*a* is in the range of 0.5 to 15 N, in the range of 1 to 10 N, or in the range of 1.5 to 7 N.

Magnets 1299*a* are adapted to engage one another at the spherical surface thereof, thereby to close headset 1010. Due to the spherical shape of the engagement surface of magnets 1299*a*, the contact point between the two magnets 1299*a* is minimal and is substantially a single point, thereby preventing pinching of the user's hair within the closure mechanism 1028.

In some embodiments, magnets 1299*a* are rotatable within magnet housing 1299 and are arranged so as to attract one another when disposed at a small distance from one another so as to make it easier for the user to close the headset 1010 while donning the headset, without seeing the closure mechanism 1028, as explained hereinabove with reference to FIGS. 3A to 3E In some embodiments, the magnets are arranged so as to attract one another when they are at a distance not greater than 10 mm, not greater than 20 mm, or not greater than 30 mm. Furthermore, due to the magnets' ability to rotate within magnet housing 1299, the polar orientation of the magnets may adjust itself to an optimal orientation or alignment between the two magnets at a given alignment of or angle between posterior members 1016. In some embodiments, the magnets comprise Neodymium magnets.

It will be appreciated that any suitable closure mechanism may be used for securing headset 1010 so that it does not fall or move when donned. However, it is a particular feature of the teachings herein that in all of the embodiments illustrated in FIGS. 17A to 17E, the footprint of closure mechanism 1028, and specifically the footprint of surfaces of closure mechanism 1028 that contact each other when the closure mechanism is closed, is small, thereby reducing, and in some cases even preventing, hair from being caught in and/or pulled by elements of the closure mechanism 1028 while closing the headset on the user's head.

Figure 18A:
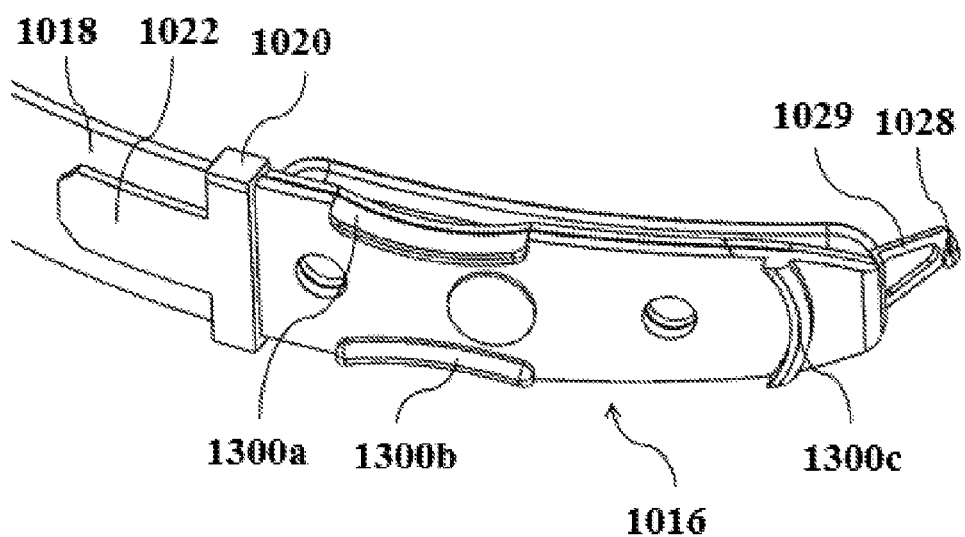
FIGS. 18A and 18B are perspective views of two embodiments for enabling a user to more easily grip a posterior member of inventive headsets according to the teachings herein.
Figure 18B:
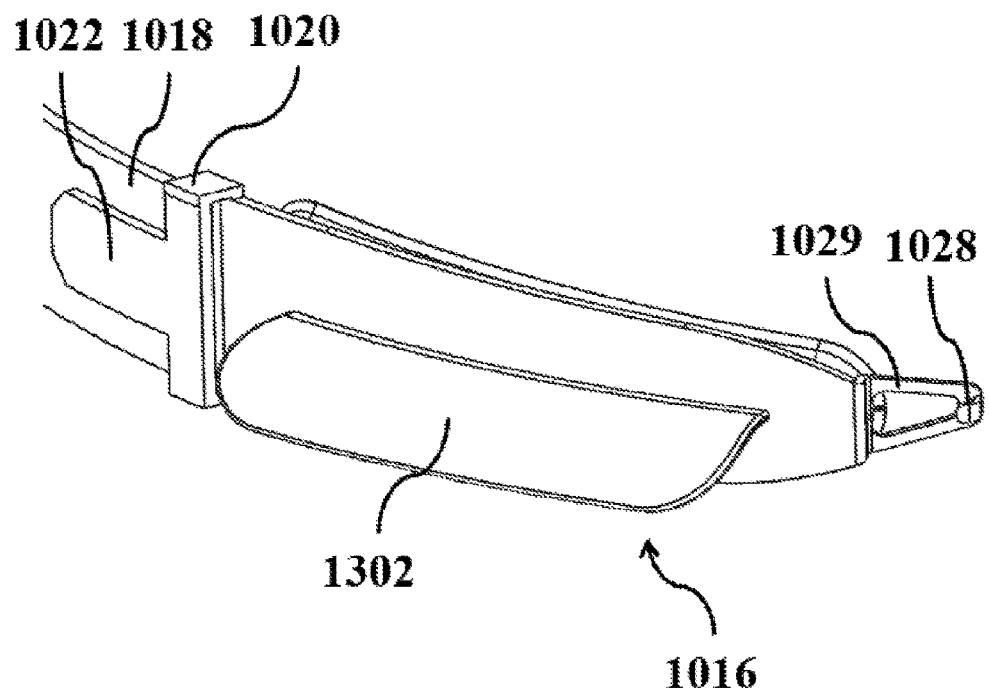

Reference is now made to FIGS. 18A and 18B, which are perspective views of two embodiments for enabling a user to more easily grip posterior member 1016 of the inventive headsets of the teachings herein, such as headset 1010.

As seen in FIG. 18A, in some embodiments the posterior member 1016 may include, on an exterior surface thereof, a plurality of grips 1300 to enable the user to more easily push the posterior member 1016 while donning headset 1010. In some embodiments, the posterior member includes two side grips 1300a and 1300b, and a distal grip 1300e, each configured to be engaged by a single finger of the user. When donning the headset, the user may engage his fingers to grips 1300 in order to push the posterior member rearward and plow through the hair, as described hereinabove. For example, the user may place his middle finger on grip 1300a and his thumb on grip 1300b to hold the posterior member 1016 securely, and may push the posterior member by pushing with his index finger against grip 1300c.

FIG. 18B shows an embodiment of posterior member 1016 including a grip 1302 disposed generally horizontally generally at the center of the posterior member. In some embodiments, the grip 1302 is large enough to be held by at least two fingers, so that when donning headset 1010 the user may hold grips 1302 and push them rearward, thereby pushing the posterior members 1016 rearward as described hereinabove with reference to FIGS. 3A to 3E. In some embodiments the grip 1302 may be made of a flexible and/or resilient material, such as silicone, rubber, and the like, or may be made of a semi-rigid material such as high density polyethylene or polypropylene and include an integral hinge, so that once the headset 1010 is donned the grip 1302 may be pushed to lie flat against the surface of posterior member 1016, thus not discomforting the user, for example if the user is lying down.

FIG. 18B also illustrates one embodiment of a configuration of stretchable member 1018. As seen, in some embodiments, stretchable member 1018 connects directly to the proximal edge of the semi-rigid member 1020 of posterior member 1016, and does not extend over the entire length of the posterior member.

Figure 19:
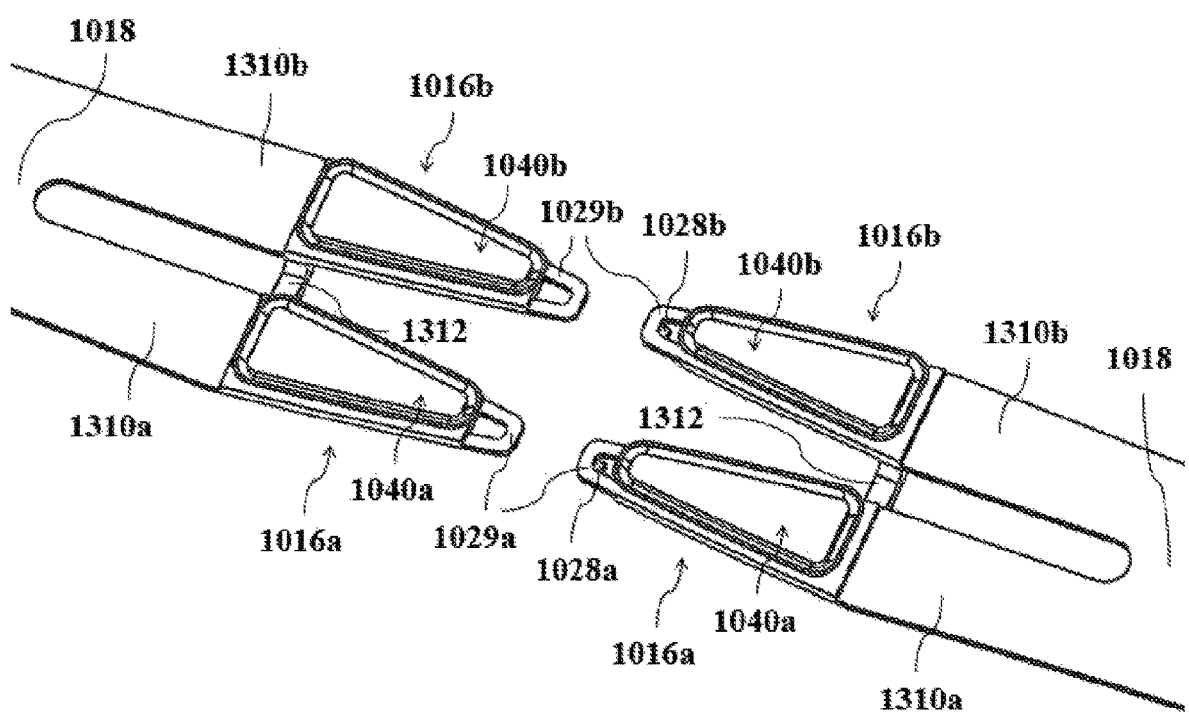
FIG. 19 is a perspective view of an embodiment of the inventive headset of the teachings herein, comprising bifurcated posterior members.

Reference is now made to FIG. 19, Which is a perspective view of an embodiment of the inventive headset of the teachings herein, comprising bifurcated posterior members.

In some embodiments, it is desired to include more than one pair of posterior electrodes 1040 in a single headset 1010, for example in order to stimulate two locations along a nerve, such as the greater occipital nerve, which may improve the efficacy of nerve stimulation.

As seen in FIG. 19, in some such embodiments, the distal end of each stretchable member 1018 is bifurcated, defining two stretchable segments 1310a and 1310b. Each of stretchable segments 1310a and 1310b terminates in a posterior member 1016a and 1016b, respectively, the posterior members 1016a and 1016b being constructed and operative substantially as described hereinabove. Typically, posterior members 1016a and 1016b include posterior electrode systems 1040a and 1040b, respectively, as well as tapered ends 1029a and 1029b respectively, terminating in closure mechanisms 1028a and 1028b, respectively.

In some embodiments, the posterior members 1016a and 1016b are connected to one another by a semi-rigid bridge portion 1312, which maintains the relative distance between the posterior members 1016a and 1016b, and helps ensure proper positioning of the electrodes mounted thereon. In some embodiments the bridge portion 1312 is elevated relative to the surface of the posterior elements 1016, so as to minimize interference of the bridge portion 1312 with the user's hair and discomfort that may be caused thereby, as well as to prevent accumulation of the user's hair against the bridge portion 1312 which may interfere with the user's ability to pull the posterior members 1016 rearward.

In some embodiments, the pair of posterior electrode systems 1040a and 1040b on one side of the headset 1010 may be activated separately from the pair of posterior electrode systems 1040a and 1040b on the other side of headset 1010, for example as two channels of stimulation. For example, the pair of electrodes 1040a and 1040b on the left side of headset 1010 may be activated to provide unilateral stimulation of the left side occipital nerve branches, and the pair of electrodes 1040a and 1040b on the right side of headset 1010 may be activated to provide unilateral stimulation of the right side occipital nerve branches. Such electrode arrangement and stimulation protocol may enable more effective excitation of the nerve, as current flows between the electrodes along the nerve. Such arrangement may also allow the stimulation protocol and/or intensity be adjusted or controlled separately for each of the left and right occipital nerve branches, thereby maximizing the stimulation efficacy and the user's comfort.

Figure 20A:
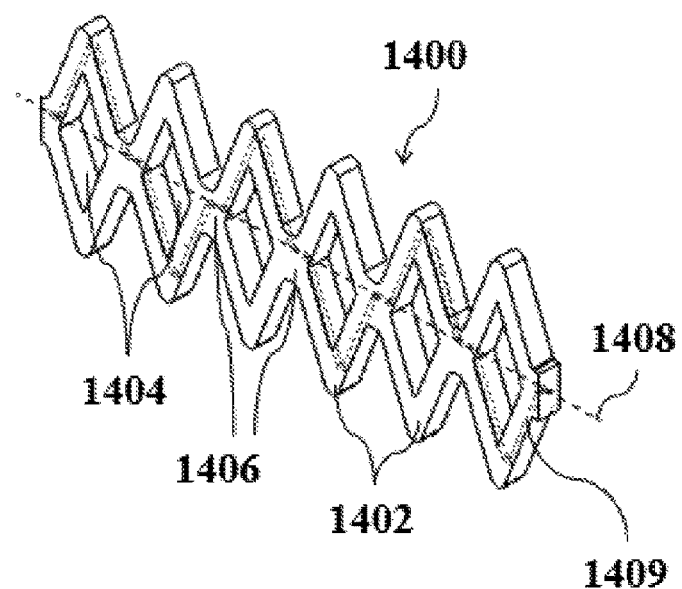
FIGS. 20A, 20B, and 20C provide views of an embodiment of a stretchable member having conductive wiring extending therethrough, which stretchable member is suitable for use in inventive headsets according to the teachings herein, FIG. 20A providing a perspective view, and FIGS. 20B and 20C providing side plan views in a rest state and in a stretched state, respectively.
Figure 20B:
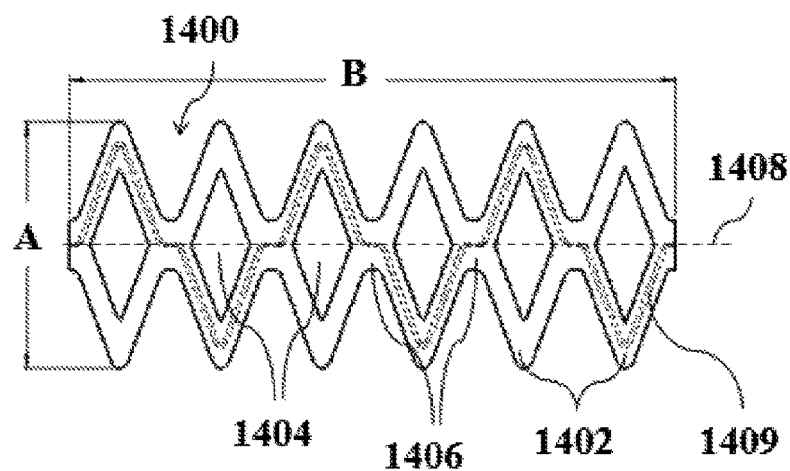
Figure 20C:
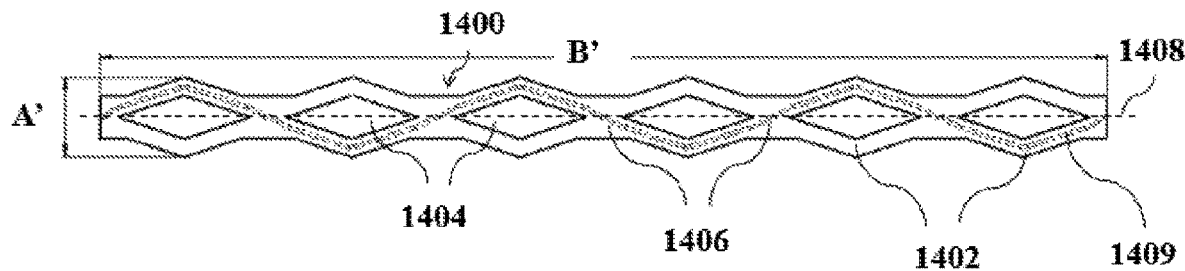

Reference is now made to FIGS. 20A, 20B, and 20C, which provide views of an embodiment of a stretchable member having conductive wiring extending therethrough, which stretchable member is suitable for use in inventive headsets according to the teachings herein, FIG. 20A providing a perspective view, and FIGS. 20B and 20C providing side plan views in a rest state and in a stretched state, respectively.

As seen, a stretchable element 1400 according to the teachings herein includes a plurality of geometrical shapes 1402 having a hollow center 1404, connected to one another by bridging portions 1406. Stretchable member 1400 may be formed of any suitable material, such as silicone, polyurethane-polyurea copolymer (Lycra®), elastane, neoprene, woven elastic polyester, braided elastic nylon, braided elastic polyester, and polyisoprene (synthetic rubber), all of which are highly resilient materials that can deform and change their geometrical shape while relatively low force is applied thereto, and may return to their original shape when the force applied thereto is removed. As explained hereinbelow, geometrical shapes 1402 are vertically symmetrical about an axis 1408. In the illustrated embodiment, the geometrical shapes 1402 comprise diamond shapes, although any other suitable geometrical shape, such as ovals or circles, may be used. A conductive wire 1409 is threaded through the material of geometrical shapes 1402, and is in a fixed position relative to the geometrical shapes. In some embodiments, conductive wire 1409 alternates between portions of the geometrical shapes 1402 disposed above axis 1408 and portions of the geometrical shapes disposed below axis 1408.

As seen from a comparison of FIGS. 20B and 20C, stretching of stretchable element 1400 from a length B at the rest state as shown in FIG. 20B, to a length B' at the stretched state shown in FIG. 20C, results in deformation of geometrical shapes 1402 and extension of the total length of the stretchable element. As a result of the deformation of shapes 1402, there is a change in the shape of conductive wire 1409 without changing the length of the wire within the stretchable element 1400 and without damaging the wire. The deformation of the geometrical shapes 1402 may also results is a decrease in the width of element 1400, from a rest state width A to a stretched state width A', such that A≥A'.

An extension β of stretchable element 1400 is defined as the difference between B' and B divided by the rest length B, as expressed mathematically by β=(B'−B)/B. In some embodiments, the extension β of element 1400 is preferably in the range of 0-3.0, more preferably in the range of 0.2-2.0, or even more preferably in the range of 0.4-1.5.

Figure 21A:
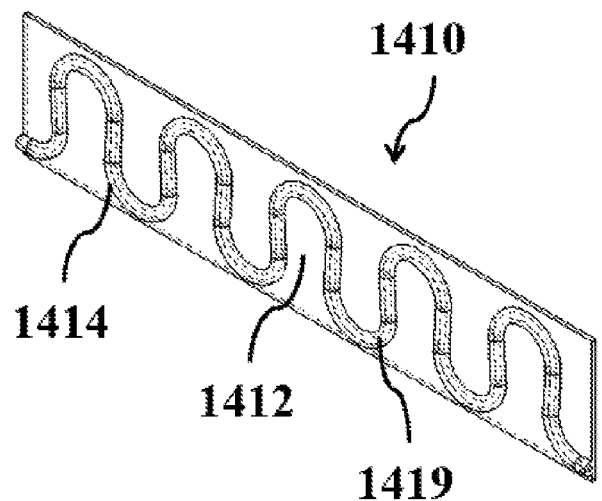
FIGS. 21A, 21B, and 21C provide views of another embodiment of a stretchable member having conductive wiring extending therethrough, which stretchable member is suitable for use in inventive headsets according to the teachings herein, FIG. 21A providing a perspective view, and FIGS. 21B and 21C providing side plan views in a rest state and in a stretched state, respectively.
Figure 21B:
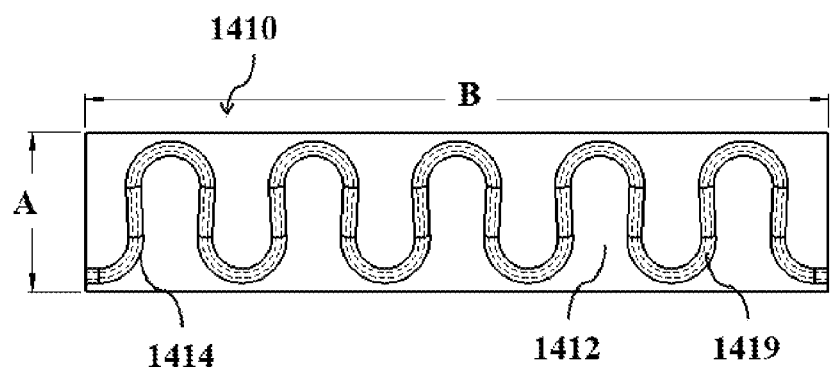
Figure 21C:
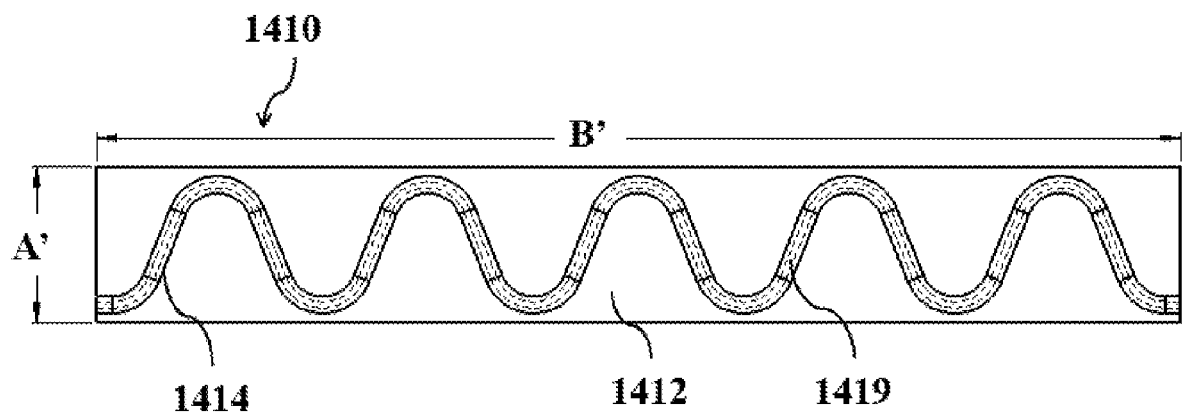

Reference is now made to FIGS. 21A, 21B, and 21C, which provide views of another embodiment of a stretchable member having conductive wiring extending therethrough, which stretchable member is suitable for use in inventive headsets according to the teachings herein, FIG. 21A providing a perspective view, and FIGS. 21B and 21C providing side plan views in a rest state and in a stretched state, respectively.

As seen, a stretchable element 1410 according to the teachings herein comprises a stretchable band 1412, for example made of silicone, polyurethane-polyurea copolymer (Lycra®), elastane, neoprene, woven elastic polyester, braided elastic nylon, braided elastic polyester, and polyisoprene (synthetic rubber), all of which are highly resilient materials that can deform and change their geometrical shape while relatively low force is applied thereto, and may return to their original shape when the force applied thereto is removed, having a conductive wire 1419 threaded through a dedicated channel 1414 in band 1412, which is formed such that in each segment of the stretchable band 1412, the length of the channel 1414 is greater than the length of the band. In the illustrated embodiment, the channel 1414 is in a waveform, although any other suitable shape, such as a zigzag, may be used. In some embodiments, at least some portions of conductive wire 1419 is fixed within channel 1414 relative to the band 1412, so that stretching of band 1412 results in extension of the length covered by the wire, and consequent change in the shape of wire 1419.

As seen from a comparison of FIGS. 21B and 21C, stretching of stretchable element 1410 from a length B at the rest state as shown in FIG. 21B, to a length B' at the stretched state shown in FIG. 21C, results in extension of band 1412 and extension of the total length of the stretchable element. As a result of the stretching of band 1412, there is a corresponding change in the shape of conductive wire 1419, illustrated as a change in the frequency of the waveform shape of the wire, without changing the length of the wire within the stretchable element 1410 and without damaging the wire. The stretching of the band 1412 may also results is a decrease in the width of element 1410, from a rest state width A to a stretched state width A', such that A≥A'.

An extension β of stretchable element 1410 is defined as the difference between B' and B divided by the rest length B, as expressed mathematically by β=(B'−B)/B. In some embodiments, the extension β of element 1410 is preferably in the range of 0-1.5, more preferably in the range of 0.1-1.0, or even more preferably in the range of 0.2-0.7.

Reference is now made to FIGS. 22A, 22B, 22C, and 22D, which provide views of yet another embodiment of a stretchable member having conductive wiring extending therethrough, which stretchable member is suitable for use in inventive headsets according to the teachings herein, FIG. 22A providing a perspective view, FIGS. 22B and 22C providing side plan views in a rest state and in a stretched state, respectively, and FIG. 22D providing a sectional view taken along section lines A-A in FIG. 22B.

As seen, a stretchable element 1420 according to the teachings herein comprises a stretchable band 1422, for example made of silicone, polyurethane-polyurea copolymer (Lycra®), elastane, neoprene, woven elastic polyester, braided elastic nylon, braided elastic polyester, and polyisoprene (synthetic rubber), all of which are highly resilient materials that can deform and change their geometrical shape while relatively low force is applied thereto, and may return to their original shape when the force applied thereto is removed, including a hollow channel portion 1424 having a plurality of pins 1426, formed within the channel. In some embodiments, the pins are fabricated of the same material as band 1422, and may be integrally formed therewith, as seen in FIG. 22D. A conductive wire 1429 is threaded within channel portion 1424 around pins 1426, for example in a waveform or zigzag shape, such that pins 1426 support the wire 1429 and hold it in place. In some embodiments, wire 1429 is not fixed within channel portion 1424, and can move relative to pins 1426.

As seen from a comparison of FIGS. 22B and 22C, stretching of stretchable element 1420 from a length B at the rest state as shown in FIG. 22B, to a length B' at the stretched state shown in FIG. 22C, results in extension of band 1422 and extension of the total length of the stretchable element. As a result of the stretching of band 1422 and extension of the distances between adjacent pins 1426, there is a corresponding change in the arrangement of wire 1429 on the pins 1426, illustrated as a change in the frequency of the waveform shape of the wire, without changing the length of the wire within the stretchable element 1420 and without damaging the wire. The stretching of the band 1422 may also results is a decrease in the width of element 1420, from a rest state width A to a stretched state width A', such that A≥A'.

An extension β of stretchable element 1420 is defined as the difference between B' and B divided by the rest length B, as expressed mathematically by β=(B'−B)/B. In some embodiments, the extension β of element 1420 is preferably in the range of 0-1.5, more preferably in the range of 0.1-1.0, or even more preferably in the range of 0.2-0.7.

Figure 23:
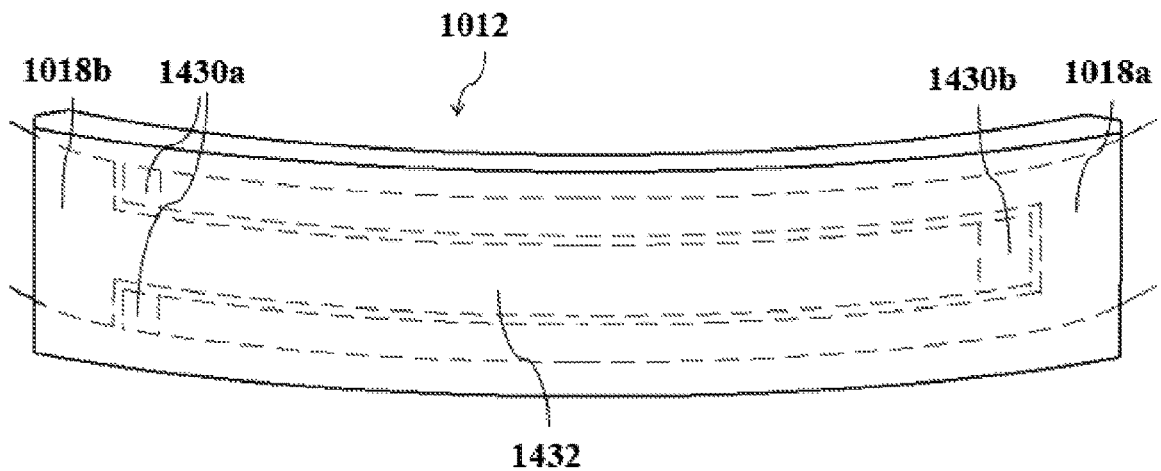
FIG. 23 is a perspective view of an embodiment of an arrangement of stretchable members within an anterior member of an inventive headset according to the teachings herein.

Reference is now made to FIG. 23, which is a perspective view of an embodiment of an arrangement of stretchable members within an anterior member of an inventive headset according to the teachings herein.

As seen in FIG. 23, stretchable members 1018 may be arranged within anterior member 1012 such that they overlap. For example, in the illustrated embodiment, a first stretchable member 1018a, illustrated as extending out of the right side of anterior member 1012, is anchored to anterior member 1012 at one or more first anchoring points 1430a, illustrated on the left side of anterior member 1012. A second stretchable member 1018b, illustrated as extending out of the left side of anterior member 1012, is anchored to anterior member 1012 at one or more second anchoring points 1430b, illustrated on the right side of anterior member 1012. As a result, sections of stretchable members 1018a and 1018b overlap in area 1432 extending between the first and second anchoring points 1430.

It will be appreciated that the arrangement of stretchable members 1018 illustrated in FIG. 23 allows a greater length for each stretchable member 1018, without changing the circumference of headset 1010. The greater length allows for the extension of the stretchable members 1018 to be distributed over a greater length, preventing excessive stretching of the stretchable members 1018 and excessive pressures that may be caused thereby.

Figure 24:
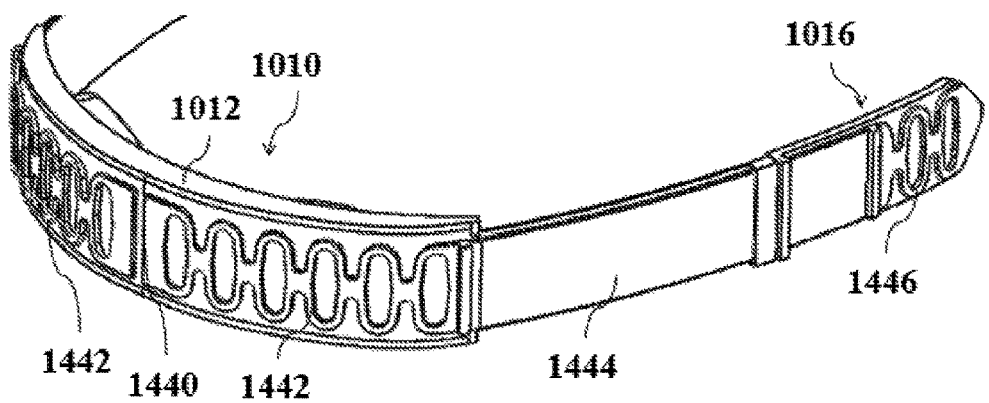
FIG. 24 is a perspective cut-away view of an embodiment of an arrangement of two types of stretchable members within an anterior member of an inventive headset of the teachings herein.

Reference is now made to FIG. 24, which is a perspective cut-away view of an embodiment of an arrangement of two types of stretchable members within an anterior member of an inventive headset of the teachings herein.

As seen, the stretchable members may be anchored to anterior member 1012 at an anchoring point 1440 disposed generally in the center of the anterior member. In the illustrated embodiment, each stretchable member comprises a first portion 1442 formed of a first type of stretchable material, here shown as an oval based stretchable material, similar to that described hereinabove with reference to FIGS. 20A to 20C, disposed within anterior member 1012. A second portion 1444 of the stretchable member, formed of a second type of stretchable material, here shown as a plain elastic band but which may also be a band as described hereinabove with reference to FIGS. 21A to 22D, extends from the end of anterior member 1012 to the beginning of posterior member 1016, and in some embodiments also over and/or through portions of the posterior member 1016. In some embodiments, each stretchable member also includes a third portion 1446, disposed over or through at least part of the posterior member 1016. In some embodiments, the third portion 1446 is formed of a third type of stretchable material. In some embodiments, such as the illustrated embodiment, the third portion 1446 is formed of the same type of stretchable material as the first portion 1442.

It will be appreciated that use of two different types of stretchable materials in the stretchable members assists in providing sufficient stretching of the stretchable element without applying too much radial pressure to the user's head. Specifically, a geometric shape based stretchable material as described hereinabove with respect to FIGS. 20A to 20C allows for relatively long extension while using less force than that required to reach the same extension using other types of stretchable elements. Since the length of the stretchable element is limited, for example by the length of the flexible arm members (shown in FIGS. 1A and 1B), use of such a stretchable material enables the stretchable element to stretch to the necessary length without being initially long and without applying too much radial pressure to the head of the user.

Figure 25A:
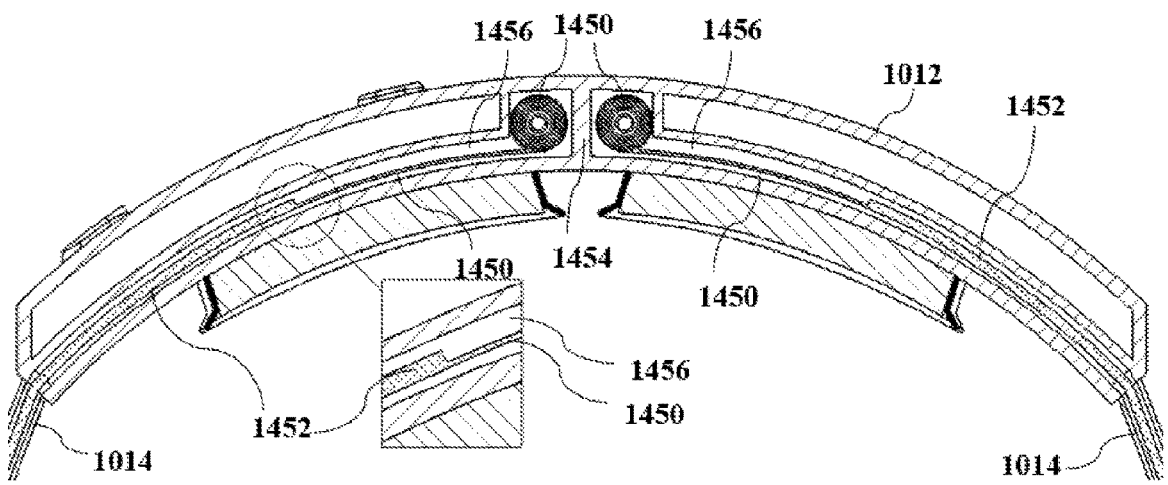
FIGS. 25A and 25B provide sectional views of another embodiment of an arrangement of two types of stretchable members within an anterior member of an inventive headset according to the teachings herein, the stretchable members being in a rest state and in a stretched state, respectively.
Figure 25B:
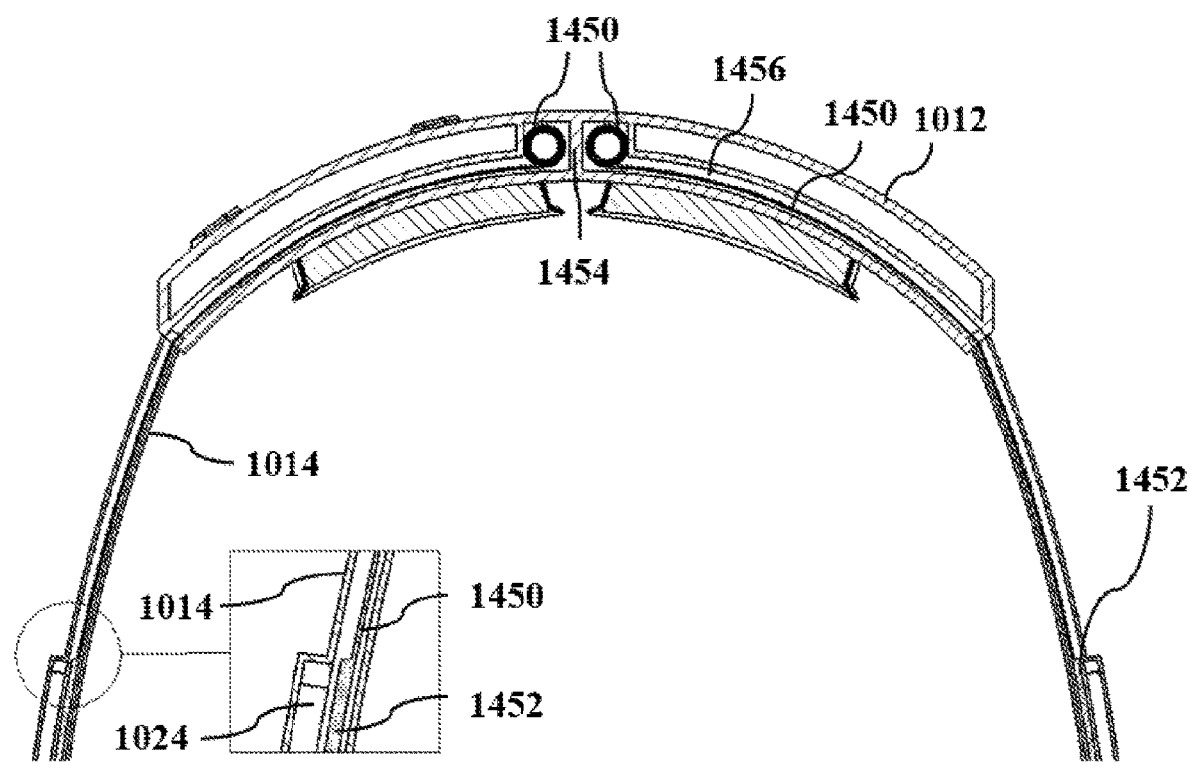

Reference is now made to FIGS. 25A and 25B, which provide sectional views of another embodiment of an arrangement of two types of stretchable members within anterior member 1012 of an inventive headset 1010 according to the teachings herein, the stretchable members being in a rest state and in a stretched state, respectively.

As seen in FIGS. 25A and 25B, the stretchable members may include a constant force spring 1450 connected to a second type of stretchable element 1452, such as a simple elastic band, or elastic members 1410 or 1420 described hereinabove with reference to FIGS. 21A to 21C and 22A to 22D, respectively. In the illustrated embodiment, two constant force springs 1450 are disposed generally at the center 1454 of the anterior member 1012, and are anchored therein. The loose end of each spring coil 1450 is connected to a stretchable element 1452, which extends through a suitable slot 1456 in anterior member 1012, and then continues to extend through flexible arm members 1014.

In the rest state, illustrated in FIG. 25A, most of each constant force spring 1450 is coiled, such that the length contributed by the springs is short, and the stretchable element 1452 extends through the slot 1456 and through sleeves 1014 to posterior elements 1016 (not shown). When the user dons the headset 1010 and pulls the posterior elements 1016 rearward, each constant force spring 1450 is pulled and uncoiled, such that the stretchable element 1452 extends out of sleeves 1014 and the space in sleeves 1014 and in slot 1456 is filled by the stretched constant force spring 1450, as shown in FIG. 25B.

It is appreciated that, in some embodiments, the constant force spring 1450 may obviate the need for a size adjustment mechanism, since spring 1450 may assume different lengths and thus functionally adjust the size of the headset, while maintaining fixed radial pressure on the user's head regardless of the size. In some embodiments, constant force spring 1450 may also be used as an electrical conductor.

Figures 26, 27:
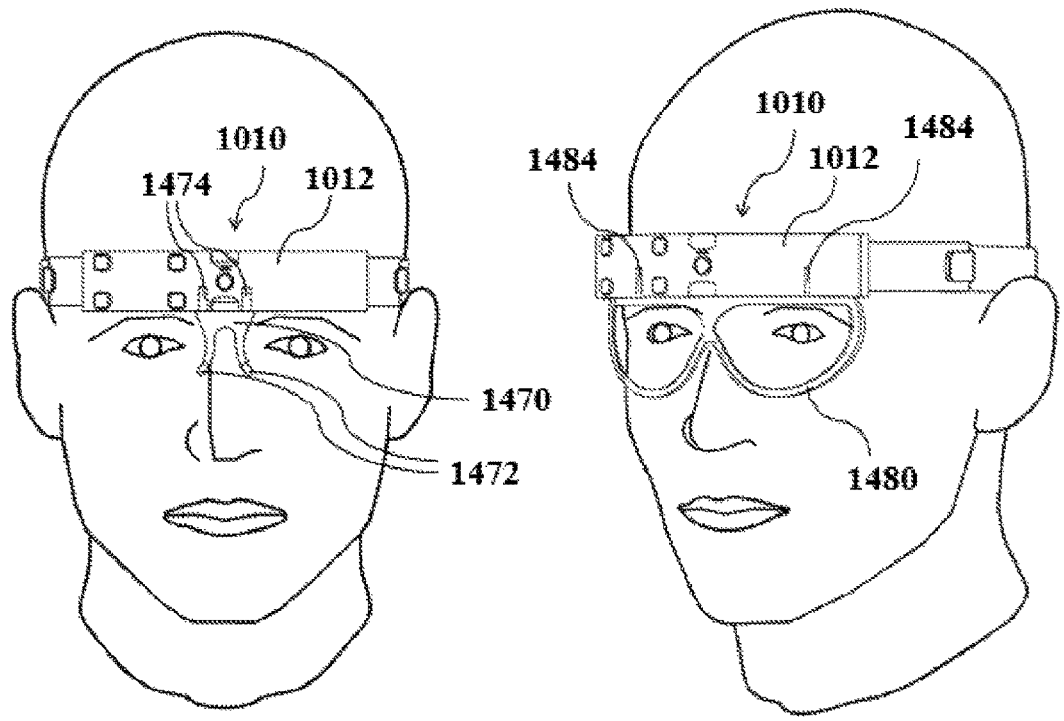
FIG. 26 is an anterior view of an embodiment of the inventive headset of FIGS. 1A and 1B positioned on the head of a user and including a nose bridge support member.
FIG. 27 is a perspective anterior view of an embodiment of the inventive headset of FIGS. 1A and 1B positioned on the head of a user and including associated eyeglasses.

Reference is now made to FIG. 26, which is an anterior view of the inventive headset 1010, including a nose bridge support member 1470 and positioned on the head of a user.

Nose bridge support member 1470 may be configured to be located in the central area of anterior member 1012. Nose bridge support member 1470 may be rigid or semi-rigid, and may have two elongate portions 1472 adapted to be aligned at both sides of the upper part of the nose and the nose bridge. Positioning the nose bridge support member 1470 over the nose may allow the user to determine the rotational and longitudinal placement of headset 1010, for example while donning the headset.

Nose bridge support member 1470 may also be configured to further support anterior member 1012 against gravity, thereby enabling the user to more easily don headset 1010, and obviating the need for the headset 1010 to form a monolithic and/or integral unit during initial steps of donning illustrated in FIGS. 3A and 3B.

In some embodiments, nose bridge support member 1470 is removably and replaceably attached to anterior member 1012 by one or more pins 1474, configured to be inserted into corresponding bores in anterior member 1012, and may be detached from the anterior member 1012 by pulling pins 1474 out of the bores in which they are housed. A nose bridge support member 1470 of various sizes and shapes may be selected for individual users. In some embodiments, nose bridge support member 1470 is sufficiently flexible and/or resilient so as to allow the user to manually adjust the nose bridge for optimal adjustment to the nose of the user.

Reference is now made to FIG. 27, which is a perspective anterior view of the inventive headset 1010, including associated eyeglasses 1480 and positioned on the head of a user.

Eyeglasses 1480 may be configured to be located in the central area of anterior member 1012. Positioning the eyeglasses 1480 over the nose and eyes may allow the user to determine the rotational and longitudinal placement of headset 1010, for example while donning the headset.

Eyeglasses 1480 may also be configured to further support anterior member 1012 against gravity, thereby enabling the user to more easily don headset 1010, and obviating the need for the headset 1010 to form a monolithic and/or integral unit during initial steps of donning illustrated in FIGS. 3A and 3B. In some embodiments, eyeglasses 1480 are removably attached to anterior member 1012 by one or more pins 1484, configured to be inserted into corresponding bores in anterior member 1012, and may be detached from the anterior member 1012 by pulling pins 1484 out of the bores in which they are housed. In some embodiments, eyeglasses 1480 may comprise optical lenses for improved eyesight, dark lenses suitable to be used as sunglasses, non-optical transparent lenses, or highly dark lenses that may be used to block external light, for example, in order to assist during migraine attack or for relaxation.

Figure 28:
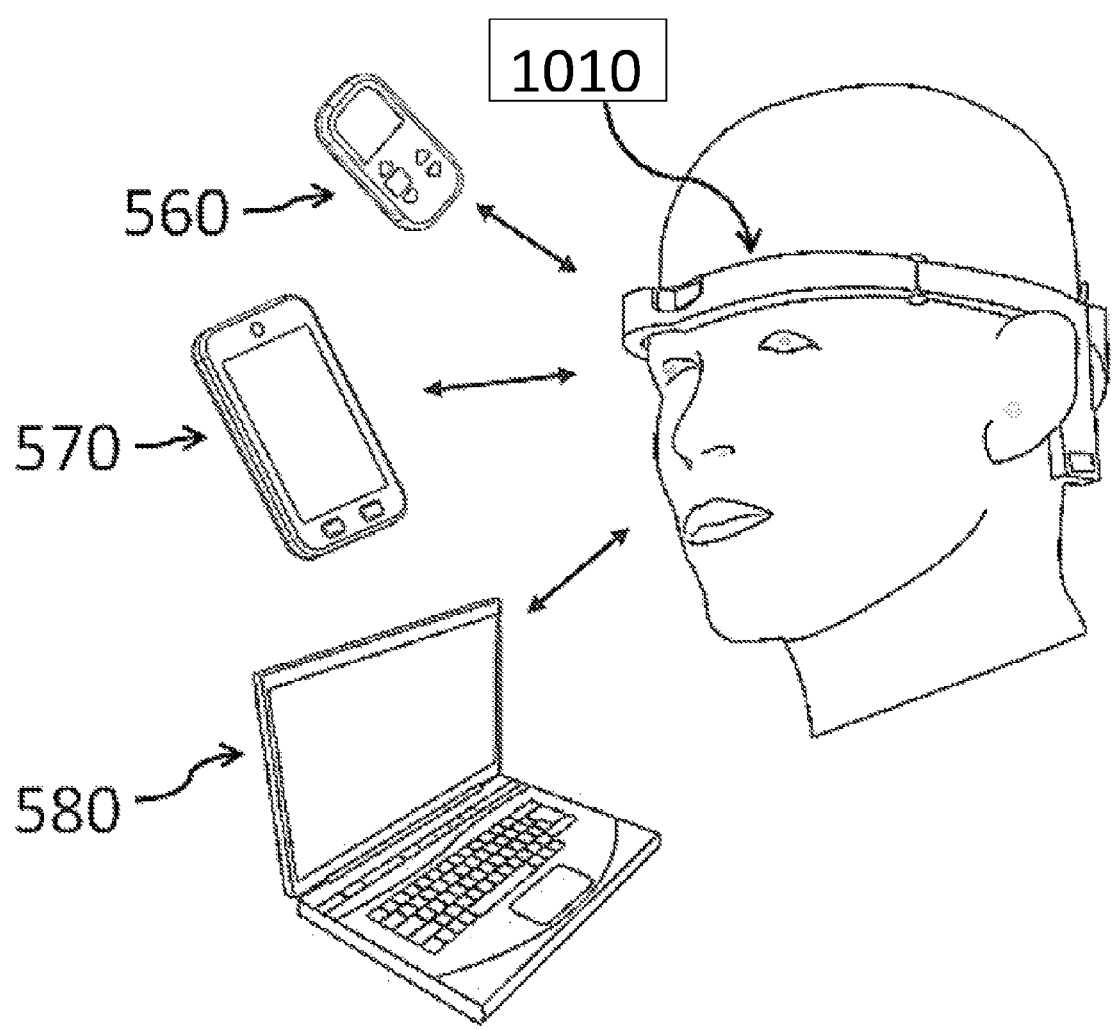
FIG. 28 provides a perspective view of a donned, inventive headset adapted to communicate with a remote control unit, mobile phone, and computer.

FIG. 28 illustrates a perspective view of headset 1010 along with a remote control or remote control handset 560, a mobile phone 570 and a laptop/PC 580.

In some embodiments, headset 1010 may be configured to communicate wirelessly with remote control 560. Remote control 560 may be used by the user to send commands to headset 1010, such as stimulation initiation or cessation commands, or commands to increase or decrease the stimulation intensity. Remote control 560 may also present various visual and audio indications for the user regarding the status of headset 1010.

Headset 1010 may be configured to wirelessly communicate with a mobile phone 570. The mobile phone interface may be used to present various data sent wirelessly by headset 1010, for example, visual and audio indications regarding the status of headset 1010 and usage logs.

Headset 1010 may be configured to wirelessly communicate with laptop/PC 580. The mobile phone interface may be used to present various data sent wirelessly by headset 1010, such as visual and audio indications regarding the status of headset 1010 and usage logs.

Communication between headset 1010 and remote control 560, mobile phone 570 and laptop 580 may be performed in various ways, known to those of ordinary skill in the art, for example by Bluetooth communication.

Reference is now made to FIG. 29, which is a perspective view of an embodiment of an inventive headset 1490, similar to the inventive headset 1010 of FIGS. 1A and 1B, including side electrodes 1492, and to FIGS. 30A and 30B, which provide schematic illustrations of the headset 1490 positioned on the head of the user, such that electrodes included therein stimulate specific nerve branches in the head of the user.

As seen in FIG. 29, one or more side electrodes 1492 may be mounted on each of flexible arm members 1014. In the illustrated embodiments, each arm member 1014 includes a proximal side electrode 1492a disposed on the arm member 1014 near anterior member 1012, and a distal side electrode 1492b disposed on the arm member 1014 near the distal end of arm member 1014. In some embodiments, when headset 1490 is donned by the user, some or all of side electrodes 1492 are located at areas including hair, and are in direct contact with the skin due to plowing away of the hair by tapered end 1029 as described hereinabove.

It will be appreciated that side electrodes 1492 are constructed and operative similar to electrodes 1030 and 1040 described hereinabove with respect to FIGS. 1A and 1B. It is appreciated that in some embodiments (not illustrated), the side electrodes 1492 may be the main or the only electrodes included in headset 1490, and thus electrodes 1030 and/or 1040 may be obviated. It is further appreciated that in some embodiments some or all of side electrodes 1492 may be sensing electrodes, such as electroencephalogram (EEG) electrodes, skin conductance response (SCR) electrodes, impedance plethysmograph (IPG) electrodes, or electromyograph (EMG) electrodes.

As seen in FIGS. 30A and 30B, each of the electrodes included in headset 1490 and/or in headset 1010 of FIGS. 1A and 1B is configured to be positioned, when the headset is donned on the head of a user, above one or more specific nerves or brain regions for stimulation thereof.

Turning to FIG. 30A, it is seen that posterior electrode systems 1040 may be positioned to stimulate the greater occipital nerve, indicated by reference numeral 1494, and/or the lesser occipital nerve, indicated by reference numeral 1495, and/or the third occipital nerve (not illustrated). In some embodiments, such as when conducting transcranial stimulation, at least one of posterior electrodes 1040 may be activated simultaneously with at least one anterior electrode 1030 or with at least one side electrode 1492, thereby to stimulate regions of the frontal, temporal, and/or occipital lobes of the user's brain.

In some embodiments, proximal side electrodes 1492a may be positioned to stimulate the zygomaticotemporal nerve indicated by reference numeral 1496, and distal side electrodes 1492b may be positioned to stimulate the auriculotemporal nerve, indicated by reference numeral 1497. In some embodiments, such as when conducting transcranial stimulation, at least one of side electrodes 1492 may be activated simultaneously with at least one anterior electrode 1030, with at least one contralateral side electrode 1492, or with at least one posterior electrode 1040, thereby to stimulate regions of the frontal, temporal, and/or occipital lobes of the user's brain.

Turning to FIG. 30B, it is seen that anterior electrode systems 1030 disposed on anterior member 1012 may be positioned to stimulate the right and left branches of the supratrochlear nerve, indicated by reference numeral 1498, and/or the right and left branches of the supraorbital nerve, indicated by reference numeral 1499.

Figure 31:
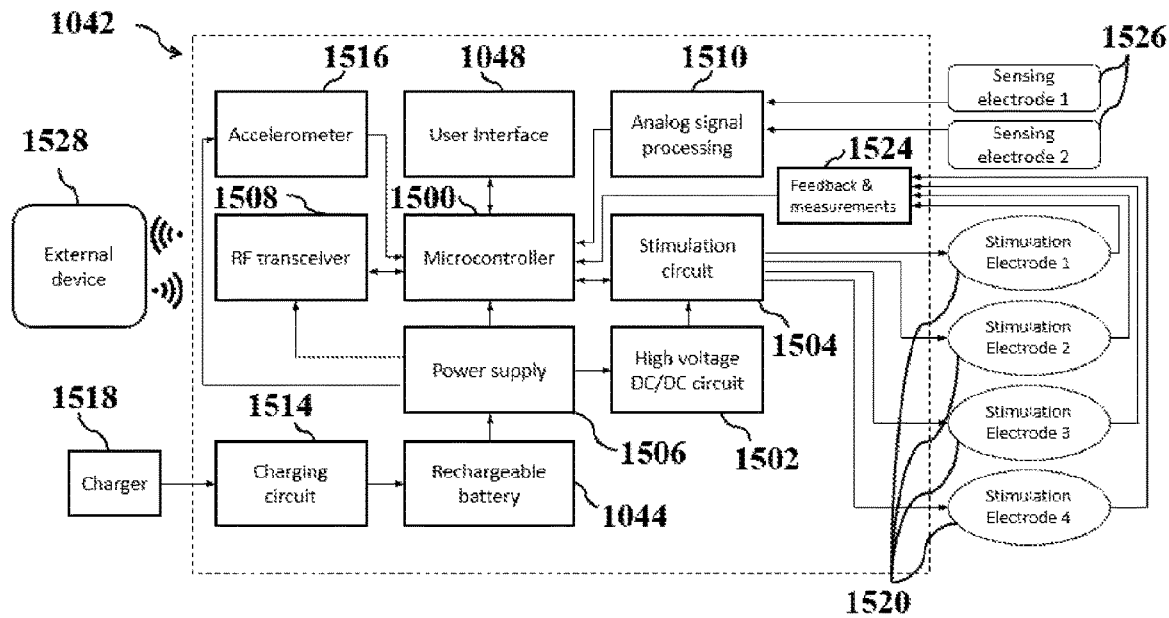
FIG. 31 provides a schematic block diagram of an embodiment of an electronic circuit usable in an inventive headset according to any of the embodiments described herein.

Reference is now made to FIG. 31, which provides a schematic block diagram of an embodiment of an electronic circuit usable in an inventive headset according to any of the embodiments described herein, such as headset 1010 of FIGS. 1A and 1B, headset 1070 of FIGS. 1C and 1D, or headset 1490 of FIGS. 29 to 30B.

As seen, an electronic circuit, such as electronic circuit 1042 described hereinabove with reference to FIGS. 1A and 1B, may include any one or more of a microcontroller 1500, a high voltage circuit 1502, a stimulation circuit 1504, an internal power supply 1506, a radio-frequency (RF) transceiver 1508, an analog signal processing circuit 1510, a rechargeable battery electrically associated with circuit 1042, such as battery 1044 of FIGS. 1A and 1B, a charging circuit 1514, an accelerometer 1516, and a user interface 1048, for example as described hereinabove with reference to FIGS. 1A and 1B. In some embodiments, electronic circuit 1042 may include additional sensors, not shown, as described hereinbelow.

As mentioned hereinabove, the electronic circuit 1042 may be electrically associated with, and powered by rechargeable battery 1044 that is electrically connected to internal power supply 1506. In some embodiments, the internal power supply 1506 provides power to high voltage circuit 1502, which in turn is electrically connected to stimulation circuit 1504. The charging circuit 1514 is electrically associated with rechargeable battery 1044, and may interface with an external power supply, such as a charger 1518. The high voltage circuit 1502 provides to stimulation circuit 1504 current with voltage measuring up to 120.

In some embodiments, the stimulation circuit 1504 receives information and/or commands from the microcontroller 1500. The stimulation circuit 1504 is configured to provide electrical stimulation pulses to the user's nerve tissues via one or more stimulation electrodes 1520 disposed on the headset, such as stimulation electrodes 1030 and/or 1040 of FIGS. 1A and 1B, and stimulation electrodes 1492 of FIG. 29.

In some embodiments, electronic circuit 1042 may include two or more high voltage circuits (not shown) similar to circuit 1502, each high voltage circuit providing current at a voltage of up to 120 volts to at least two of stimulation electrodes 1520. In some embodiments, electronic circuit 1042 may include at least two galvanic isolated output channels (not shown), each output channel providing output to at least two of stimulation electrodes 1520.

In some embodiments, the electronic circuit 1042 also includes a feedback & measurement circuit 1524, which collects voltage or current level information from the stimulation electrodes 1520, and provides the collected information to the microcontroller 1500, The microcontroller 1500 uses the provided feedback to monitor and control the voltage and current levels in stimulation electrodes 1520 in order to maintain the desired stimulation level, to optimize energy consumption, and to ensure the user's safety. In some embodiments, the microcontroller 1500 may alert the user, for example by providing an audible or tactile indication, or may halt the provision of current for stimulation in the case of an emergency or of incorrect function of the headset. For example, microcontroller 1500 may alert the user and may halt the provision of current for stimulation if a reduction of current level is detected as a result of improper contact of one or more of electrodes 1520 with the user's skin.

In some embodiments, the microcontroller 1500 may instruct the stimulation circuit 1504 to output electrical current in various patterns and/or for various periods of time. For example, the microcontroller 1500 may instruct the stimulation circuit 1502 to provide electrical current having an amplitude that ramps up, ramps down, or remains stable. In some embodiments the microcontroller 1500 instruct the stimulation circuit 1504 with regards to various stimulation parameters, such as the current amplitude, pulse frequency, phase duration, and amplitude of the current output by the stimulation circuit. In some embodiments, the microcontroller instructs the stimulation circuit 1504 to provide an output having a constantly changing pattern of at least one of the stimulation parameters.

In some embodiments, the microcontroller 1500 may instruct the stimulation circuit 1504 to provide an output signal having a different pattern for each of a plurality of activated pairs of electrodes. For example, the stimulation circuit 1504 may stimulate one pair of electrodes at a pulse frequency of 50 Hz and a phase duration of 300 μsec and another pair of electrodes at a pulse frequency of 100 Hz and a phase duration of 200 μsec. At any given time the microcontroller 1500 may activate only one pair of electrodes, may activate a combination of electrodes, may activate several electrodes simultaneously, sequentially, or alternately.

In some embodiments, some electrodes 1520 may provide as output an alternating current signal, whereas other electrodes 1520 may provide as output a direct current. In some embodiments, at least two electrodes 1520 may alternate the type of current provided as output between alternating current and direct current.

In some embodiments, during direct current stimulation in which excitation of a certain region of the brain is determined based on the polarity of an electrode which is positioned above that region of the brain, at least one electrode 1520 may be assigned by the microcontroller 1500 to be the anode, or positively charged electrode, and at least one other electrode 1520 may be assigned to be the cathode, or negative charged electrode.

In some embodiments, stimulation patterns determined by or assigned by the microcontroller 1500 as described above may be stored in the microcontroller 1500 or in a volatile or non-volatile memory (not shown) associated therewith, and may be activated by the user. In some embodiments, the stored stimulation patterns may be modified by the user, for example, by means of user interface 1048 included in the headset, or by means of an external user interface. In some embodiments, a clinician may modify the stored stimulation pattern for a patient physically when the patient visits the clinician, or remotely, such as via a remote cloud base portal which is in communication with the patient's external interface.

In some embodiments, electronic circuit 1042 may be configured to receive analog signal input, such as electroencephalogram (EEG) signals, skin conductance response (SCR) signals, impedance plethysmograph (IPG) signals, electromyograph (EMG) signals, or other bio-signals, from one or more sensors, such as sensing electrodes 1526. The analog signal input received from sensing electrodes 1526 may be processed by analog signal processing circuit 1510, and may be transferred therefrom to microcontroller 1500. In some embodiments, electronic circuit 1042 may be configured to receive digital, analog, or other input from additional sensors disposed on or within the headset, or located elsewhere in the vicinity of the user. In some embodiments, one or more stimulation parameters may be altered by the microcontroller 1500 due to inputs received from one or more of the additional sensors. For example, upon receiving certain EEG input from the analog signal processing circuit 1510, the microcontroller 1500 may modify one or more parameters of the stimulation current which is provided by the stimulation circuit 1504, such as current amplitude, pulse frequency, and the like. In some embodiments, upon receiving input from the analog signal processing circuit 1510, the microcontroller 1500 may activate a specific combination and/or sequence of electrodes and/or may modify the duration of stimulation provided by certain electrodes.

In some embodiments, accelerometer 1516, or any other suitable orientation sensor, may be configured to sense the angular position of the headset and thereby to provide an indication for proper placement of the headset on the user's head. For example, in case that the user positions the headset upside down on his head, the accelerometer may transfer headset orientation data sensed thereby to microcontroller 1500, which may detect the misplacement of the headset and may prevent activation of the electrodes as long as the undesired position of the headset maintained. The user may be alerted to the misplacement of the headset, for example by user interface 1048 or by a remote interface, and may be instructed to correct the headset position.

In some embodiments, input received from the additional sensors and/or from sensing electrodes 1526 may be transferred directly to the patient's clinician or care giver, for example via and external interface and a cloud based portal, allowing the clinician or care giver to monitor the patient's condition, and to alter the patient's treatment program and stimulation pattern accordingly.

In some embodiments, RF transceiver 1508 may enable the microcontroller 1500 to communicate with an interface of an external device 1528, such as a mobile phone, a tablet, a Personal Digital Assistant (PDA), or a computer by way of radio frequency. The RF transceiver 1508 may transmit digital information to and may receive digital information from the microcontroller 1500.

The interface of device 1528 may comprise a software application that may be downloadable from a readily accessible resource, such as from the Internet. The interface may provide to a user thereof an indication, for example by way of a display, of the status of the headset, including, for example, information relating to active stimulation channels, stimulation intensity, active program, treatment time, headset battery status, and RF communication status, as well as various alerts such as alerts relating to electrode contact quality and to proper or improper headset alignment on the head. Additionally, the interface may provide to the user, for example by way of a display, usage logs and/or reports, such as information relating to daily stimulation time, stimulation parameters which were used during stimulation, and treatment programs which were used. The interface may also display, or otherwise provide, to the user raw or processed information received from sensors included in or associated with the headset.

In some embodiments, the headset may be controlled remotely via the interface of external device 1528. For example, the external interface may enable a user thereof to activate or turn off the headset, start or pause stimulation, adjust the stimulation intensity for one or more channels, and select a treatment program. In some embodiments, information collected by the microprocessor 1500 may be transmitted, via the external interface, to a remote location, such as a cloud based portal, where the information may be stored or may be analyzed and/or monitored, for example by a clinician or care taker. In some embodiments, patients undergoing treatment using the headset may use the interface of external device 1528 to provide input or information regarding their condition, thereby enabling a clinician to monitor the patient's condition and provide recommendations for a modified treatment program or actively modify the patient's stimulation parameters remotely in real time. The patient may also use the external interface to download new treatment programs to the headset.

In some embodiments, user interface 1048 located on the headset and the external user interface may enable parallel control of the headset, allowing the user to operate the headset by either of the interfaces. In sonic embodiments, the external interface serves as a display only and does not provide active control of the headset. In some embodiments, user interface 1048 on the headset is obviated, and all interaction with the headset is carried out via the external interface. In some embodiments, the external interface comprises a proprietary electronic device. In some embodiments, the external interface may communicate with electronic circuit 1042 via a cable, such as a USB cable.

Figure 32:
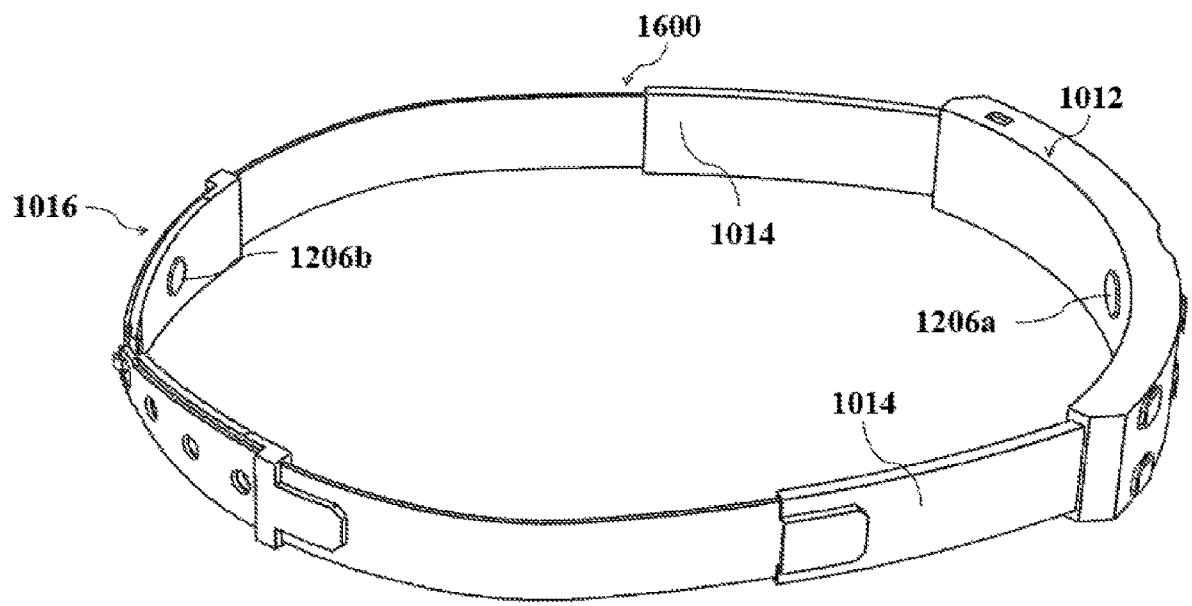
FIG. 32 is a perspective view of an embodiment of an inventive headset, similar to the inventive headset of FIGS. 1A and 1B, including sensors of body parameters.

Reference is now made to FIG. 32, which is a perspective view of an embodiment of an inventive headset 1600, similar to the inventive headset 1010 of FIGS. 1A and 1B, including sensors 1602.

As seen in FIG. 32, in some embodiments, one or more sensors 1602 are mounted on headset 1600, and are configured to sense various body parameters of the user when the headset is donned. In the illustrated embodiments, one or more anterior sensors 1602*a* are disposed on anterior member 1012, and one or more posterior sensors 1602*b* are disposed on posterior members 1016. However, it is appreciated that sensors 1602 may be disposed at any suitable location on headset 1600, for example on arm members 1014. In some embodiments, headset 1600 may include stimulating or sensing electrodes, such as electrodes 1030 and 1040 of FIGS. 1A and 1B, in addition to sensors 1602.

The sensors 1602 may include any suitable type of sensor, such as temperature sensors, orientation sensors, blood pressure sensors, pulse oximetry sensors, electrical conductivity sensors such as sensors for measuring skin conductance response (SCR) and impedance plethysmograph (IPG), electroencephalogram (EEG) and electromyograph (EMG), The user dons headset 1600 in a similar manner to that described hereinabove with reference to FIGS. 3A to 3E, such that posterior member 1016 plow through the hair and enable posterior sensors 1602*b* to directly engage the skin of the scalp, and not to be obstructed by layers of hair located thereunder.

As used herein in the specification and in the claims section that follows, the term "or" is considered as inclusive, and therefore the phrase "A or B" means any of the groups "A", "B", and "A and B".

As used herein in the specification and in the claims section that follows, the term "monolithic" means structurally behaving as a single, at least semi-rigid whole.

As used herein in the specification and in the claims section that follows, the term "monolithically donnable", with respect to a headset, headset frame, or the like, refers to a structure enabling the donning of the headset, headset frame, or the like as a single, at least semi-rigid whole.

As used herein in the specification and in the claims section that follows, the term "circumferential headset" refers to a headset that is adapted, when the headset closure mechanism is in a closed state or when the headset in an operational mode, to fully encompass the head of the headset user.

As used herein in the specification and in the claims section that follows, the term "operational mode", or the like, with respect to a headset or headset component, refers to a headset or headset component that is fitted onto the head of the user, in a suitable rotational and longitudinal disposition, with electrical stimulation being applied.

As used herein in the specification and in the claims section that follows, the term "integral" refers to a structure behaving as a single, whole structure. The term may be applied in particular to flexible structures such as an electrode pad.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Similarly, the content of a claim depending from one or more particular claims may generally depend from the other, unspecified claims, or be combined with the content thereof, absent any specific, manifest incompatibility therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A headset comprising:
   an elongate, unitary body member sufficiently long to encircle the head of a user, said unitary body member having a closed state and a rest state;
   a closure mechanism formed by ends of said unitary body member, said closure mechanism having an open state and a closed state, wherein said unitary body member is in said rest state when said closure mechanism is in said open state and said unitary body member is in said closed state and forms a circumferential headset when said closure mechanism is in said closed state; and at least one posterior electrode, fixedly attached to said unitary body member inwardly of said closure mechanism when said unitary body member is in said rest state prior to initiating donning of said headset, said at least one posterior electrode configured, when said headset is donned on a user's head, to be positioned against the skin of the head of said user, said at least one posterior electrode electrically communicating with a processing unit, wherein said unitary body member comprises at least one posterior member and an at least semi-rigid anterior member, wherein said at least one posterior member and said anterior member are formed as portions of the unitary body member such that longitudinal axes of said at least one posterior member and said anterior member are parallel or coaxial, said at least one posterior electrode being fixedly attached to said at least one posterior member, said at least one posterior member being at least semi-rigid and terminating in a tapered end to which is connected said closure mechanism, said tapered end tapering from a first portion having a first width to a second portion having a second width, smaller than said first width, said tapered end of said at least one posterior member and said closure mechanism being configured to plow between hair to access the scalp of said user during donning of said headset, such that when said headset is donned, said at least one posterior electrode is in direct physical contact with said scalp of said user, wherein, a longitudinal axis of said tapered end is continuous to a longitudinal axis of said unitary body member.

2. The headset of claim 1, wherein in said closed state said headset has a first length, and in said rest state said headset has a second length, said second length being shorter than said first length.

3. The headset of claim 1, said at least one posterior electrode being configured, when said headset is donned, to be disposed above at least one occipital nerve branch of said user.

4. The headset of claim 1, said unitary body member also comprising: an interim member disposed between said anterior member and said at least one posterior member.

5. The headset of claim 4, wherein in said closed state of said headset, said anterior member and said at least one posterior member are vertically movable relative to one another.

6. The headset of claim 4, wherein said interim member comprises a semi-rigid portion and a stretchable portion, wherein in said rest state said semi-rigid portion defines the structure of said interim member, such that said interim member contributes to said monolithic unit and in said closed state of said unitary body member said stretchable portion is stretched to extend beyond the length of said semi-rigid portion thereby defining a flexible portion at which said anterior member and said at least one posterior member are vertically movable relative to one another, while remaining in parallel planes to one another.

7. The headset of claim 4, further comprising at least one anterior electrode mounted on an inner surface of said anterior member.

8. The headset of claim 7, said at least one anterior electrode configured, when said headset is donned, to be disposed above at least one of the supratrochlear nerves and the supraorbital nerves of said user.

9. The headset of claim 4, wherein in said rest state of said headset, longitudinal axes of said anterior member and of said at least one posterior member are vertically fixed relative to one another.

10. The headset of claim 1, wherein said processing unit is mounted on said unitary body member and communicates with said at least one posterior electrode via at least one electrical conductor and wherein at least part of said at least one electrical conductor passes through a stretchable portion of said unitary body member.

11. The headset of claim 1, also comprising at least one size adjustment mechanism, enabling adjustment of the circumference of said unitary body member to comfortably fit circumferentially about said head of said user, said at least one size adjustment mechanism configured to change an elastic length of an elastic portion of said unitary body member, without changing the physical length of said unitary body member.

12. The headset of claim 1, wherein said closure mechanism comprises a first magnet defining a first spherical surface disposed at one of said ends and a second magnet defining a second spherical surface disposed at the other of said ends, each of said first and second magnets being disposed in a magnet housing, wherein said first and second spherical surfaces of said first and second magnets are adapted to engage one another at a single point, thereby to close said headset.

13. The headset of claim 1, wherein said at least one posterior electrode is configured to be positioned against the skin of the head of said user by donning of said headset on the user's head.

14. The headset of claim 1, wherein the closure mechanism is formed by the ends of said unitary body member such that in the closed state of the closure mechanism, at least a portion of the closure mechanism is not disposed radially exterior to the unitary body member.

15. The headset of claim 1, wherein the closure mechanism is formed by the ends of said unitary body member such that in the closed state of the closure mechanism, at least a portion of a vertical footprint of the closure mechanism does not overlap a vertical footprint of the unitary body member.

16. The headset of claim 1, wherein the closure mechanism is connected to, and is disposed on, the at least one posterior member.

17. A method of donning a headset on the head of a user, the method comprising: providing a headset according to claim 1, said headset being in said rest state; positioning said headset adjacent the head of said user, such that at least said tapered end of said at least one posterior member is positioned against the skin of the head of said user adjacent temples of the user; pushing said headset rearwardly, such that during said pushing said tapered end of said at least one posterior member passes above ears of the user toward the back of the head of the user; and using said closure mechanism, closing said unitary body member into said closed state, thereby encircling said head of said user and securing said headset on said head of said user.

18. The method of claim 17, further comprising, during said pushing of said headset rearwardly, plowing through said hair and clearing an area of said scalp of said user for physical contact of said at least one posterior electrode therewith.

19. The method of claim 17, wherein said pushing said headset rearwardly comprises maintaining an angular orientation of said headset relative to the head of the user.

\* \* \* \* \*